US012612656B2

(12) United States Patent
Robinson et al.

(10) Patent No.: US 12,612,656 B2
(45) Date of Patent: Apr. 28, 2026

(54) PARTICLE-BASED ISOLATION OF PROTEINS AND OTHER ANALYTES

(71) Applicant: Nautilus Subsidiary, Inc., Seattle, WA (US)

(72) Inventors: Julia Robinson, East Palo Alto, CA (US); Tural Aksel, Redwood City, CA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 204 days.

(21) Appl. No.: 18/058,000

(22) Filed: Nov. 22, 2022

(65) Prior Publication Data

US 2023/0167488 A1 Jun. 1, 2023

Related U.S. Application Data

(60) Provisional application No. 63/284,483, filed on Nov. 30, 2021.

(51) Int. Cl.

| | |
|---|---|
| ***C12Q 1/68*** | (2018.01) |
| ***C12Q 1/6816*** | (2018.01) |
| ***C12Q 1/6834*** | (2018.01) |
| ***C12Q 1/6837*** | (2018.01) |

(52) U.S. Cl.

CPC ......... *C12Q 1/6834* (2013.01); *C12Q 1/6816* (2013.01); *C12Q 1/6837* (2013.01); *C12Q 2525/205* (2013.01); *C12Q 2525/30* (2013.01)

(58) Field of Classification Search

CPC ................ C12Q 1/6816; C12Q 1/6834; B01L 2300/0636; B01L 2200/10; B01L 2300/0819; B01L 3/5085; B01L 3/50855; B01L 2300/0861

See application file for complete search history.

(56) References Cited

U.S. PATENT DOCUMENTS

| | | | |
|---|---|---|---|
| 5,324,633 | A | 6/1994 | Fodor et al. |
| 5,445,934 | A | 8/1995 | Fodor et al. |
| 5,849,878 | A | 12/1998 | Cantor et al. |
| 5,919,626 | A | 7/1999 | Shi et al. |
| 6,255,469 | B1 | 7/2001 | Seeman et al. |
| 6,391,625 | B1 | 5/2002 | Park et al. |
| 6,589,726 | B1 | 7/2003 | Butler et al. |
| 6,610,482 | B1 | 8/2003 | Fodor et al. |
| 6,720,595 | B2 | 4/2004 | Clevenger et al. |
| 6,737,236 | B1 | 5/2004 | Pieken et al. |
| 6,806,361 | B1 | 10/2004 | Kajisa et al. |
| 6,824,866 | B1 | 11/2004 | Glazer et al. |
| 6,998,241 | B2 | 2/2006 | Boga |
| 7,148,058 | B2 | 12/2006 | Charych et al. |
| 7,158,224 | B2 | 1/2007 | Montagu |
| 7,183,054 | B2 | 2/2007 | Myers et al. |
| 7,252,954 | B2 | 8/2007 | Wang et al. |
| 7,259,258 | B2 | 8/2007 | Kozlov et al. |
| 7,351,528 | B2 | 4/2008 | Landegren |
| 7,375,234 | B2 | 5/2008 | Sharpless et al. |
| 7,427,678 | B2 | 9/2008 | Pieken et al. |
| 7,598,363 | B2 | 10/2009 | Seeman et al. |
| 7,635,562 | B2 | 12/2009 | Harris et al. |
| 7,763,736 | B2 | 7/2010 | Sharpless et al. |
| 7,794,799 | B1 | 9/2010 | Kim et al. |
| 7,842,793 | B2 | 11/2010 | Rothemund |
| 7,855,054 | B2 | 12/2010 | Schneider et al. |
| 7,932,060 | B2 | 4/2011 | Nadeau et al. |
| 7,955,837 | B2 | 6/2011 | Pawlak et al. |
| 7,964,356 | B2 | 6/2011 | Zichi et al. |
| 8,013,134 | B2 | 9/2011 | Fredriksson |
| 8,133,719 | B2 | 3/2012 | Drmanac et al. |
| 8,222,047 | B2 | 7/2012 | Duffy et al. |
| 8,236,574 | B2 | 8/2012 | Duffy et al. |
| 8,268,554 | B2 | 9/2012 | Schallmeiner |
| 8,404,830 | B2 | 3/2013 | Zichi et al. |
| 8,415,171 | B2 | 4/2013 | Rissin et al. |
| 8,445,194 | B2 | 5/2013 | Drmanac et al. |
| 8,501,923 | B2 | 8/2013 | Rothemund |
| 8,685,894 | B2 | 4/2014 | Chaput et al. |
| 8,877,516 | B2 | 11/2014 | Lin et al. |
| 8,945,811 | B2 | 2/2015 | True |
| 8,945,830 | B2 | 2/2015 | Heil et al. |

(Continued)

FOREIGN PATENT DOCUMENTS

| | | |
|---|---|---|
| CN | 100500865 C | 6/2009 |
| EP | 1105529 B2 | 5/2013 |

(Continued)

OTHER PUBLICATIONS

Chirsof M. Niemeyer, The developments of semisynthetic DNA-protein conjugates, Trends in Biotechnology, vol. 20, pp. 395-401. (Year: 2002).*

Burgahn et al., Solid-phase synthesis and purification of protein-DNA origami nanostructures, Chemistry: A European Journal, vol. 25, pp. 3483-3488. (Year: 2019).*

3-Aminopropyl)triethoxysilane. Wikipedia.org. Apr. 5, 2019 (Apr. 5, 2019), entire document esp p. 1 (https://en.wikipedia.org/w/index.php?title=(3-Aminopropyl)triethoxysilaneoldid=891131780).

Anonymous. List of protein hydrodynamic diameters. Dynamic Biosensors. May 17, 2017, XP055857934, Available at https://www.dynamic-biosensors.com/project/list-of-protein-hydrodynamic-diameters/. Retrieved on Nov. 4, 2021.

Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.

(Continued)

*Primary Examiner* — Dana H Shin

(74) *Attorney, Agent, or Firm* — Orrick, Herrington & Sutcliffe, LLP

(57) ABSTRACT

Provided herein are methods, compositions and apparatus useful for individually manipulating and individually detecting analytes such as proteins. Analytes can be attached to particles to facilitate individual manipulation or detection of the particle-attached analytes. The particle-attached analytes can be composed of a single analyte attached to a single particle, such that no more than one analyte is attached per particle and no more than one particle is attached per analyte.

16 Claims, 11 Drawing Sheets

(56) References Cited

U.S. PATENT DOCUMENTS

| | | | |
|---|---|---|---|
| 8,975,026 | B2 | 3/2015 | Zichi et al. |
| 8,975,388 | B2 | 3/2015 | Zichi et al. |
| 9,163,056 | B2 | 10/2015 | Rohlloff et al. |
| 9,275,871 | B2 | 3/2016 | Sandhu |
| 9,330,932 | B1 | 5/2016 | Sills et al. |
| 9,340,416 | B2 | 5/2016 | Maune et al. |
| 9,395,359 | B2 | 7/2016 | Walt et al. |
| 9,404,919 | B2 | 8/2016 | Schneider et al. |
| 9,466,504 | B1 | 10/2016 | Sills et al. |
| 9,528,984 | B2 | 12/2016 | Mitra |
| 9,551,663 | B2 | 1/2017 | Rissin et al. |
| 9,556,360 | B2 | 1/2017 | McGall et al. |
| 9,625,469 | B2 | 4/2017 | Marcotte et al. |
| 9,678,068 | B2 | 6/2017 | Duffy et al. |
| 9,717,685 | B2 | 8/2017 | Shih et al. |
| 9,777,315 | B2 | 10/2017 | Fredriksson et al. |
| 9,796,749 | B2 | 10/2017 | Yin et al. |
| 9,880,175 | B2 | 1/2018 | Mitra |
| 9,881,786 | B2 | 1/2018 | Sills et al. |
| 9,926,566 | B2 | 3/2018 | Ochsner et al. |
| 9,938,314 | B2 | 4/2018 | Rohlloff et al. |
| 9,975,916 | B2 | 5/2018 | Yin et al. |
| 10,022,334 | B2 | 7/2018 | Farokhzad et al. |
| 10,099,920 | B2 | 10/2018 | Shen et al. |
| 10,175,248 | B2 | 1/2019 | Mitra |
| 10,221,207 | B2 | 3/2019 | Rohlloff et al. |
| 10,221,421 | B2 | 3/2019 | Jarvis et al. |
| 10,239,908 | B2 | 3/2019 | Rohlloff et al. |
| 10,316,321 | B2 | 6/2019 | Zichi et al. |
| 10,351,909 | B2 | 7/2019 | Drmanac et al. |
| 10,392,621 | B2 | 8/2019 | Ochsner et al. |
| 10,473,654 | B1 | 11/2019 | Mallick |
| 10,513,535 | B2 | 12/2019 | He et al. |
| 10,545,153 | B2 | 1/2020 | Marcotte et al. |
| 10,550,145 | B2 | 2/2020 | Han et al. |
| 10,571,473 | B2 | 2/2020 | Mitra |
| 10,604,543 | B2 | 3/2020 | Yin et al. |
| 10,646,505 | B2 | 5/2020 | Schulz et al. |
| 10,741,382 | B2 | 8/2020 | Sills et al. |
| 10,829,816 | B2 | 11/2020 | Staker et al. |
| 10,921,317 | B2 | 2/2021 | Mallick |
| 10,948,488 | B2 | 3/2021 | Mallick |
| 11,001,606 | B2 | 5/2021 | Tikhomirov et al. |
| 11,060,135 | B2 | 7/2021 | Bowen et al. |
| 11,125,748 | B2 | 9/2021 | Gopinath et al. |
| 11,162,192 | B2 | 11/2021 | Gopinath et al. |
| 11,192,083 | B2 | 12/2021 | Kraft et al. |
| 11,203,612 | B2 | 12/2021 | Gremyachinskiy et al. |
| 11,235,972 | B2 | 2/2022 | Gopalkrishnan et al. |
| 11,282,585 | B2 | 3/2022 | Patel et al. |
| 11,505,796 | B2 | 11/2022 | Aksel et al. |
| 2003/0054408 | A1 | 3/2003 | Ravi et al. |
| 2004/0023413 | A1 | 2/2004 | Opalsky |
| 2004/0091931 | A1 | 5/2004 | Gold |
| 2004/0209383 | A1 | 10/2004 | Yin et al. |
| 2005/0054118 | A1 | 3/2005 | Lebrun |
| 2005/0095577 | A1 | 5/2005 | Yang et al. |
| 2005/0287523 | A1 | 12/2005 | Letant et al. |
| 2006/0035220 | A1 | 2/2006 | Tashiro et al. |
| 2006/0160234 | A1 | 7/2006 | Lopez-Avila et al. |
| 2006/0263769 | A1 | 11/2006 | Luo et al. |
| 2007/0188750 | A1 | 8/2007 | Lundquist et al. |
| 2007/0218503 | A1 | 9/2007 | Mitra |
| 2008/0032310 | A1 | 2/2008 | Shannon et al. |
| 2009/0018028 | A1 | 1/2009 | Lindsay et al. |
| 2009/0214591 | A1 | 8/2009 | Manucharyan et al. |
| 2010/0069621 | A1 | 3/2010 | Maune et al. |
| 2010/0081134 | A1 | 4/2010 | Mirkin et al. |
| 2010/0151472 | A1 | 6/2010 | Nolan et al. |
| 2011/0065807 | A1 | 3/2011 | Radovic-Moreno et al. |
| 2011/0263688 | A1 | 10/2011 | Barany et al. |
| 2012/0077688 | A1 | 3/2012 | Bergo et al. |
| 2015/0004193 | A1 | 1/2015 | Chang et al. |
| 2015/0160204 | A1 | 6/2015 | Mitra |
| 2015/0185199 | A1 | 7/2015 | Joo et al. |
| 2015/0330974 | A1 | 11/2015 | Staker et al. |
| 2016/0060687 | A1 | 3/2016 | Zhu et al. |
| 2016/0102344 | A1 | 4/2016 | Niemeyer et al. |
| 2016/0310926 | A1 | 10/2016 | Sun et al. |
| 2017/0044245 | A1 | 2/2017 | Meng et al. |
| 2017/0175184 | A1 | 6/2017 | Drmanac et al. |
| 2017/0191051 | A1 | 7/2017 | Nikiforov |
| 2017/0283868 | A1 | 10/2017 | Beechem et al. |
| 2017/0327888 | A1 | 11/2017 | Ong et al. |
| 2018/0044663 | A1 | 2/2018 | Yan |
| 2018/0148514 | A1 | 5/2018 | Williams |
| 2018/0348629 | A1* | 12/2018 | Liu ....................... G03F 7/0002 |
| 2019/0145982 | A1 | 5/2019 | Chee et al. |
| 2019/0195869 | A1 | 6/2019 | Fan et al. |
| 2019/0323002 | A1 | 10/2019 | Gopinath et al. |
| 2020/0025752 | A1 | 1/2020 | Gopinath et al. |
| 2020/0025757 | A1 | 1/2020 | Gopinath et al. |
| 2020/0082914 | A1 | 3/2020 | Patel et al. |
| 2020/0090785 | A1 | 3/2020 | Patel et al. |
| 2020/0206145 | A1 | 7/2020 | Shi et al. |
| 2020/0232994 | A1 | 7/2020 | Mitra |
| 2020/0286584 | A9 | 9/2020 | Patel et al. |
| 2020/0289658 | A1 | 9/2020 | Stephanopoulos et al. |
| 2020/0318101 | A1 | 10/2020 | Mallick et al. |
| 2020/0348307 | A1 | 11/2020 | Beierle et al. |
| 2020/0348308 | A1 | 11/2020 | Chee et al. |
| 2021/0032775 | A1 | 2/2021 | Gopinath et al. |
| 2021/0101930 | A1 | 4/2021 | Gremyachinskiy et al. |
| 2021/0223238 | A1 | 7/2021 | Mallick |
| 2021/0239705 | A1 | 8/2021 | Mallick |
| 2021/0278400 | A1 | 9/2021 | Mallick |
| 2021/0355483 | A1 | 11/2021 | Chee et al. |
| 2021/0390705 | A1 | 12/2021 | Egertson et al. |
| 2022/0050049 | A1 | 2/2022 | Indermuhle et al. |
| 2022/0162684 | A1 | 5/2022 | Aksel et al. |
| 2022/0227890 | A1 | 7/2022 | Kapp et al. |
| 2022/0236282 | A1 | 7/2022 | Mallick et al. |
| 2022/0339181 | A1 | 10/2022 | Funke et al. |
| 2022/0379582 | A1 | 12/2022 | Sorelle et al. |
| 2022/0412998 | A1 | 12/2022 | Lobanov et al. |

FOREIGN PATENT DOCUMENTS

| | | | |
|---|---|---|---|
| EP | 2872898 | B1 | 12/2016 |
| EP | 3 699 141 | A1 | 8/2020 |
| EP | 3498865 | B1 | 10/2020 |
| WO | WO 01/46675 | A2 | 6/2001 |
| WO | WO 02/086081 | A2 | 10/2002 |
| WO | WO 2005/065814 | A1 | 7/2005 |
| WO | WO 2006/135527 | A2 | 12/2006 |
| WO | WO 2007/117444 | A2 | 10/2007 |
| WO | WO 2008/016644 | A1 | 2/2008 |
| WO | WO 2007/120208 | A3 | 8/2008 |
| WO | WO 2014/078855 | A1 | 5/2014 |
| WO | WO 2015/097077 | A2 | 7/2015 |
| WO | WO 2016/174525 | A1 | 11/2016 |
| WO | WO 2017/127762 | A1 | 7/2017 |
| WO | WO 201/102759 | A1 | 6/2018 |
| WO | WO 2019/036055 | A2 | 2/2019 |
| WO | WO 2019/059961 | A1 | 3/2019 |
| WO | WO 2019/133892 | A1 | 7/2019 |
| WO | WO 2019/195633 | A1 | 10/2019 |
| WO | WO 2019/211631 | A1 | 11/2019 |
| WO | WO 2019/236749 | A2 | 12/2019 |
| WO | WO 2020/106889 | A1 | 5/2020 |
| WO | WO 2020/223368 | A1 | 11/2020 |
| WO | WO 2020/254684 | A1 | 12/2020 |
| WO | WO 2021/074087 | A1 | 4/2021 |
| WO | WO 2021/087402 | A1 | 5/2021 |
| WO | WO 2022/060728 | A1 | 3/2022 |
| WO | WO 2022/182635 | A1 | 9/2022 |
| WO | WO 2022/212479 | A2 | 10/2022 |

OTHER PUBLICATIONS

Asseline, U. et al. "Development and Applications of Fluorescent Oligonucleotides" Curr. Org. Chem. (2006) 10:491-518.

Ayoglu, et al., Autoantibody Profiling in Multiple Sclerosis Using Arrays of Human Protein Fragments, Molecular & Cellular Proteomics,

(56) References Cited

OTHER PUBLICATIONS (12)9 Sep. 1, 2013 (Sep. 1, 2013), pp. 2657-2672, XP055294116, US , ISSN: 1535-9476, DOI: 10.1074/mcp.M112.026757.
Blatch, et al. The tetratricopeptide repeat: a structural motif mediating protein-protein interactions. Bioessays Nov. 1999;21 (11):932-939.
Buenrostro, et al. Quantitative analysis of RNA-protein interactions on a massively parallel array for mapping biophysical and evolutionary landscapes. Nat Biotechnol. Jun. 2014; 32(6):562-568.
Bunka et al. "Production and characterization of RNA aptamers specific for amyloid fibril epitopes," J Biol Chem, Sep. 18, 2007 (Sep. 18, 2007), vol. 282, No. 47, pp. 34500-34509.
Buus, et al. High-resolution mapping of linear antibody epitopes using ultrahigh-density peptide microarrays. Molecular & Cellular Proteomics 11.12 (2012): 1790-1800.
Choi, Youngeun et al. "A new reporter design based on DNA origami nanostructures for quantification of short oligonucleotides using microbeads", Scientific Reports, vol. 9, No. 1, Mar. 18, 2019.
Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.
Clever, G.H. et al. "DNA-Metal Base Pairs" Angew. Chem. Int. Ed. (2007) 46:6226-6236.
Cox, W.G. et al. "Fluorescent DNA Hybridization Probe Preparation Using Amine Modification and Reactive Dye Coupling" Biotechniques (2004) 36:114-122.
Cutler, et al., "Spherical Nucleic Acids", *J. Amer. Chem. Soc.*, 134: 1376-1391 (2012).
Derr, et al., "Tug of War in Motor Pri=otein Ensembles Revealed with a Programmable DNA Origami Scaffold", *Science*, 338, 662-665 (2012).
Domenyuk, et al. Plasma Exosome Profiling of Cancer Patients by a Next Generation Systems Biology Approach. Sci Rep. 2017; 7: 42741.
Drmanac et al., "Human Genome Sequencing Using Unchained Base Reads on Self-Assembling DNA Nanoarrays", *Science*, 327: 78-81 (2010).
Evanko, D. et al. "Hybridization Chain Reaction" Nat. Methods (2004) 1:186-187.
Fodor er al., Light-Directed Spatially Addressable Parallel Chemical Synthesis, Science, vol. 251, 767-773, 1991.
Ford et al. "Degenerate recognition of T cell epitopes: impact of T cell receptor reserve and stability of peptide:MHC complexes," Mol Immunol, Feb. 1, 2004 (Feb. 2, 2004), vol. 40, No. 14-15, pp. 1019-1025.
Galimidi, R.P. et al. "Intra-Spike Crosslinking Overcomes Antibody Evasion by HIV-1" Cell (2015) 160:433-446.
Gardner, A.F. et al. "Therminator DNA Polymerase: Modified Nucleotides and Unnatural Substrates" Front. Mol. Biosci. (2019) 6:28.
Garmendia, C. et al. "The Bacteriophage Phi29 DNA Polymerase, a Proofreading Enzyme" J. Bio. Chem. (1992) 267:2594-2599.
Gopinath, et al., "Optimized Assembly and Covalent Coupling of Single-Molecule JNA Origami Nanoarrays", *ACS Nano*, 8: 12030-12040 (2014).
Gyssels, E. et al. "Interstrand Cross-Linking of Nucleic Acids: From History to Recent and Future Applications" Modified Nucleic Acids in Biology and Medicine (2016) pp. 339-369.
He, et al. Fluorescence aptameric sensor for strand displacement amplification detection of cocaine. Analytical chemistry 82.4 (2010): 1358-1364.
Hookway et al., "Aggregate formation and suspension culture of human pluripotent stem cells and differentiated progeny", Methods, vol. 101, pp. 11-20, 2016.
Hung, Albert M. et al. Large-area spatially ordered arrays of gold nanoparticles directed by lithographically confined DNA origami. Nat Nanotechnol. Feb. 2010;5(2):121-6. doi: 10.1038/nnano.2009. 450. Epub Dec. 20, 2009.
Hunniger, et al. Just in time-selection: A rapid semiautomated SELEX of DNA aptamers using magnetic separation and BEAMing. Anal Chem. Nov. 4, 2014;86(21):10940-7.
Itzkovitz, S. et al. "Validating Transcripts with Probes and Imaging Technology" Nat. Methods (2011) 8:512-519.
Jaekel, A. et al., "Manipulating Enzymes Properties with DNA Nanostructures" Molecules 24(20):3694 (2019).
Janssen, et al. Nucleic acids for ultra-sensitive protein detection. Sensors (Basel). Jan. 21, 2013;13(1):1353-84.
Jensen, J.O. et al. "Nanoengineered Bioplatforms Based on DNA Origami [Point of View]" Proceedings of the IEEE 102:1046-1049 (2014).
Kang, H. The prevention and handling of the missing data. Korean journal of anesthesiology vol. 64,5 (2013): 402-6. doi:10.4097/kjae. 2013.64.5.402.
Kolb, H.C. et al., "Click Chemistry: Diverse Chemical Function from a Few Good Reactions" Angewandte Chemie International Edition. 40 (11): 2004-2021 (2001).
Krufczik, M. et al. "Combining Low Temperature Fluorescence DNA-Hybridization, Immunostaining, and Super-Resolution Localization Microscopy for Nano-Structure Analysis of ALU Elements and Their Influence on Chromatin Structure" Int. J. Mol. Sci. (2017) 18:1005-1020.
Laurenson, et al. Development of peptide aptamer microarrays for detection of HPV16oncoproteins in cell extracts, Analytical Biochemistry, Academic Press, Amsterdam,NL, vol. 410, No. 2, Oct. 30, 2010 (Oct. 30, 2010), pp. 161-170, XP028146256,ISSN: 0003-2697,DOI: 10.1016/J.AB.2010.10.038.
LI Weiping et al., "Multiplex electrochemical origami immunodevice based on cuboid silver-paper electrode and metal ions tagged nanoporous silver chitosan", (2014) Biosensors & Bioelectronics, vol. 56, pp. 167-173.
Lian et al., "Ultrasensitive detection of biomolecules with fluorescent dye-doped nanoparticles", Analytical Biochemistry, vol. 334, 2004, pp. 135-144.
Lin et al. Development of a novel peptide microarray for large-scale epitope mapping of food allergens, Journal of Allergy and Clinical Immunology, Elsevier, Amsterdam, NL,vol. 124, No. 2, Aug. 1, 2009 (Aug. 1, 2009), pp. 315-322.e3, XP026390934, ISSN: 0091-6749,DOI: 10.1016/J.JACI.2009.05.024.
Lundberg, E.P. et al. "A New Fixation Strategy for Addressable Nano-Network Building Blocks" Chem. Comm. (2010) 46:3714-3716.
Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70.
McKay, et al. Click Chemistry in Complex Mixtures: Bioorthogonal Bioconjugation. Chem Biol. Sep. 18, 2014;21(9): 1075-1101.
Meldal, et al. Cu-catalyzed azide-alkyne cycloaddition. Chem Rev. Aug. 2008;108(8):2952-3015. doi: 10.1021/cr0783479.
Musumeci, et al. Fluorescence sensing using DNA aptamers in cancer research and clinical diagnostics. Cancers 9.12 (2017): 174.
Nakamura, S. et al. "Creation of DNA Array Structure Equipped with Heat Resistance by Ultrafast Photocrosslinking" J. Chem. Technol. Biotechnol. (2013) 89:1086-1090.
Nonobe et al. A tabu search approach to the constraint satisfaction problem as a general problem solver. Eur. J. Oper. Res. 106 (1998): 599-623.
O'Flaherty, D.K. et al. "Site-Specific Covalent Capture of Human O6-alkylguanine-DNA-alkyltransferase Using Single-Stranded Intrastrand Cross-Linked DNA" Org. Biomol. Chem. (2016) 15:189-196.
Patronov et al. "Peptide binding prediction for the human class II MHC allele HLA-DP2: a molecular docking approach," BMC Struct Biol, Jul. 14, 2011 (Jul. 14, 2011), vol. 11, No. 32, pp. 1-10.
Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913Retrieved from the Internet: URL:http://www.nature.com/articles/nm.2913.

(56) References Cited

OTHER PUBLICATIONS

Rajendran, A. et al. "Photo-Cross-Linking-Assisted Thermal Stability of DNA Origami Structures and Its Application for Higher-Temperature Self-Assembly" JACS (2011) 133:14488-14491.
Randolph, J.B. et al. "Stability, Specificity, and Fluorescence Brightness of Mulitply-Labeled Fluorescent DNA Probes" Nuc. Acids Res. (1997) 25:2923-2929.
Reineke, et al. Epitope mapping protocols. Preface. Methods in molecular biology (Clifton, N.J.) vol. 524 (2009): v-vi.
Reyes et al. "Critical role of HLA-DR11" binding peptides' peripheral flanking residues in fully-protective malaria vaccine development, Biochem Biophys Res Commun, May 23, 2017 (May 23, 2017), vol. 489, No. 3, pp. 339-345.
Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.
Richer, et al., Epitope identification from fixed-complexity random-sequence peptide microarrays, Molecular & cellular proteomics, vol. 14, No. 1, Nov. 3, 2014, pp. 136-147.
Rissin, et al., "Single-Molecule enzyme-linked immunosorbent assay detects serum proteins at subfemtomalar concentrations", *Nat. Biotech*., 28: 595-599 (2010).
Rothemund et al., "Folding DNA to create nanoscale shapes and patterns", Nature Mar. 16, 2006;440(7082):297-300 (2006).
Rusmini, Federica et al. Protein immobilization strategies for protein biochips. Biomacromolecules vol. 8,6 (2007): 1775-89. doi:10.1021/bm061197b.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
Schweitzer et al. Immunoassays with rolling circle DNA amplification: a versatile platform for ultrasensitive antigen detection. Proceedings of the National Academy of Sciences. \USA. 97(18) (Aug. 2000):10113-10119.
She, et al. Comprehensive and quantitative mapping of RNA-protein interactions across a transcribed eukaryotic genome. Proc Natl Acad Sci U S A. Apr. 4, 2017; 114(14): 3619-3624.
Sigl et al., "Programmable icosahedral shell system for virus trapping", Nature Materials, vol. 20, Sep. 2021, 1281-1289.
Sinkeldam, R.W. et al. "Fluorescent Analogs of Biomolecular Building Blocks: Design, Properties and Applications" Chem. Rev. (2010) 110:2579-2619.
Sjoberg et al. Validation of affinity reagents using antigen microarrays, Newbiotechnology, vol. 29, No. 5, Jun. 1, 2012 pp. 555-563, XP055793929, NLISSN: 1871-6784, DOI: 10.1016/j.nbt.2011.11.009.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Spicer, C.D. et al. "Achieving Controlled BiomoleculeñBiomaterial Conjugation" Chem. Rev. (2018) 118(16):7702ñ7743.
Stawicki, C.M. et al., "Modular fluorescent nanoparticle DNA probes for detection of peptides and proteins" Scientific Reports 11:19921 (2021) [doi.org/10.1038/s41598-021-99084-4].
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
Sun, H. et al. "Coumarin-Induced DNA Ligation, Rearrangement to DNA Interstrand Crosslinks, and Photorelease of Coumarin Moiety" Chem BioChem (2016) 17:1-9.
Swaminathan et al., "Highly parallel single-molecule identification of proteins in zeptomole-scale mixtures", Nat Biotechnol 36, 1076-1082 (2018). https:--doi.org-10.1038-nbt.4278.
Tagawa, M. et al. "Stabilization of DNA Nanostructures by Photo-Cross-Linking" Soft Matter (2011) 7:10931-10934.
Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.
Tsourkas et al., "Hybridization kinetics and thermodynamics of molecular beacons", Nucleic Acids Research, 2003, vol. 31, No. 4, pp. 1319-1330.
Vauquelin, G. et al., "Exploring avidity: understanding the potential gains in functional affinity and target residence time of bivalent and heterobivalent ligands" British Journal of Pharmacology 168:1771-1785 (2013).
Wang, L. et al. "DNA Nanostructures in Cell Biology and Medicine" DNA Nanotechnology for Bioanalysis (2017) pp. 99-127.
Wilson, et al. Single-Step Selection of Bivalent Aptamers Validated by Comparison with SELEX Using High-Throughput Sequencing. PLoS One. 2014; 9(6): e100572.
Xu, Weidong et al., "Supporting Information Super-resolution Geometric Barcoding for Multiplexed miRNA Profiling", Angewandte Chemie, Oct. 22, 2018, figure S2.
Xu, Weidong et al., "Super-resolution Geometric Barcoding for Multiplexed miRNA Profiling", Angewandte Chemie International Edition, vol. 57, No. 43, Oct. 4, 2018, pp. 14075-14079.
Yang et al., "Programmable Site-Specific Functionalization of DNA Origami with Polynucleotide Brushes", Angewandte Chemie Int. Ed. https:--doi.org-10.1002-anie.202107829 Jul. 23, 2021.
Yang, et al., "Self-assembly of highly ordered DNA origami lattices at solid-liquid interfaces by controlling cation binding and exchang", *Nano Res. Lett*., 13, 3142-3150 (2020).
Zakeri, B et al., "Peptide tag forming a rapid covalent bond to a protein, through engineering a bacterial adhesin" PNAS 109 (12): E690-E697 (2012).
Zandian, Arash et al. Whole-Proteome Peptide Microarrays for Profiling Autoantibody Repertoires within Multiple Sclerosis and Narcolepsy. Journal of proteome research 16(3) 2017: 1300-1314.
Zhang, P. et al., "Capturing transient antibody conformations with DNA origami epitopes" Nature Communications 11:3114 (2020).
Zhao, Z. et al., "Organizing DNA origami tiles into larger structures using preformed scaffold frames" NanoLetters 11:2997-3002 (2011).
WO, International Search Report & Written Opinion for International Application No. PCT/US2022/080322, 11 Pages, Mar. 15, 2023.
Hoshino et al., "Interaction between synthetic particles and biomacromolecules: fundamental study of nonspecific interaction and design of nanoparticles that recognize target molecules", Polymer Journal (2014) 46, 537-545.
Abbasov et al., "A proteome-wide atlas of lysine-reactive chemistry", Nature Chemistry, vol. 13: 1081-1092, Nov. 2021.
Aebersold et al., "How many human proteoforms are there?", Nat. Chem. Biol., 14:206-214, Feb. 14, 2018.
Anderson & Anderson. The human plasma proteome: history, character, and diagnostic prospects. Molecular & Cellular Proteomics: MCP vol. 1,11 (2002): 845-67.
Blume et al., "Rapid, deep and precise profiling of the plasma proteome with multi-nanoparticle protein corona", Nature Communications, 11:3662 (2020).
Egertson et al., "A theoretical framework for proteome-scale single-molecule protein identification using multi-affinity protein binding reagents", BioRxiv, (2021); DOI: 10.1101/2021.10.11.463967.
Ho et al., Unification of Protein Abundance Datasets Yields a Quantitative *Saccharomyces cerevisiae* Proteome. Cell Systems, vol. 6,2 (2018): 192-205.e3. doi:10.1016/j.cels.2017.12.004.
Luo et al., "Dinitroimidazoles as bifunctional bioconjugation reagents for protein functionalization and peptide macrocyclizations", Nat. Comm., 10:142 (2019); https://doi.org/10.1038/s41467-018-08010-2.
Rappsilber et al., "Protocol for micro-purification, enrichment, pre-fraction and storage of peptides for proteomics using StageTips", Nat. Protoc., vol. 2, No. 8:1896-906, published online Aug. 2, 2007.
Wisniewski et al. "A Proteomic Ruler for Protein Copy Number and Concentration Estimation without Spike-in Standards", Molecular & Cellular Proteomics, 13(12):3497-506 (2014).

(56) References Cited

OTHER PUBLICATIONS

Zanon et al., "Profiling the Proteome-wide Selectivity of Diverse Electrophiles", ChemRxiv, 10.33774/chemrxiv-2021-w7rss-v2 (2021).

* cited by examiner

PARTICLE-BASED ISOLATION OF PROTEINS AND OTHER ANALYTES

CROSS REFERENCE TO RELATED APPLICATIONS

This application claims priority to U.S. Provisional Application No. 63/284,483, filed on Nov. 30, 2021, which application is incorporated herein by reference.

BACKGROUND

Genomics, the detection and quantification of genes, has advanced in the last few decades at a speed and intensity that has the hallmarks of a scientific revolution. This revolution has manifest recently with the emergence of next-generation DNA sequencing tools that are profoundly altering our understanding of human health and, in turn, opening the doors to personalized medicine. An individual's genome is a set of instructions for the structure and function of cellular components that substantially influence risks for developing particular diseases, propensities for certain behaviors, and outcomes for specific therapeutic interventions, such as efficacy and safety of pharmaceutical treatments. Although the genome provides a strong basis for prediction, the information is not definitive regarding what is actually happening at any given time or in any given situation, for example, when a patient is sick and experiencing symptoms that could be attributed to a variety of different conditions. Proteomics, the analysis of the variety of proteins that are present at a given time and situation, provides this potential. However, proteomics awaits transformative advances of the type that have recently catapulted genomics. Several technologies that have fueled the genomics revolution, do not appear to be readily transferrable to proteomics. For example, the most common genome detection platforms in use today are configured to break up extremely long chromosomes into DNA fragments and to manipulate those fragments to a readily detectable form. Typically, those manipulations include capturing the DNA fragments in a way that they can be individually resolved and amplifying the DNA fragments to produce sufficient signal for detection. Proteins cannot be amplified using DNA amplification techniques and their increased chemical complexity compared to DNA complicates efforts to capture proteins at scales approaching those achieved in genomics platforms.

There is a need for efficient methods to capture proteins in a way that they can be individually detected or manipulated. The present disclosure satisfies this need and provides other advantages as well.

SUMMARY

The present disclosure provides a method for attaching a particle to a protein. The method can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state wherein a single stranded nucleic acid linker attaches each of the particles to a second reactive moiety; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) hybridizing an oligonucleotide to the single stranded nucleic acid linker, thereby converting the nucleic acid linker from a single stranded conformation to a double stranded conformation.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a nucleic acid linker attaches the second reactive moiety to each of the particles, and wherein the nucleic acid linker is hybridized to a surface of the particle; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) dehybridizing the nucleic acid linker from the surface of the particle and hybridizing an oligonucleotide to the single stranded nucleic acid linker, thereby converting the nucleic acid linker to an extended conformation.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a nucleic acid linker attaches the second reactive moiety to each of the particles, and wherein the nucleic acid linker has a region of internal complementarity; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) dehybridizing the region of internal complementarity and hybridizing an oligonucleotide to the single stranded nucleic acid linker, thereby converting the nucleic acid linker to an extended conformation.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a linker attached a first domain of each of the individual particles to a second domain of each of the individual particles, respectively, the linker comprising a cleavable bond; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) cleaving the cleavable bond, thereby converting the particle of the particle-protein conjugate to a second state wherein the first domain is more distant from the second domain compared to the first state. Alternatively, step (c) can include cleaving the cleavable bond, thereby converting the particle of the particle-protein conjugate to a second state wherein the first domain is more proximal to the second domain compared to the first state.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) crosslinking a first domain of the particle to a second domain of the particle, thereby converting the particle of the particle-protein conjugate to a second state wherein the first domain is more distant from the second domain compared to the first state. Alternatively, step (c) can include crosslinking a first domain of the particle to a second domain of the particle, thereby converting the particle of the particle-protein conjugate to a second state wherein the first domain is more proximal to the second domain compared to the first state.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) attaching a first domain of the particle to a solid support and attaching a second domain of the particle to a solid support, thereby converting the particle of the particle-protein conjugate to a second state wherein the first domain is more distant from the second domain compared to the first state. Alternatively, step (c) can include attaching a first domain of the particle to a solid support and attaching a second domain of the particle to a solid support, thereby converting the particle of the particle-protein conjugate to a second state wherein the first domain is more proximal to the second domain compared to the first state.

A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a blocking moiety is attached to each of the individual particles; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) removing the blocking moiety from the particle of the particle-protein conjugate, thereby converting the particle of the particle-protein conjugate to a second state that lacks the blocking moiety. Alternatively, step (c) can include cross-linking the blocking moiety to a second moiety of the individual particle to which the blocking moiety is attached, thereby converting the particle of the particle-protein conjugate to a second state. As a further alternative, step (c) can include attaching the blocking moiety of the particle-protein conjugate to a solid support, thereby converting the particle of the particle-protein conjugate to a second state.

The present disclosure also provides a method for attaching a particle to a protein, the method including steps of (a) forming a reaction mixture including: (i) a plurality of proteins, wherein individual proteins of the plurality of proteins each include a plurality of first reactive moieties, and (ii) a plurality of immobilized particles, wherein individual immobilized particles of the plurality of immobilized particles each includes a second reactive moiety, wherein the second reactive moiety of the immobilized particles is reactive with the first reactive moieties of the proteins, and wherein the immobilized particles are attached to one or more solid supports; (b) reacting a first reactive moiety of a protein in the reaction mixture with a second reactive moiety of an immobilized particle in the reaction mixture to attach the protein to the immobilized particle via a bond formed between the first reactive moiety of the protein and the second reactive moiety of the immobilized particle, thereby forming an immobilized particle-protein conjugate; and (c) detaching the immobilized particle-protein conjugate from the solid support, thereby producing a solution-phase particle-protein conjugate. Optionally, the method can further include (d) removing unreacted proteins from the reaction mixture after step (b) and repeating step (a) using the unreacted proteins instead of the plurality of proteins. In a further option, the method can include modifying the unreacted proteins to have additional first reactive moieties after step (b) and prior to the repeating of step (a). The additional first reactive moieties can be attached to the unreacted proteins using an attachment chemistry that differs from chemistry used to attach the first reactive moieties to the plurality of proteins prior to step (a). For example, the attachment chemistry used to attach the additional first reactive moieties to the unreacted proteins can modify different amino acid residue types than the residue types modified by the chemistry used to attach the first reactive moieties to the plurality of proteins prior to step (a).

The present disclosure provides a method of binding a probe to a protein. The method can include steps of (a) forming a reaction mixture including: (i) a plurality of proteins, wherein individual proteins of the plurality of proteins each include a plurality of first reactive moieties, and (ii) a plurality of particles, wherein individual particles of the plurality of particles each include a second reactive moiety, wherein the second reactive moiety of the particles is reactive with the first reactive moieties of the proteins, and wherein the particles are in a first state; (b) reacting a first reactive moiety of a protein in the reaction mixture with a second reactive moiety of a particle in the reaction mixture to attach the protein to the particle via a bond formed between the first reactive moiety of the protein and the second reactive moiety of a particle, thereby forming a particle-protein conjugate; and (c) performing a binding reaction including: (i) the particle-protein conjugate, wherein the particle of the particle-protein conjugate is in a second state, and (ii) a probe having affinity for the protein, thereby forming a particle-complex conjugate comprising the probe bound to the protein of the particle-protein conjugate.

In some configurations, a method of binding a probe to a protein can include steps of (a) forming a reaction mixture including: (i) a plurality of proteins, wherein individual proteins of the plurality of proteins each includes a plurality of first reactive moieties, (ii) a plurality of immobilized particles, wherein individual immobilized particles of the plurality of immobilized particles each includes a second reactive moiety, wherein the second reactive moiety of the immobilized particles is reactive with the first reactive moieties of the proteins, and wherein the immobilized particles are attached to a solid support; (b) reacting a first reactive moiety of a protein in the reaction mixture with a second reactive moiety of an immobilized particle in the reaction mixture to attach the protein to the immobilized particle via a bond formed between the first reactive moiety of the protein and the second reactive moiety of the immobilized particle; and (c) detaching the immobilized particle from the solid support, thereby producing a particle-protein conjugate including the protein attached to the particle in solution; and (d) binding a probe to the protein of the particle-protein conjugate.

DETAILED DESCRIPTION

Figure 1:
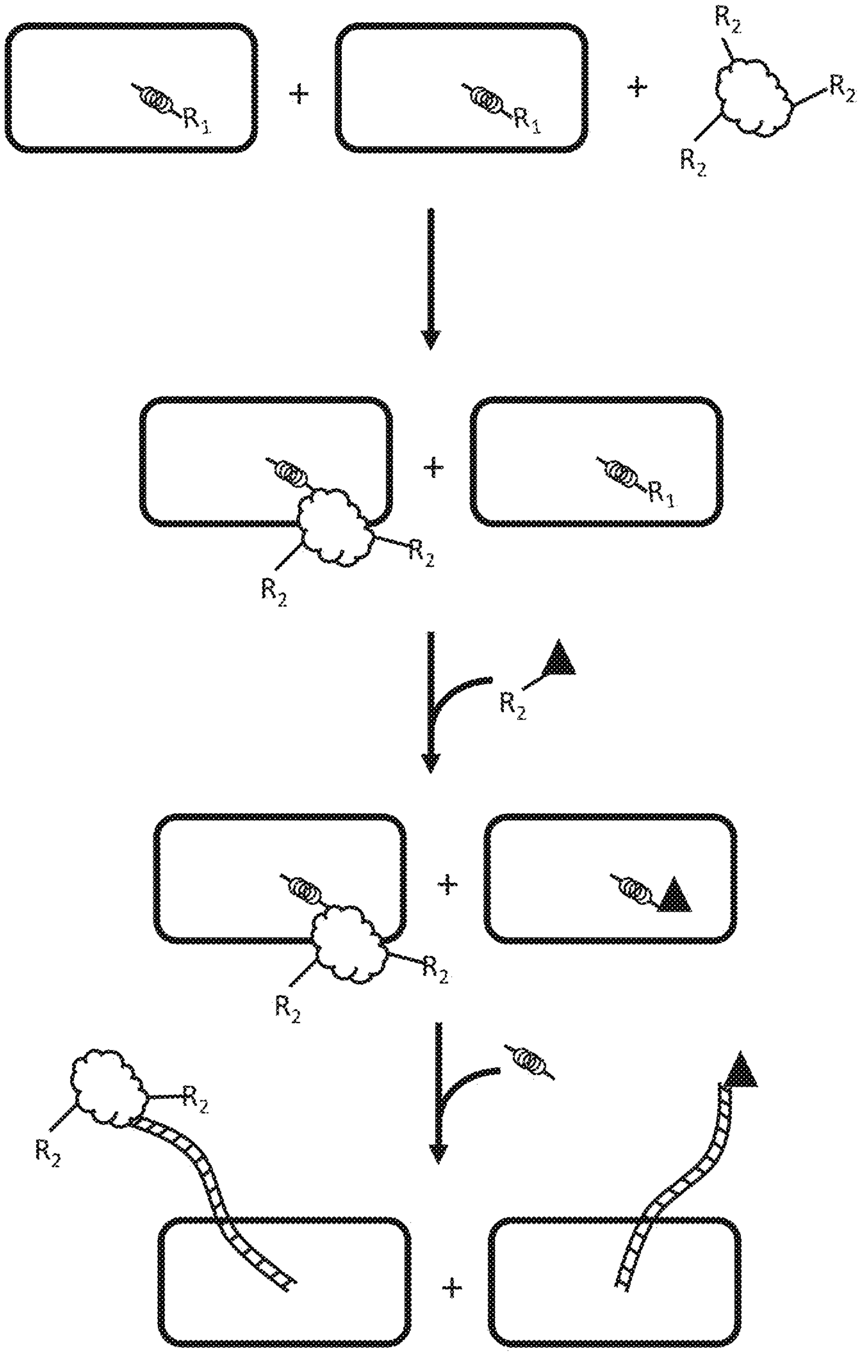
FIG. 1 illustrates a method for attaching a protein to a particle via a single-stranded nucleic acid linker and then converting the nucleic acid linker to double-stranded form.

The present disclosure provides methods, compositions and apparatus that can be used to individually manipulate and individually detect proteins. In particular configurations, the methods, compositions or apparatus can be used for manipulation or detection of a plurality of proteins such that the proteins are individually treated or resolved even when the plurality of proteins is processed in bulk. For example, multiplex configurations are provided in which a plurality of proteins can be detected in parallel and in which individual proteins can be resolved from each other. Similarly, a plurality of proteins can be processed in parallel, for example, in a chemical modification process or synthetic process, and individual proteins can be selectively manipulated or manipulated to different degrees during the process. Alternatively, a bulk process can be configured to manipulate a plurality of proteins in a serial process, wherein individual proteins can be selectively manipulated or detected in the process.

A method, composition or apparatus of the present disclosure can be used to individually manipulate or detect a plurality of proteins in a homogeneous protein sample wherein the proteins have the same primary structure (i.e. the same amino acid sequence), or in a heterogenous protein sample wherein the plurality of proteins have different primary structures. For example, a heterogeneous protein sample can include some or all proteins of a proteome obtained from a biological source. By way of further example, a proteome or fraction thereof can include a variety of proteins obtained from an organism, tissue, cell, or organelle. Even higher complexity samples can be used such as those including a variety of proteins obtained from multiple organisms, such as a microbiome, ecological community, forensic sample, or the like. A homogenous sample can be obtained by applying biochemical separation or fractionation techniques to the above heterogeneous samples or to other protein containing sources.

In particular configurations of the methods, compositions and apparatus set forth herein, proteins can be attached to particles to facilitate individual manipulation or detection of the particle-attached proteins. A plurality of particle-attached proteins can include particles that are each attached to a single protein of the plurality, wherein the proteins are each attached to a single particle of the plurality. The single protein can be composed of a single chain of amino acids. This single-chain protein can be in a native or denatured state. Any covalent linkages that would have otherwise attached two or more chains can be absent from the single-chain protein. For example, thioether bonds between cysteines on two amino acid chains can be absent due to the cysteines being in a reduced state, and in some cases the cysteines can be alkylated or otherwise functionalized to prevent thioether bond formation. Alternatively, a single particle-attached protein can be composed of multiple subunits, each subunit being composed of a single chain of amino acids. Generally, a particle-attached protein that has multiple subunits will be in a native state to reflect native quaternary structure of the protein. However, a single particle-attached protein can optionally include two or more denatured amino acid chains, for example, in a configuration wherein the amino acid chains are covalently bonded via a thioether linkage between cysteines or via other covalent linkages. Whether the proteins are composed of only single amino acid chains or multi-chain complexes, a plurality of particle-attached proteins can optionally include no more than one protein per particle and no more than one particle per protein. A method set forth herein can be configured to react a plurality of proteins with a plurality of particles to yield attachment of no more than one of the proteins per particle and no more than one of the particles per protein.

Particles that are attached to individual proteins can facilitate separation of the proteins from each other. For example, the particles can be attached to discrete locations on a solid support, whereby the proteins to which they are attached can be individually resolved. The protein-attached particles can be detected, for example, due to contact with another reagent such as an affinity reagent or a reactive reagent. The presence of only one particle per protein can beneficially facilitate access of reagents to the particle-attached proteins, and avoid hindering reagents from contacting the protein, for example, via steric hindrance or charge repulsion by additional particles attached to the protein.

A further benefit of the present disclosure is that attachment of particles to a variety of different proteins can facilitate bulk processing of the proteins since structural or functional characteristics that are common to the particles can be exploited in the process. For example, a plurality of particle-attached proteins can be separated from other components in a sample such as contaminants or unreacted reagents. This can be achieved by employing a separation technique that is selective for the particles. As this example demonstrates, the particles can provide normalization or uniformity when processing a complex sample having proteins with diverse structural and functional characteristics.

Attachment of proteins to particles can also provide the advantage of solubilizing the particle-attached proteins. For example, membrane proteins can be attached to particles, such as structured nucleic acid particles (SNAPs), and the SNAPs can prevent the membrane proteins from precipitating or otherwise being insoluble in aqueous solution. Similarly, denatured proteins can be attached to SNAPs or other particles to provide solubility to the denatured proteins. Membrane proteins, denatured proteins or other proteins that are prone to insolubility in aqueous solvents can be attached to SNAPs or other particles in organic solvents or in the presence of surfactants to facilitate the attachment reaction. The particle-attached proteins can then be separated from the organic solvent or surfactant for subsequent steps set forth herein, for example, steps that are carried out in aqueous solvent. Such steps can include, for example, attachment of the proteins to solid support (for example, via attachment of a particle to which the protein is attached), detection of the proteins, digestions of the proteins to form peptide fragments for subsequent assay (for example, subsequent assay in a mass spectrometer or on an array), or the like.

An effective configuration to achieve one-to-one attachment of protein to particle is to react a particle having a single first reactive moiety with a protein having a single second reactive moiety, the first and second moieties reacting to form an attachment of the protein to the particle. Such a configuration may not always be convenient or even possible. Proteins are chemically complex due to the diversity of amino acids they typically contain. For example, a variety of aliphatic, polar, amide-containing, sulfur-containing, carbonyl-containing, hydroxyl-containing aromatic, anionic and/or cationic side chains occur across the 20 amino acids used by most organisms as protein building blocks. Moreover, several of these side chains can be post-translationally modified to yield different chemical forms, thereby expanding the variety of reactive moieties that occur in a proteome or other complex protein sample. Accordingly, a proteome or other protein sample can include a large variety of different amino acid sequences and a large variety of sequence lengths. A further complication arises since, even if a particular amino acid type can be selectively reacted in the presence of other amino acid types, the particular amino acid may occur multiply in a given protein. For example, cysteines are a favored target for selective modification compared to other amino acid types, but cysteines are present multiple times in many proteins found in nature, cysteines accounting for about 1.4% of all amino acids in the UniProt database (see Weidemann et al., *Front. Chem.,* 8:1-8 (2020), which is incorporated herein by reference). A large number of proteins in a typical proteome sample are likely to each contain multiple amino acids of any given type such that reaction of the proteome sample with a reagent that selectively modifies that type of amino acid is likely to produce a large number of individual proteins each having multiple modifications. As the complexity of a protein sample increases, the ability to functionalize all of the proteins in the sample to contain only a single reactive moiety decreases.

The methods, compositions and apparatus of the present disclosure are well suited for providing one-to-one attachment of proteins to particles even if the proteins have more than one reactive moiety capable of attaching to the particles. As set forth in further detail below, particles provided herein can be in a first state that inhibits an attached protein from reacting with a second particle. Optionally, the first state can be a conformational state for the particle or a component thereof. For example, particles can have a linker that attaches to a protein in a conformation that inhibits the attached protein from contacting a second particle. Optionally, the first state can be a compositional state. For example, particles can have blocking moieties that inhibit the reactive moieties of two particles from coming into close enough proximity with each other to attach to the same protein. Optionally, the first state can be a state of mobility. For example, particles can be immobilized such that a protein attached to a first immobilized particle cannot contact a second immobilized particle. In some cases, a first state of a particle may also inhibit a particle-attached protein from interacting with reagents used for detecting the protein, such as affinity reagents or chemically reactive reagents.

Particles of the present disclosure can be capable of toggling from a first state to a second state, wherein the second state allows a particle-attached protein to interact with other particles or reagents used for detecting the protein. Optionally, the second state can be a conformational state for the particle or a component thereof. For example, a linker that attaches a protein to a particle can adopt a more extended conformation in the second state compared to a first state, thereby allowing the protein to access other reagents more readily. Optionally, the second state can be a compositional state. For example, blocking moieties that were present in a first state can be removed. Optionally, the second state can be a state of mobility. For example, particles can be in fluid phase such that a protein attached to a fluid phase particle can contact a second particle.

One-to-one attachment of proteins to particles can be facilitated by appropriate stoichiometry or proteins and particles during attachment reactions. A desired stoichiometry can be forced on a reaction between proteins and particles set forth herein, for example, by choosing reactive moieties having desired reactivity, by managing the concentration of the reactants, by managing conditions that influence reactivity of the reactants, by adjusting reaction times, by adjusting reaction temperatures or other variations that will be recognized by those skilled in the art as effective in view of the present disclosure.

One-to-one attachment of proteins to particles can be achieved by reacting proteins to immobilized particles. Immobilization of the particles can be configured to inhibit two particles from contacting the same protein at the same time. Optionally, the particles can be removed from the immobilized state used for attachment of proteins and subsequently detected. For example, after being removed from the immobilized state the protein-attached particles can be attached to an array or other substrate used in a detection method set forth herein or known in the art. The use of a first solid support when attaching proteins to particles and a second solid support when detecting the particle-attached proteins can provide arrays containing a substantial fraction of the proteins in a given sample while having reduced incidence of sites having more than a single protein present. For example, a reaction for attaching proteins to immobilized particles can be carried out using a relative excess of particles on the first solid support, which can be useful when attempting to capture as much of the protein content of a sample as possible but has a downside of yielding a large fraction of empty particles (i.e. particles that lack an attached protein). The protein-attached particles can be separated from empty particles to produce an enriched population of protein-attached particles and this enriched population can be attached to the second solid support for subsequent assay. The use of separate solid supports for attaching proteins to particles and for assay of the particle-attached proteins can also provide the advantage of overcoming limitations of Poisson distributions when attempting to capture one protein per particle. For example, proteins can be randomly attached to particles on the first solid support under Poisson limited conditions that favor attachment of no more than one protein per particle, albeit while yielding a low overall fraction of particles that attach to any protein at all. Empty particles then can be separated from protein-attached particles to yield an enriched population of protein-attached particles. The enriched population of protein-attached particles can be attached to the second solid support, thereby producing an array having a higher fraction of sites occupied by a single protein than would be expected from Poisson statistics.

Terms used herein will be understood to take on their ordinary meaning in the relevant art unless specified otherwise. Several terms used herein and their meanings are set forth below.

As used herein, the term "array" refers to a population of analytes (e.g. proteins) that are associated with unique identifiers such that the analytes can be distinguished from each other. A unique identifier can be a solid support (e.g. particle or bead), structured nucleic acid particle (SNAP), retaining component, site (e.g. spatial address) on a solid support, tag, label (e.g. luminophore), or barcode (e.g. nucleic acid barcode) that is associated with an analyte and that is distinct from other identifiers in the array. Analytes can be associated with unique identifiers by attachment, for example, via covalent or non-covalent bonds. An array can include different analytes that are each attached to different unique identifiers. An array can include different unique identifiers that are attached to the same or similar analytes. An array can include separate solid supports, or separate sites on the same solid support, that each bear a different analyte, wherein the different analytes can be identified according to the locations of the solid supports or sites. Analytes that can be included in an array can be, for example, nucleic acids such as structured nucleic acid particles, polypeptides, enzymes, affinity reagents, ligands, or receptors.

As used herein, the term "attached" refers to the state of two things being joined, fastened, adhered, connected or bound to each other. Attachment can be covalent or non-covalent. For example, a particle can be attached to a protein by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions, adhesion, adsorption, and hydrophobic interactions.

As used herein, the term "binding probability" refers to the probability that an affinity reagent or probe may be observed to interact with an analyte, for example, within a given binding context. A binding probability may be expressed as a discrete number (e.g., 0.4 or 40%) a matrix of discrete numbers, or as a mathematical model (e.g., a theoretical or empirical model). A binding probability may include one or more factors, including binding specificity, likelihood of locating a target epitope, or the likelihood of binding for a sufficient time to detect a binding interaction. An overall binding probability may include binding probability when all factors have been weighted relative to the binding context.

As used herein, the term "binding specificity" refers to the tendency of a probe to preferentially interact with a given analyte relative to other analytes. A probe may have a calculated, observed, known, or predicted binding specificity for a given analyte. Binding specificity may refer to selectivity for a single analyte in a given sample relative to one, some or all other analytes in the sample. Moreover, binding specificity may refer to selectivity for a subset of analytes in a given sample relative to at least one other analyte in the sample.

As used herein, the term "bioorthogonal reaction" refers to a chemical reaction that can occur within a biological system (in vitro and/or in vivo) without interfering with some or all native biological processes, functions, or activities of the biological system. A bioorthogonal reaction may be further characterized as being inert to components of a biological system other than those targeted by the bioorthogonal reaction. A bioorthogonal reaction may include a click reaction. Bioorthogonal or click reactions may include Staudinger ligation, copper-free click reactions, nitrone dipole cycloaddition, norbornene cycloaddition, oxanobornadiene cycloaddition, tetrazine ligation, [4+1] cycloaddition, tetrazole photoclick reactions, or quadricyclane ligation. A bioorthogonal reaction may utilize an enzymatic approach, such as attachment between a first molecule and a second molecule by an enzyme such as a sortase, a ligase, or a subtiligase. A bioorthogonal reaction may utilize an irreversible peptide capture system, such as SpyCatcher/SpyTag, SnoopCatcher/SnoopTag, or SdyCatcher/SdyTag.

As used herein, the term "click reaction" refers to single-step, thermodynamically-favorable conjugation reaction utilizing biocompatible reagents. A click reaction may be configured to not utilize toxic or biologically incompatible reagents (e.g., acids, bases, heavy metals) or to not generate toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kiloJoules/mole (kJ/mol), −10 kJ/mol, −25 kJ/mol, −50 kJ/mol, −100 kJ/mol, −200 kJ/mol, −300 kJ/mol, −400 kJ/mol, or less than −500 kJ/mol. Exemplary click reactions may include metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction (IEDDA), [3+2] cycloaddition, [4+1] cycloaddition, nucleophilic substitution, dihydroxylation, thiol-yne reaction, photoclick, nitrone dipole cycloaddition, norbornene cycloaddition, oxanobornadiene cycloaddition, tetrazine ligation, and tetrazole photoclick reactions. Exemplary reactive moieties utilized to perform click reactions may include alkenes, alkynes, azides, epoxides, amines, thiols, nitrones, isonitriles, isocyanides, aziridines, activated esters, and tetrazines. Other well-known click conjugation reactions may be used having complementary bioorthogonal reaction species, for example, where a first click component comprises a hydrazine moiety and a second click component comprises an aldehyde or ketone group, and where the product of such a reaction comprises a hydrazone functional group or equivalent. Exemplary bioorthogonal and click reactions are set forth in US Pat. App. Pub. No. 2021/0101930 A1, which is incorporated herein by reference.

As used herein, the term "colloid," when used in reference to beads or particles, means the beads or particles are suspended in another material such as a fluid. Beads or particles in a fluid colloid are capable of diffusing through the fluid. Beads or particles that are colloidal are not considered to be immobilized and vice versa.

The term "comprising" is intended herein to be open-ended, including not only the recited elements, but further encompassing any additional elements.

As used herein, the term "conformational state," when used in reference to a molecule or particle, refers to the shape or proportionate dimensions of the molecule or particle. At the molecular level conformational state can be characterized by the spatial arrangement of a molecule that results from the rotation of its atoms about their bonds. The conformational state of a macromolecule, such as a protein or nucleic acid, can be characterized in terms of secondary structure, tertiary structure, or quaternary structure. Secondary structure of a nucleic acid is the set of interactions between bases of the nucleic acid such as interactions formed by internal complementarity in a single stranded nucleic acid or by complementarity between two strands in a double helix. Tertiary structure of a nucleic acid is the three-dimensional shape of the nucleic acid as defined, for example, by the relative locations of its atoms in three-dimensional space. Quaternary structure of a nucleic acid is the overall shape resulting from interactions between two or more nucleic acids at a higher level than the secondary or tertiary levels. Secondary structure of a protein is the three-dimensional form of local segments of the protein which can be defined, for example, by the pattern of hydrogen bonds between the amino hydrogen and carboxyl oxygen atoms in the peptide backbone or by the regular pattern of backbone dihedral angles in a particular region of the Ramachandran plot for the protein. Tertiary structure of a protein is the three-dimensional shape of a single polypeptide chain backbone including, for example, interactions and bonds of side chains that form domains. Quaternary structure of a protein is the three-dimensional shape and interaction between the amino acids of multiple polypeptide chain backbones. A molecule or particle having a given composition may take on more than one conformational state with or without changes to its composition. For example, a protein having a given amino acid sequence (i.e. protein primary structure) may take on different conformations at the secondary, tertiary or quaternary level, and a nucleic acid having a given nucleotide sequence (i.e nucleic acid primary structure) may take on different conformations at the secondary, tertiary or quaternary level.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "epitope" refers to a molecule or part of a molecule, which is recognized by or binds specifically to a probe. Epitopes may include amino acid sequences that are sequentially adjacent in the primary structure of a protein or amino acids that are structurally adjacent in the secondary, tertiary or quaternary structure of a protein. An epitope can optionally be recognized by or bound to an antibody. However, an epitope need not necessarily be recognized by any antibody, for example, instead being recognized by an aptamer, miniprotein or other probe. An epitope can optionally bind an antibody to elicit an immune response. However, an epitope need not necessarily participate in, nor be capable of, eliciting an immune response.

As used herein, the term "exogenous," when used in reference to a moiety of a molecule, means a moiety that is not present in a natural analog of the molecule. For example, an exogenous label of an amino acid is a label that is not present on a naturally occurring amino acid. Similarly, an exogenous label that is present on an antibody is not found on the antibody in its native milieu.

As used herein, the term "fluid-phase," when used in reference to a molecule, means the molecule is in a state wherein it is mobile in a fluid, for example, being capable of diffusing through the fluid. A fluid-phase molecule is not in a state of immobilization on a solid-phase support.

As used herein, the term "immobilized," when used in reference to a molecule that is in contact with a fluid phase, refers to the molecule being prevented from diffusing in the fluid phase. For example, immobilization can occur due to the molecule being confined at, or attached to, a solid phase. Immobilization can be temporary (e.g. for the duration of one or more steps of a method set forth herein) or permanent. Immobilization can be reversible or irreversible under conditions utilized for a method, system or composition set forth herein.

As used herein, the term "label" refers to a molecule, or moiety thereof, that provides a detectable characteristic. The detectable characteristic can be, for example, an optical signal such as absorbance of radiation, luminescence emission, luminescence lifetime, luminescence polarization, fluorescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like. A label may produce a signal that is detectable in real-time (e.g., fluorescence, luminescence, radioactivity). A label may produce a signal that is detected off-line (e.g., a nucleic acid barcode) or in a time-resolved manner (e.g., time-resolved fluorescence). A label may produce a signal with a characteristic frequency, intensity, polarity, duration, wavelength, sequence, or fingerprint.

As used herein, the term "nucleic acid nanoball" refers to a globular or spherical nucleic acid structure. A nucleic acid nanoball may include a concatemer of sequence regions that arranges in a globular structure. A nucleic acid nanoball may include DNA, RNA, PNA, modified or non-natural nucleic acids, or combinations thereof.

As used herein, the term "nucleic acid origami" refers to a nucleic acid construct having an engineered tertiary or quaternary structure. A nucleic acid origami may include DNA, RNA, PNA, modified or non-natural nucleic acids, or combinations thereof. A nucleic acid origami may include a plurality of oligonucleotides that hybridize via sequence complementarity to produce the engineered structuring of the origami. A nucleic acid origami may include sections of single-stranded or double-stranded nucleic acid, or combinations thereof. Exemplary nucleic acid origami structures may include nanotubes, nanowires, cages, tiles, nanospheres, blocks, and combinations thereof. A nucleic acid origami can optionally include a relatively long scaffold nucleic acid to which multiple smaller nucleic acids hybridize, thereby creating folds and bends in the scaffold that produce an engineered structure. The scaffold nucleic acid can be circular or linear. The scaffold nucleic acid can be single stranded but for hybridization to the smaller nucleic acids. A smaller nucleic acid (sometimes referred to as a "staple") can hybridize to two regions of the scaffold, wherein the two regions of the scaffold are separated by an intervening region that does not hybridize to the smaller nucleic acid.

As used herein, the term "particle" means an object having a largest dimension between 50 nm and 1 mm. The object can be composed of a rigid or semi-rigid material. The particle can be insoluble in a fluid such as aqueous liquid. A particle can have a shape characterized, for example, as a sphere, ovoid, polyhedron, or other recognized shape whether having regular or irregular dimensions. Exemplary particles include, but are not limited to, structured nucleic acid particles (SNAPs) such as nucleic acid origami particles; optically detectable particles such as fluorescent nanoparticles, FluoSpheres™, and quantum dots; organic particles; inorganic particles; gel particles; or particles made from solid support materials set forth herein or known in the art.

As used herein, the term "protein" refers to a molecule including two or more amino acids joined by a peptide bond. A protein may also be referred to as a polypeptide, oligopeptide or peptide. Although the terms "protein," "polypeptide," "oligopeptide" and "peptide" may optionally be used to refer to molecules having different characteristics, such as amino acid composition, amino acid sequence, amino acid length, molecular weight, origin of the molecule or the like, the terms are not intended to inherently include such distinctions in all contexts. A protein can be a naturally occurring molecule, or synthetic molecule. A protein may include one or more non-natural amino acids, modified amino acids, or non-amino acid linkers. A protein may contain D-amino acid enantiomers, L-amino acid enantiomers or both. Amino acids of a protein may be modified naturally or synthetically, such as by post-translational modifications.

As used herein, the term "probe" refers to a molecule or other substance that is capable of binding to an analyte (e.g. protein) specifically, reproducibly or with high probability. Specific binding can be characterized in terms of a binding constant such as dissociation constant ($K_D$) that is less $10^{-4}$ M, $10^{-6}$ M, $10^{-8}$M, $10^{-10}$ M, $10^{-12}$ M, $10^{-14}$ M or lower. High probability can be characterized as a probability that is at least 0.25, 0.5, 0.51, 0.75, 0.9, 0.99 or higher (on a scale of 0 to 1). A probe can optionally be larger than, smaller than or the same size as an analyte to which it binds. A probe may form a reversible or irreversible interaction with an analyte. A probe may bind with an analyte in a covalent or non-covalent manner. A probe is typically non-catalytic and chemically non-reactive, thereby not permanently altering the chemical structure of an analyte to which it binds in a method set forth herein. Alternatively, a probe may be configured to catalyze or participate in a chemical modification (e.g., ligation, cleavage, concatenation, etc.) that produces a detectable change in an analyte to which it binds. Optionally, the product of the reaction can permit detection of the interaction. Exemplary probes include reactive probes (e.g., kinases, ligases, proteases, nucleases, etc.) or non-reactive probes (e.g., antibodies, antibody fragments, aptamers, DARPins, peptamers, etc.). The term "affinity reagent" is used herein synonymously with the term "probe."

As used herein, the term “reactive moiety” refers to a moiety or group of atoms in a molecule that confers chemical reactivity to the molecule. Reactive moieties may include organic moieties or may include inorganic atoms. Exemplary reactive moieties may include bioorthogonal reactants, click reactants, tetrazine (e.g. methyltetrazine), cycloalkene (e.g. transcyclooctene), alkyl, alkenyl, alkynyl, phenyl, halide, hydroxyl, carbonyl, aldehyde, acyl halide, ester, carboxylate, carboxyl, carboalkoxy, methoxy, hydroperoxy, ether, hemiacetal, hemiketal, acetal, ketal, orthoester, epoxide, carboxylic anhydride, carboxamide, amine, ketimine, aldimine, imide, azide, azo, cyanate, isocyanate, nitrate, nitrile, isonitrile, nitrosoxy, nitro, nitroso, oxime, pyridyl, carbamate, sulfhydryl, sulfide, disulfide, sulfinyl, sulfonyl, sulfinom, sulfo, thiocyanate, isothiocyanate, carbonothioyl, thioester, thionoester, phosphino, phosphono, phosphonate, phosphate, borono, boronate, and borinate functional groups.

As used herein, the term “site,” when used in reference to an array, means a location in an array occupied by, or configured to be occupied by, a particular molecule or analyte such as a polypeptide, nucleic acid, structured nucleic acid particle or reactive moiety. A site can contain only a single molecule, or it can contain a population of several molecules of the same species (i.e. an ensemble of the molecules). Alternatively, a site can include a population of molecules that are different species. Sites of an array are typically discrete. The discrete sites can be contiguous, or they can have interstitial spaces between each other. An array useful herein can have, for example, sites that are separated by less than 100 microns, 10 microns, 1 micron, 0.5 micron, 0.1 micron, 0.01 micron or less. Alternatively or additionally, an array can have sites that are separated by at least 0.01 micron, 0.1 micron, 0.5 micron, 1 micron, 10 microns, 100 microns or more. The sites can each have an area of less than 1 square millimeter, 500 square microns, 100 square microns, 25 square microns, 1 square micron or less. An array can include at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more sites, some or all of which are occupied by analytes or molecules.

As used herein, the term “solid support” refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass, modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, and polymers.

As used herein, the term “structured nucleic acid particle” or “SNAP” refers to a single- or multi-chain polynucleotide molecule having a compacted three-dimensional structure. The compacted three-dimensional structure can optionally be characterized in terms of hydrodynamic radius or Stoke’s radius of the SNAP relative to a random coil or other non-structured state for a nucleic acid having the same sequence length as the SNAP. The compacted three-dimensional structure can optionally be characterized with regard to tertiary structure. For example, a SNAP can be configured to have an increased number of internal binding interactions between regions of a polynucleotide strand, less distance between the regions, increased number of bends in the strand, and/or more acute bends in the strand, as compared to a nucleic acid molecule of similar length in a random coil or other non-structured state. Alternatively or additionally, the compacted three-dimensional structure can optionally be characterized with regard to quaternary structure. For example, a SNAP can be configured to have an increased number of interactions between polynucleotide strands or less distance between the strands, as compared to a nucleic acid molecule of similar length in a random coil or other non-structured state. In some configurations, the secondary structure (i.e. the helical twist or direction of the polynucleotide strand) of a SNAP can be configured to be more dense than a nucleic acid molecule of similar length in a random coil or other non-structured state. A SNAP can optionally be modified to permit attachment of additional molecules to the SNAP. A SNAP may contain DNA, RNA, PNA, modified or non-natural nucleic acids, or combinations thereof. A SNAP may include a plurality of oligonucleotides that hybridize to form the SNAP structure. The plurality of oligonucleotides in a SNAP may include oligonucleotides that are attached to other molecules (e.g., probes, analytes such as proteins, reactive moieties, or detectable labels) or are configured to be attached to other molecules (e.g., by functional groups). A SNAP may include engineered or rationally designed structures. Exemplary SNAPs include nucleic acid origami and nucleic acid nanoballs.

The embodiments set forth below and recited in the claims can be understood in view of the above definitions.

The present disclosure provides a method for attaching a particle to a protein. The method can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate.

Any of a variety of particles can be used in a method or composition set forth herein. A particle may be composed of a natural, artificial, or synthetic material. For example, a particle can be composed of a nucleic acid such as a structured nucleic acid particle (SNAP), nucleic acid nanoball or nucleic acid origami; protein nucleic acid; protein; synthetic polymer; polysaccharide; organic particle; inorganic particle; gel such as hydrogel; metal; semiconductors; ceramic, glass, silica or the like. A particle can optionally include material having a polymeric structure. Alternatively, a particle need not include a polymeric structure. In some embodiments, a particle has a composition that is similar to an analyte to which it is attached. For example, a plurality of particles that are composed of protein or amino acids can be attached to a protein analyte. Alternatively, a particle can have a composition that differs substantially from the composition of an analyte to which it is attached. For example, a plurality of particles that are attached to proteins can be composed partially or entirely of a material other than protein, such as nucleic acid material, non-proteinaceous organic material or inorganic material. In some configurations, a particle can lack one or more material or characteristic set forth herein.

Nucleic acid origami provides a particularly useful material for a particle of the present disclosure. Accordingly, a particle can include one or more nucleic acids having tertiary or quaternary structures such as spheres, cages, tubules, boxes, triangles, icosahedrons, tiles, blocks, trees, pyramids, wheels or combinations thereof. Examples of such structures formed with DNA origami are set forth in Zhao et al. *Nano Lett.* 11, 2997-3002 (2011); Rothemund *Nature* 440:297-302 (2006); Sigle et al, *Nature Materials* 20:1281-1289 (2021); or U.S. Pat. Nos. 8,501,923 or 9,340,416, each of which is incorporated herein by reference. In some configurations, a nucleic acid origami may include a scaffold and a plurality of staples. The scaffold can be configured as a single, continuous strand of nucleic acid, and the staples can be formed by oligonucleotides that hybridize, in whole or in part, with the scaffold nucleic acid. A particle including one or more nucleic acids (e.g. as found in origami or nanoball structures) may include regions of single-stranded nucleic acid, regions of double-stranded nucleic acid, or combinations thereof.

In some configurations, a nucleic acid origami includes a scaffold composed of a nucleic acid strand to which a plurality of oligonucleotides is hybridized. A nucleic acid origami may have a single scaffold molecule or multiple scaffold molecules. A scaffold nucleic acid can be linear (i.e. having a 3' end and 5' end) or circular (i.e. closed such that the scaffold lacks a 3' end and 5' end). A nucleic acid scaffold can be derived from a natural source, such as a viral genome or a bacterial plasmid. For example, a nucleic acid scaffold can include a single strand of an M13 viral genome. In other configurations, a nucleic acid scaffold may be synthetic. A scaffold nucleic acid can be single stranded but for a plurality of oligonucleotides hybridized thereto or short regions of internal complementarity. The size of a nucleic acid scaffold may vary to accommodate different uses. For example, a nucleic acid scaffold may include at least about 100, 500, 1000, 2500, 5000, 10000, 50000 or more nucleotides. Alternatively or additionally, a nucleic acid scaffold may include at most about 50000, 10000, 5000, 2500, 1000, 500, 100 or fewer nucleotides.

A nucleic acid origami can include a plurality of oligonucleotides that are hybridized to a scaffold nucleic acid. The plurality can include, for example, at least 2, 5, 10, 25, 50, 75, 100, 200 or more oligonucleotides that are hybridized to the scaffold nucleic acid. A first region of an oligonucleotide sequence can be hybridized to a scaffold nucleic acid while a second region is not hybridized to the scaffold. The second region can be in a single stranded state or, alternatively, can participate in a hairpin or other self-annealed structure in the oligonucleotide. In some cases, the second region of the oligonucleotide can hybridize to a complementary oligonucleotide to form a double-stranded region. An oligonucleotide can include two sequence regions that are hybridized to a scaffold nucleic acid, for example, to function as a 'staple' that restrains the structure of the scaffold. For example, a single oligonucleotide can hybridize to two regions of a scaffold that are separated from each other in the primary sequence of the scaffold. As such, the oligonucleotide can function to retain those two regions of the scaffold in proximity to each other or to otherwise constrain the scaffold to a desired conformation. Two sequence regions of an oligonucleotide staple can be adjacent to each other in the oligonucleotide sequence or separated by a third region that does not hybridize to the scaffold. One or more regions of an oligonucleotide that hybridize to a scaffold nucleic acid can be located at or near the 5' end of the oligonucleotide, at or near the 3' end of the oligonucleotide, or in a region of the oligonucleotide that is between the end regions. Oligonucleotides can be configured to hybridize with a nucleic acid scaffold, another oligonucleotide, a staple oligonucleotide, or a combination thereof. The oligonucleotides can be linear (i.e. having a 3' end and a 5' end) or closed (i.e. circular, lacking both 3' and 5' ends).

An oligonucleotide can be configured to act as a primer when hybridized to a nucleic acid origami. For example, the oligonucleotide can have a 3' end that is extendable by a polymerase. Extension can be carried out by a non-template directed polymerase such as terminal transferase. Optionally, the 3' end of the oligonucleotide can be complementary to a priming site region of a target nucleic acid such that a template region of the target can be copied by extension of the oligonucleotide 3' end.

An oligonucleotide that is included in a nucleic acid origami can have any of a variety of lengths. An oligonucleotide may have a length of at least about 10, 25, 50, 100, 250, 500, or more nucleotides. Alternatively or additionally, an oligonucleotide may have a length of no more than about 500, 250, 100, 50, 25, 10, or fewer nucleotides. An oligonucleotide in a nucleic acid origami may hybridize with another oligonucleotide or a scaffold strand forming a particular number of base pairs. An oligonucleotide may form a hybridization region of at least about 5, 6, 7, 8, 9, 10, 15, 20, 25, 50 or more consecutive or total base pairs. Alternatively or additionally, an oligonucleotide may form a hybridization region of no more than about 50, 25, 20, 15, 10, 9, 8, 7, 6, 5, or fewer consecutive or total base pairs.

A structured nucleic acid particle (e.g., nucleic acid origami, or nucleic acid nanoball) may be formed by an appropriate technique including, for example, those known in the art. Nucleic acid origami may be fabricated, for example, using techniques described in Rothemund, *Nature* 440:297-302 (2006), or U.S. Pat. No. 8,501,923 or 9,340,416, each of which is incorporated herein by reference. Nucleic acid origami may be designed using a software package, such as CADNANO (cadnano.org), ATHENA (github.com/lcbb/athena), or DAEDALUS (daedalus-dna-origami.org). Nucleic acid nanoballs may be fabricated by a method such as rolling circle amplification using a circular template to generate a nucleic acid amplicon consisting of a concatemer of template complements. The amplicon can be further modified to include crosslinks, for example, in the form of staples that hybridize to different regions of the amplicon. Exemplary methods for making nucleic acid nanoballs are described, for example, in U.S. Pat. No. 8,445,194, which is incorporated herein by reference.

A particle need not be composed primarily of nucleic acid and, in some cases, may be devoid of nucleic acids. For example, a particle can be composed of a solid support material, such as a silicon or silica nanoparticle, a carbon nanoparticle, a cellulose nanobead, a PEG nanobead, a polymeric nanoparticle (e.g., polyacrylate particles, polystyrene-based particles, FluoSpheres™, etc.), or a quantum dot. A particle may include solid materials and shell-like materials (e.g., carbon nanospheres, silicon oxide nanoshells, iron oxide nanospheres, polymethylmethacrylate nanospheres, etc.). A particle may include distinct surfaces, such as plates or shells. In some configurations, a particle may include a gel material.

A particle may have any of a variety of sizes and shapes to accommodate use in a desired application. For example, a particle can have a regular or symmetric shape or, alternatively, a particle can have an irregular or asymmetric shape. The shape can be rigid or pliable, again, to suit a particular use. A particle can have one or more flexible hinge about which two or more domains of the particle can rotate or otherwise move with respect to each other. The size or shape of a particle can be characterized with respect to length, area, or volume. The length, area or volume can be characterized in terms of a minimum, maximum, or average for a population.

Optionally, a particle can have a minimum, maximum or average length of at least about 50 nm, 100 nm, 250 nm, 500 nm, 1000 nm or more. Alternatively or additionally, a particle can have a minimum, maximum or average length of no more than about 1000 nm, 500 nm, 250 nm, 100 nm, 51 nm, or less.

Optionally, a particle can have a minimum, maximum or average volume of at least about 1 $\mu m^3$, 10 $\mu m^3$, 100 $\mu m^3$, 1 $mm^3$, 10 $mm^3$, 100 $mm^3$, 1 $cm^3$ or more. Alternatively or additionally, a particle can have a minimum, maximum or average volume of no more than about 1 $cm^3$, 100 $mm^3$, 10 $mm^3$, 1 $mm^3$, 100 $\mu m^3$, 10 $\mu m^3$, 1 $\mu m^3$ or less.

A particle can be characterized with respect to its footprint (e.g. occupied area on a surface). A footprint may have a regular shape or an approximately regular shape, such as triangular, square, rectangular, circular, ovoid, or polygon. Optionally, the minimum, maximum or average area for a particle footprint can be at least about 10 $nm^2$, 100 $nm^2$, 1 $\mu m^2$, 10 $\mu m^2$, 100 $\mu m^2$, 1 $mm^2$ or more. Alternatively or additionally, the minimum, maximum or average area for a particle footprint can be at most about 1 $mm^2$, 100 $\mu m^2$, 10 $\mu m^2$, 1 $\mu m^2$, 100 $nm^2$, 10 $nm^2$, or less.

A particle that is made or used in accordance with the present disclosure can be suspended in a fluid, immobilized on a solid support, or immobilized in another material such as a solid support material. For example, a population of particles can be colloidal for some, or all steps of a method set forth herein. Alternatively, a population of particles can be immobilized in, or on a solid support, for example, by gravity, non-covalent bonding, covalent bonding, coordination, adhesion or a combination thereof. Optionally, a first particle can be attached to a second particle. The first and second particles can compose the same material as each other or different materials from each other.

Particularly useful particles are configured to have a single reactive moiety for attaching a protein or other analyte of interest. By having no more than a single attachment point, a particle of the present disclosure can be configured to attach no more than one protein (or other analyte) of interest. Accordingly, a particle set forth herein can be useful for manipulating or detecting the attached protein at single-molecule resolution. Individual particles, each attached to a single protein can be individually resolved, for example, in an array of protein-particle conjugates. A single protein that is attached to a particle can be, for example, a single amino acid chain (e.g. a single-chain protein or single subunit dissociates from a multi-chain protein), or a complex of two or more single molecule chains (e.g. multiple subunits associated in a multi-chain protein). Furthermore, the particle-attached single protein can be in a native state or denatured state.

Structured nucleic acid particles can be configured to have a single reactive moiety or to be attached to a single analyte, such as a single protein. For example, a nucleic acid origami can be configured to include a single oligonucleotide having a single reactive moiety. Similarly, a nucleic acid origami can include a single reactive moiety in the scaffold nucleic acid of the origami structure. An oligonucleotide component of a nucleic acid origami or other SNAP may include one or more modified nucleotides. Alternatively or additionally, a scaffold of a nucleic acid origami or other SNAP may include one or more modified nucleotides. A modified nucleotide in a SNAP may provide a reactive moiety or attachment site for a protein or other analyte. A SNAP or component of a SNAP, such as an oligonucleotide or scaffold, may include at least about 1, 2, 3, 4, 5, 10, 25, 50 or more modified nucleotides. Alternatively or additionally, SNAP or component of a SNAP, such as an oligonucleotide or scaffold, may include no more than about 50, 25, 10, 5, 4, 3, 2, or 1 modified nucleotides. The number of proteins or other analytes attached to a nucleic acid origami can fall in one or both of these ranges.

A particle may have a shell, coating or layer (e.g., a polymer or hydrogel coating) that contains or can be modified to contain a single reactive moiety or to be attached to a single analyte, such as a single protein. A shell, coating, or layer of a particle may include a polymer or hydrogel that has been covalently or non-covalently joined to the particle surface. A particle may include at least about 1, 2, 3, 4, 5, 10, 25, 50 or more reactive moieties, for example, attached to a shell, coating or layer. Alternatively or additionally, a particle may include no more than about 50, 25, 10, 5, 4, 3, 2, or 1 reactive moieties, for example, attached to a shell, coating or layer. The number of proteins or other analytes attached to a nucleic acid origami can fall in one or both of these ranges.

The methods, compositions and apparatus of the present disclosure are particularly well suited for use with proteins. Although proteins are exemplified throughout the present disclosure, it will be understood that other analytes can be similarly used. Exemplary analytes include, but are not limited to, biomolecules, polysaccharides, nucleic acids (e.g. DNA or RNA), lipids, metabolites, hormones, vitamins, enzyme cofactors, therapeutic agents, candidate therapeutic agents or a combination thereof. An analyte can be a non-biological atom or molecule, such as a synthetic polymer, metal, metal oxide, ceramic, semiconductor, mineral, or a combination thereof.

One or more proteins that are used in a method, composition or apparatus herein, can be derived from a natural or synthetic source. Exemplary sources include, but are not limited to biological tissues, fluids, cells or subcellular compartments (e.g. organelles). For example, a sample can be derived from a tissue biopsy, biological fluid (e.g. blood, sweat, tears, plasma, extracellular fluid, urine, mucus, saliva, semen, vaginal fluid, synovial fluid, lymph, cerebrospinal fluid, peritoneal fluid, pleural fluid, amniotic fluid, intracellular fluid, extracellular fluid, etc.), fecal sample, hair sample, cultured cell, culture media, fixed tissue sample (e.g. fresh frozen or formalin-fixed paraffin-embedded) or product of a protein synthesis reaction. A protein source may include any sample where a protein is a native or expected constituent. For example, a primary source for a cancer biomarker protein may be a tumor biopsy sample or bodily fluid. Other sources include environmental samples or forensic samples.

Exemplary organisms from which proteins or other analytes can be derived include, for example, a mammal such as a rodent, mouse, rat, rabbit, guinea pig, ungulate, horse, sheep, pig, goat, cow, cat, dog, primate, non-human primate or human; a plant such as *Arabidopsis thaliana*, tobacco, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharomyces cerevisiae* or *Schizosaccharomyces pombe*; or a *Plasmodium falciparum*. Proteins can also be derived from a prokaryote such as a bacterium, *Escherichia coli, staphylococci* or *Mycoplasma pneumoniae*; an archae; a virus such as Hepatitis C virus, influenza virus, coronavirus, or human immunodeficiency virus; or a viroid. Proteins can be derived from a homogeneous culture or population of the above organisms or alternatively from a collection of several different organisms, for example, in a community or ecosystem.

In some cases, a protein or other biomolecule can be derived from an organism that is collected from a host organism. For example, a protein may be derived from a parasitic, pathogenic, symbiotic, or latent organism collected from a host organism. A protein can be derived from an organism, tissue, cell or biological fluid that is known or suspected of being linked with a disease state or disorder (e.g., cancer). Alternatively, a protein can be derived from an organism, tissue, cell or biological fluid that is known or suspected of not being linked to a particular disease state or disorder. For example, the proteins isolated from such a source can be used as a control for comparison to results acquired from a source that is known or suspected of being linked to the particular disease state or disorder. A sample may include a microbiome or substantial portion of a microbiome. In some cases, one or more proteins used in a method, composition or apparatus set forth herein may be obtained from a single source and no more than the single source. The single source can be, for example, a single organism (e.g. an individual human), single tissue, single cell, single organelle (e.g. endoplasmic reticulum, Golgi apparatus or nucleus), or single protein-containing particle (e.g., a viral particle or vesicle).

A method, composition or apparatus of the present disclosure can use or include a plurality of proteins having any of a variety of compositions such as a plurality of proteins composed of a proteome or fraction thereof. For example, a plurality of proteins can include solution-phase proteins, such as proteins in a biological sample or fraction thereof, or a plurality of proteins can include proteins that are immobilized, such as proteins attached to a particle or solid support. By way of further example, a plurality of proteins can include proteins that are detected, analyzed or identified in connection with a method, composition or apparatus of the present disclosure. The content of a plurality of proteins can be understood according to any of a variety of characteristics such as those set forth below or elsewhere herein.

A plurality of proteins can be characterized in terms of total protein mass. The total mass of protein in a liter of plasma has been estimated to be 70 g and the total mass of protein in a human cell has been estimated to be between 100 pg and 500 pg depending upon cells type. See Wisniewski et al. *Molecular & Cellular Proteomics* 13:10.1074/mcp.M113.037309, 3497-3506 (2014), which is incorporated herein by reference. A plurality of proteins used or included in a method, composition or apparatus set forth herein can include at least 1 pg, 10 pg, 100 pg, 1 ng, 10 ng, 100 ng, 1 μg, 10 μg, 100 μg, 1 mg, 10 mg, 100 mg or more protein by mass. Alternatively or additionally, a plurality of proteins may contain at most 100 mg, 10 mg, 1 mg, 100 μg, 10 μg, 1 μg, 100 ng, 10 ng, 1 ng, 100 pg, 10 pg, 1 pg or less protein by mass.

A plurality of proteins can be characterized in terms of percent mass relative to a given source such as a biological source (e.g. cell, tissue, or biological fluid such as blood). For example, a plurality of proteins may contain at least 60%, 75%, 90%, 95%, 99%, 99.9% or more of the total protein mass present in the source from which the plurality of proteins was derived. Alternatively or additionally, a plurality of proteins may contain at most 99.9%, 99%, 95%, 90%, 75%, 60% or less of the total protein mass present in the source from which the plurality of proteins was derived.

A plurality of proteins can be characterized in terms of total number of protein molecules. The total number of protein molecules in a *Saccharomyces cerevisiae* cell has been estimated to be about 42 million protein molecules. See Ho et al., *Cell Systems* (2018); DOI: 10.1016/j.cels.2017.12.004, which is incorporated herein by reference. A plurality of proteins used or included in a method, composition or apparatus set forth herein can include at least 1 protein molecule, 10 protein molecules, 100 protein molecules, $1\times10^4$ protein molecules, $1\times10^6$ protein molecules, $1\times10^8$ protein molecules, $1\times10^{10}$ protein molecules, 1 mole ($6.02214076\times10^{23}$ molecules) of protein, 10 moles of protein molecules, 100 moles of protein molecules or more. Alternatively or additionally, a plurality of proteins may contain at most 100 moles of protein molecules, 10 moles of protein molecules, 1 mole of protein molecules, $1\times10^{10}$ protein molecules, $1\times10^8$ protein molecules, $1\times10^6$ protein molecules, $1\times10^4$ protein molecules, 100 protein molecules, 10 protein molecules, 1 protein molecule or less.

A plurality of proteins can be characterized in terms of the variety of full-length primary protein structures in the plurality. For example, the variety of full-length primary protein structures in a plurality of proteins can be equated with the number of different protein-encoding genes in the source for the plurality of proteins. Whether or not the proteins are derived from a known genome or from any genome at all, the variety of full-length primary protein structures can be counted independent of presence or absence of post translational modifications in the proteins. A human proteome is estimated to have about 20,000 different protein-encoding genes in the haplotype genome such that a plurality of proteins derived from a human can include up to about 20,000 different primary protein structures. See Aebersold et al., *Nat. Chem. Biol.* 14:206-214 (2018), which is incorporated herein by reference. Other genomes and proteomes in nature are known to be larger or smaller. A plurality of proteins used or included in a method, composition or apparatus set forth herein can have a complexity of at least 2, 5, 10, 100, $1\times10^3$, $1\times10^4$, $2\times10^4$, $3\times10^4$ or more different full-length primary protein structures. Alternatively or additionally, a plurality of proteins can have a complexity that is at most $3\times10^4$, $2\times10^4$, $1\times10^4$, $1\times10^3$, 100, 10, 5, 2 or fewer different full-length primary protein structures.

In relative terms, a plurality of proteins used or included in a method, composition or apparatus set forth herein may contain at least one representative for at least 60%, 75%, 90%, 95%, 99%, 99.9% or more of the proteins encoded by the genome of a source from which the sample was derived. Alternatively or additionally, a plurality of proteins may contain a representative for at most 99.9%, 99%, 95%, 90%, 75%, 60% or less of the proteins encoded by the genome of a source from which the sample was derived.

A plurality of proteins can be characterized in terms of the variety of primary protein structures in the plurality including transcribed splice variants. The human proteome has been estimated to include about 70,000 different primary protein structures when splice variants are included. See Aebersold et al., *Nat. Chem. Biol.* 14:206-214 (2018), which is incorporated herein by reference. Moreover, the number of the partial-length primary protein structures can increase due to fragmentation that occurs in a sample. A plurality of proteins used or included in a method, composition or apparatus set forth herein can have a complexity of at least 2, 5, 10, 100, $1\times10^3$, $1\times10^4$, $7\times10^4$, $1\times10^5$, $1\times10^6$ or more different primary protein structures. Alternatively or additionally, a plurality of proteins can have a complexity that is at most $1\times10^6$, $1\times10^5$, $7\times10^4$, $1\times10^4$, $1\times10^3$, 100, 10, 5, 2 or fewer different primary protein structures.

A plurality of proteins can be characterized in terms of the variety of protein structures in the plurality including different primary structures and different proteoforms among the primary structures. Different molecular forms of proteins expressed from a given gene are considered to be different proteoforms. Proteoforms can differ, for example, due to differences in primary structure (e.g. shorter or longer amino acid sequences), different arrangement of domains (e.g. transcriptional splice variants), or different post translational modifications (e.g. presence or absence of phosphoryl, glycosyl, acetyl, or ubiquitin moieties). The human proteome is estimated to include hundreds of thousands of proteins when counting the different primary structures and proteoforms. See Aebersold et al., *Nat. Chem. Biol.* 14:206-214 (2018), which is incorporated herein by reference. A plurality of proteins used or included in a method, composition or apparatus set forth herein can have a complexity of at least 2, 5, 10, 100, $1\times10^3$, $1\times10^4$, $1\times10^5$, $1\times10^6$, $5\times10^6$, $1\times10^7$ or more different protein structures. Alternatively or additionally, a plurality of proteins can have a complexity that is at most $1\times10^7$, $5\times10^6$, $1\times10^6$, $1\times10^5$, $1\times10^4$, $1\times10^3$, 100, 10, 5, 2 or fewer different protein structures.

A plurality of proteins can be characterized in terms of the dynamic range for the different protein structures in the sample. The dynamic range can be a measure of the range of abundance for all different protein structures in a plurality of proteins, the range of abundance for all different primary protein structures in a plurality of proteins, the range of abundance for all different full-length primary protein structures in a plurality of proteins, the range of abundance for all different full-length gene products in a plurality of proteins, the range of abundance for all different proteoforms expressed from a given gene, or the range of abundance for any other set of different proteins set forth herein. The dynamic range for all proteins in human plasma is estimated to span more than 10 orders of magnitude from albumin, the most abundant protein, to the rarest proteins that have been measured clinically. See Anderson and Anderson *Mol Cell Proteomics* 1:845-67 (2002), which is incorporated herein by reference. The dynamic range for plurality of proteins set forth herein can be at least 10, 100, $1\times10^3$, $1\times10^4$, $1\times10^6$, $1\times10^8$, $1\times10^{10}$, or more. Alternatively or additionally, the dynamic range for plurality of proteins set forth herein can be at most $1\times10^{10}$, $1\times10^8$, $1\times10^6$, $1\times10^4$, $1\times10^3$, 100, 10 or less.

One or more proteins can optionally be separated or isolated from other components that are also present in a given protein source. For example, one or more proteins can be separated or isolated from other components prior to modifying the protein(s) with functional groups or prior to attaching the protein(s) to particle(s). Other components from which one or more proteins are separated or isolated can include, for example, lipids, nucleic acids, hormones, enzyme cofactors, vitamins, metabolites, microtubules, organelles (e.g. nucleus, mitochondria, chloroplast, endoplasmic reticulum, vesicle, cytoskeleton, vacuole, lysosome, cell membrane, cytosol or Golgi apparatus) or the like. Protein separation can be carried out using methods known in the art such as centrifugation (e.g. to separate membrane fractions from cytosolic fractions), density gradient centrifugation (e.g. to separate different types of organelles or different sized protein complexes), precipitation, affinity capture (e.g. affinity chromatography or solid-phase extraction using immobilized affinity reagents), adsorption, liquid-liquid extraction, solid-phase extraction, chromatography (e.g. affinity chromatography, ion exchange chromatography, reverse phase chromatography, or size exclusion chromatography), electrophoresis (e.g. polyacrylamide gel electrophoresis) or the like. Useful protein separation methods are set forth in Scopes, *Protein Purification Principles and Practice*, Springer; 3rd edition (1993), which is incorporated herein by reference.

Proteins can be modified with functional groups or attached to particles before, during or after performing a separation step set forth above or otherwise known in the art. For example, proteins can be modified with functional groups or attached to particles after lysing the cell from which the proteins were produced, but prior to carrying out one or more of the separation techniques set forth herein. For example, proteins can be modified with functional groups or attached to particles in a crude cell lysate. The crude lysate can contain both soluble components (e.g. cytosolic proteins and other cytosolic components) and insoluble components (e.g. membrane proteins and other membrane components) of one or more cells.

Proteins can be modified with functional groups or attached to particles after separating soluble components of a cell lysate from insoluble components of the cell lysate, for example after centrifugation. Optionally, proteins from a soluble fraction can be modified with functional groups or attached to particles after separation of the soluble fraction from a membrane fraction. In another option, proteins from an insoluble fraction can be modified with functional groups or attached to particles after separation of the insoluble fraction from a cytosolic faction. In either of these options, the modification or attachment reactions can be carried out prior to carrying out one or more further separation techniques set forth herein or known in the art.

A plurality of proteins, whether including cytosolic proteins, membrane proteins or both can be present in a solution having a surfactant. Exemplary surfactants include cationic surfactant, anionic surfactant, non-ionic surfactant, amphoteric surfactant, or a combination thereof. Exemplary surfactants include, but are not limited to, stearic acid, lauric acid, oleic acid, sodium dodecyl sulfate, sodium dodecyl benzene sulfonate, dodecylamine hydrochloride, hexadecyltrimethylammonium bromide, polyethylene oxide, nonylphenyl ethoxylates, Triton X, pentapropylene glycol monododecyl ether, octapropylene glycol monododecyl ether, pentaethylene glycol monododecyl ether, octaethylene glycol monododecyl ether, lauramide monoethylamine, lauramide diethylamine, octyl glucoside, decyl glucoside, lauryl glucoside, Tween 20, Tween 80, n-dodecyl-β-D-maltoside, nonoxynol 9, glycerol monolaurate, polyethoxylated tallow amine, poloxamer, digitonin, zonyl FSO, 2,5-dimethyl-3-hexyne-2,5-diol, Igepal CA630, Aerosol-OT, triethylamine hydrochloride, cetrimonium bromide, benzethonium chloride, octenidine dihydrochloride, cetylpyridinium chloride, adogen, dimethyldioctadecylammonium chloride, CHAPS, CHAPSO, cocamidopropyl betaine, amidosulfobetaine-16, lauryl-N,N-(dimethylammonio)butyrate, lauryl-N,N-(dimethyl)-glycinebetaine, hexadecyl phosphocholine, lauryldimethylamine N-oxide, lauryl-N,N-(dimethyl)-propanesulfonate, 3-(1-pyridinio)-1-propanesulfonate, 3-(4-tert-butyl-1-pyridinio)-1-propanesulfonate, dodecanoyl-N-methylglycine sodium, and combinations thereof.

Proteins can be modified with functional groups or attached to particles in the presence of one or more different surfactants. Alternatively, proteins can be separated from surfactants prior to being modified with functional groups or attached to particles. Proteins, whether non-functionalized, functionalized, non-attached to particles or attached to particles, can be separated from surfactant using a method set forth herein or known in the art. Optionally, the proteins can then be subjected to one or more steps of a method set forth herein such as attachment to particles, attachment to a solid support (for example, via a particle to which the protein is attached), or detection in a method set forth herein.

In some configurations of a method set forth herein, proteins can be modified with functional groups or attached to particles after separating the proteins from genomic DNA or other nucleic acids. For example, proteins can be separated from nucleic acids via precipitation, liquid-liquid extraction or solid-phase extraction. Optionally, the modification or attachment reactions can. Be carried out prior to sub-fractionating different proteins from each other, for example, using a separation technique set forth herein or known in the art. Separation of proteins from native nucleic acids can be beneficial, for example, when SNAPs or other nucleic acids are to be used as particles for attachment of the proteins. In this case, removal of other DNA species can allow the particle-attached proteins to be uniquely manipulated by exploiting separation characteristics of the nucleic acid particles.

Optionally, proteins can be modified with functional groups or attached to particles after the proteins have been separated from relatively small molecules that contain, or are suspected of containing, reactive groups that will interfere with functionalization of the proteins or attachment of the proteins to particles. For example, lipids, amino acids and peptide fragments of larger proteins may have amino moieties, sulfur moieties or other moieties that cross-react to form unwanted products, or that inhibit production of desired products, in methods set forth herein. Other contaminants can include reagents added to a proteins sample for a previous manipulation such as protease inhibitors, reactants for functionalization of the proteins, surfactants or cell lysis agents. A size-based separation technique can be used to separate proteins from contaminants having lower molecular weight, such techniques including, for example, filtration, dialysis, size exclusion chromatography or precipitation. In some configurations, separation of proteins from smaller molecules can utilize a technique or material having a molecular weight cutoff that is equal to or less than 10 kDa, 8 kDa, 6 kDa, 4 kDa, 3 kDa, 2 kDa, 1 kDa or less. A separation technique can be configured to separate proteins from peptides that are shorter than about 50, 25, 10 or 5 amino acids in length can be used. Proteins of interest can be precipitated away from small molecules in solution, for example, using organic solvent induced precipitation, salt induced precipitation (e.g. using ammonium sulfate) or isoelectric precipitation (e.g. using trichloroacetic acid). Proteins of interest can be separated from small molecules using other techniques known in the art such as liquid-liquid extraction or solid-phase extraction. Soli-phase extraction can employ, for example, SP3 Carboxy beads, such as Sera-Mag Carboxylate-Modified Magnetic Beads or Speed-Beads (GE Life Sciences), magnetic multi-mode HILIC microparticles MagReSyn HILIC (ReSyn Biosciences) or S-Trap Mini Spin Columns (ProtiFi). Other useful materials for separating proteins from other contaminants include cationic polymers, for example, in the form of nanoparticles. Exemplary cationic polymers include polycation homopolymers, copolymers containing a polycation block or cationic polymers set forth in Blume et al, *Nature Communications* 11:3662 (2020), U.S. Pat. No. 10,022,334 or US Pat. App. Pub. No. 2020/0206145 A1, each of which is incorporated herein by reference.

When performing one or more steps of a method set forth herein, proteins can be in a native state, for example, being capable of performing native function(s) such as catalysis of reactions. Native state proteins can also include multiple subunits, each subunit composed of a single chain of amino acids. As such a native state protein can include at least 2, 3, 4, 5 or more amino acid chains. Alternatively, proteins can be in a denatured state, for example, being incapable of performing native function(s) such as catalysis of reactions. In some situations, denatured proteins can include multiple amino acid chains, for example, due to covalent linkages between amino acid chains or due to molecular tangling.

Proteins, whether denatured or native-state, can be treated to remove covalent linkages between amino acid chains or to inhibit molecular tangling. For example, proteins can be reduced to break disulfide bonds between amino acid chains. Cysteines that may otherwise reform the disulfide bonds or form new disulfide bonds can be functionalized, for example, via alkylation or reaction with methyl tetrazine. An exemplary protocol for reduction and alkylation of a protein sample can include steps of (i) lysing cells or tissue in trifluoroacetic acid (cell pellet/tissue:TFA::1:4-1:8 (v/v), incubated for 2 to 10 min. at room temperature), (ii) adding neutralization buffer (2M TrisBase in water, added to 10× the volume of TFA in step (i)) to the lysis mixture, and (iii) adding reduction/alkylation buffer (10 mM Tris(2-carboxyethyl)phosphine (TCEP, 2.9 mg/mL), 40 mM 2-Chloroacetamide (CAA, 3.7 mg/mL) in water, added to 1.1× the volume of TFA in step (i) and incubated at 95° C. for 5 min.). See for example, Rappsilber et al., Nat. Protoc. 2:1896-906 (2007), which is incorporated herein by reference.

In alternative configurations, disulfide linkages in proteins need not be reduced, for example, instead being stabilized to maintain attachment between two amino acid chains. Disulfide linkages can be stabilized, for example, via reaction with a dibromomaleimide (e.g. 2,3-dibromomaleimide) to form maleamic acid linkages.

One or more proteins can be in a native state for some manipulations and in a denatured state for other manipulations. Protein(s) may be denatured at any stage during manipulation, including for example, upon lysis of the cell from which the protein is derived or otherwise upon removal of a protein from its native milieu. In some cases, denaturation occurs at a later stage of processing such as a stage where protein(s) are separated from other cellular components, fractionated from other proteins, functionalized for attachment to a particle, attached to a particle, contacted with an affinity reagent, detected, or other step set forth herein. Denatured proteins may be refolded, for example, reverting to a native state for one or more step of a process set forth herein. Similarly, proteins that are present in a composition or apparatus set forth herein can be in a native or denatured state.

A method of the present disclosure can further include a step of modifying one or more proteins to incorporate reactive moieties. The reactive moieties can be configured to participate in subsequent attachment reactions, such as reactions for attaching the modified protein to a particle or solid support. In particular configurations of the methods set forth herein, a plurality of proteins is treated with a molar excess of reagents that will be added as reactive moieties to the proteins. Moreover, individual proteins in the reaction may each contain more than one amino acid residue that is reactive with the reagents. As such, individual modified proteins produced by the reaction can contain more than one reactive moiety. For example, modified proteins produced in a method set forth herein may have at least 2, 3, 4, 5, 10, 25 or more reactive moieties. Alternatively or additionally, modified proteins produced in a method set forth herein may have at most 25, 10, 5, 4, 3, 2 or fewer reactive moieties. The foregoing ranges can pertain to absolute numbers of reactive moieties for individual proteins or to average numbers of reactive moieties for a plurality of proteins in a given sample. In some configurations of a method set forth herein, individual proteins each have only a single reactive moiety (i.e. one and only one reactive moiety per protein). Some proteins may resist modification in a reaction set forth herein, for example, due to absence of an appropriately reactive amino acid or due to inaccessibility of the reagents to reactive amino acids in the structure of the protein.

A plurality of proteins that is modified in a method set forth herein can be homogenous with respect to particular characteristics such as primary structure, isoform (e.g. presence of post-translational modifications, proteolytic isoforms, products of alternatively spliced mRNA etc.) or other characteristics set forth herein for protein samples. Alternatively, a plurality of proteins can be heterogeneous with respect to particular characteristics. As such, different proteins can be present in a plurality of proteins that is modified in a method set forth herein. For example, the plurality of proteins can include some or all proteins of a proteome for a given cell or other biological source. A protein sample can be separated from other cellular components prior to reaction, for example, using methods set forth herein. Optionally, a plurality of proteins can be in a pool and the protein pool can be reacted with reagents that will be added as reactive moieties to the proteins. However, proteins can be sub-fractionated to different degrees prior to being reacted with reagents that will be added as reactive moieties to the proteins.

A method of the present disclosure can further include a step of producing particles having reactive moieties. The reactive moieties can be configured to participate in subsequent attachment reactions, such as reactions for attaching the particle to a protein (or other analyte) or solid support. In some cases, reactive moieties are endogenous to a particle, for example, being a product of a reaction that forms the particle. Alternatively, exogenous reactive moieties can be added to a particle, for example after the particle has been formed. In some configurations, individual particles each have only a single reactive moiety (i.e. one and only one reactive moiety per particle). Alternatively, a particle can have multiple reactive moieties. For example, a particle may have at least 2, 3, 4, 5, 10, 25 or more reactive moieties. Alternatively or additionally, a particle may have at most 25, 10, 5, 4, 3, 2 or fewer reactive moieties. Multiple reactive moieties of a particle can be the same type as each other or at least some of the reactive moieties can differ from each other.

A protein or particle can be modified to incorporate a reactive moiety that will in turn participate in a subsequent attachment reaction, such as a reaction for attaching a particle to a protein, a reaction for attaching a particle to a solid support or a reaction for attaching a protein to a solid support. Functionalizing one or both of such reaction partners may improve the efficiency or speed of subsequent attachment between the partners. For example, a sulfhydryl group (—SH) or amine (—NH2) of a protein or particle may be functionalized to allow for greater reactivity or efficiency of an attachment reaction. Exemplary functionalization chemistries are set forth below. For example, a reaction set forth below can be used to attach a reactive moiety to a particle, and R and R' may represent the particle or the reactive moiety. In other cases, a reaction set forth below can be used to attach a reactive moiety to a protein, and R and R' may represent the protein or the reactive moiety. Similarly, a reaction set forth below can be used to attach a reactive moiety to a solid support and, R and R' may represent the solid support or the reactive moiety. It will be understood that the reactions set forth below can be used to attach a particle to a protein and R and R' may represent the protein or the particle.

Amine moieties can be functionalized to attach a reactive moiety or other moiety. In some cases, an isothiocyanate moiety may react with nucleophiles such as amines, sulfhydryls, the phenolate ion of tyrosine side chains or other molecules to form a thiourea linkage.

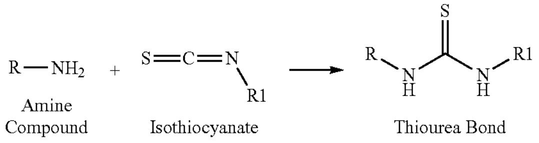

An isocyanate moiety can react with an amine to form a stable urea linkage.

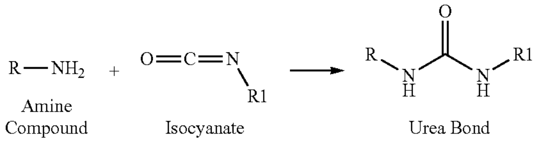

An acyl azide can react with a primary amine to form an amide linkage.

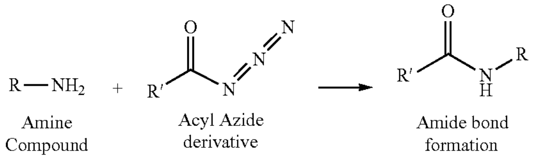

An N-hydroxysuccinimide (NHS) ester can react with an amine to form an amide linkage.

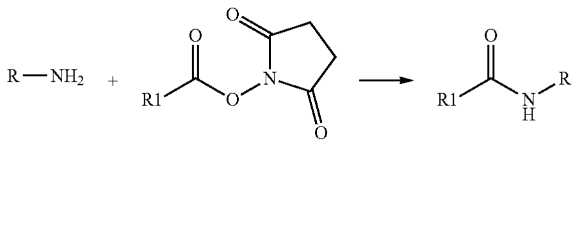

A sulfonyl chloride can react with a primary amine to form a sulfonamide linkage.

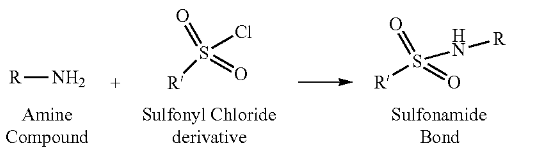

Carbonyl moieties such as aldehydes, ketones, and glyoxals can react with amines to form Schiff base intermediates and the addition of sodium borohydride or sodium cyanoborohydride can reduce the Schiff base intermediate to form a secondary amine linkage.

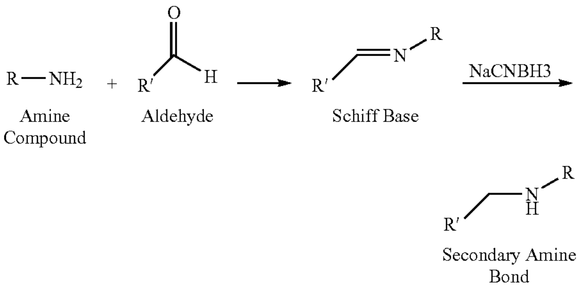

An epoxide or oxirane moiety can react with a nucleophile in a ring-opening process. The reaction can take place with primary amines, sulfhydryls, or hydroxyl groups to create secondary amine, thioether, or ether bonds, respectively.

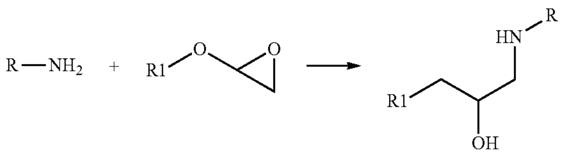

A carbonate can react with nucleophiles such as amines to form a carbamate linkage.

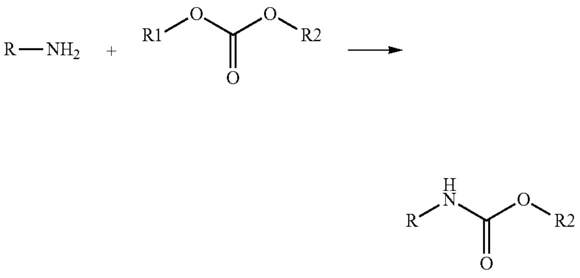

An aryl halide, such as fluorobenzene derivative, can react with an amine to form an arylamine linkage. Other nucleophiles such as thiol, imidazolyl, and phenolate groups can also react with an aryl halide to form a stable linkage.

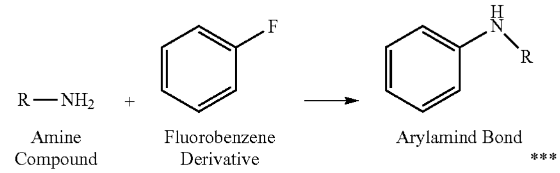

***

An amine can react with an imidoester to form an amidine linkage.

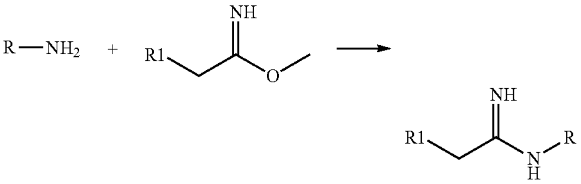

A carbodiimide can be used as a zero-length crosslinking agents to mediate formation of an amide or phosphoramidate linkage between a carboxylate group and an amine, or between a phosphate and an amine, respectively. Carbodiimides are zero-length reagents because in forming these bonds no additional chemical structure is introduced between the conjugating molecules. A carbodiimide can be used to activate a phosphate to an intermediate phosphate ester that in turn reacts with an amine to form a phosphoramidate linkage.

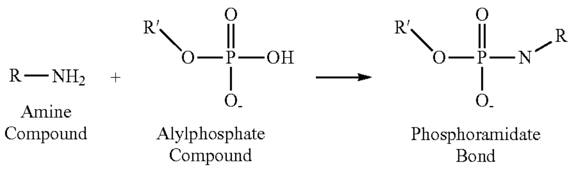

Squarates and cyanomethyl acyl sulfonamides, such as those set forth in Abbasov et al., *Nature Chemistry* 13: 1081-1092 (2021), which is incorporated herein by reference, can be used to modify amino moieties on lysines.

In some cases, a thiol may be functionalized or modified. For example, the thiol group of cysteine is the most nucleophilic functional group found among the 20 proteinogenic amino acids. Through careful control of pH, selective modification over other nucleophilic amino acid residues such as lysine can be readily achieved. Moreover, thiol modification of oligonucleotides may be used to enable derivatization. In some cases, the unique nucleophilicity of thiols can be exploited for selective reaction with a number of alternative electrophiles, which allow efficient and selective attachment to be achieved. For example, one such group includes α-halocarbonyls, with iodoacetamide based reagents finding particular utility. Higher thiol selectivity may be achieved using less electrophilic bromo- and even chloro-derivatives, though reactivity is also reduced. Methylsulfonyl heteroaromatic derivatives can also be used for thiol-specific conjugation. In other cases, alternative thiol-functional groups, such as disulfide-bridging pyridazinediones, carbonylacrylic reagents, and cyclopropenyl ketones may be utilized for bioconjugation.

Three forms of activated halogen derivatives that can be used for functionalization of sulfhydryls include haloacetyl, benzyl halides, and alkyl halides. In each of these compounds, the halogen group may be easily displaced by an attacking nucleophilic substance to form an alkylated derivative with loss of HX (where X is the halogen and the hydrogen comes from the nucleophile).

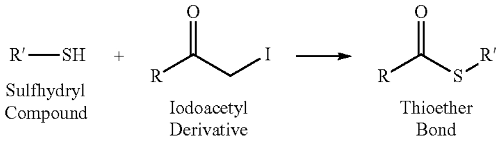

The double bond of a maleimide can undergo an alkylation reaction with a sulfhydryl to form a thioether linkage.

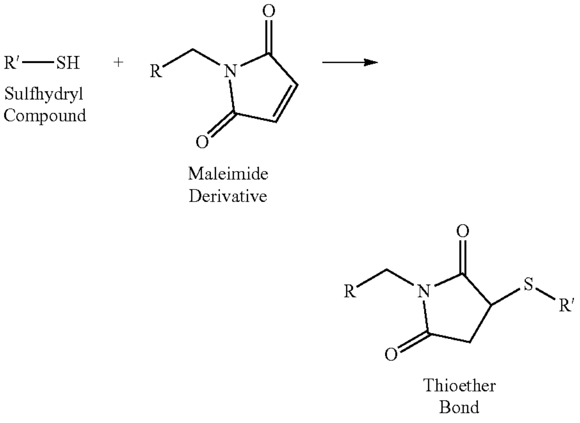

A sulfhydryl can react with an aziridine to form a thioether bond.

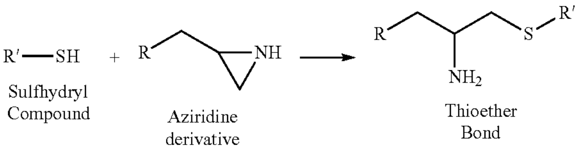

An acryloyl can be reacted with a sulfhydryl to create a thioether linkage.

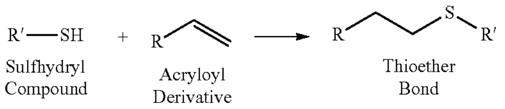

Although aryl halides are commonly used to modify amine-containing molecules to form aryl amine derivatives, they also may react quite readily with sulfhydryl groups. For example, a fluorobenzene can react with a sufhydryl to form an aryl thioether linkage. Conjugates formed with sulfhydryl groups are reversible by cleaving with an excess of thiol (such as DTT).

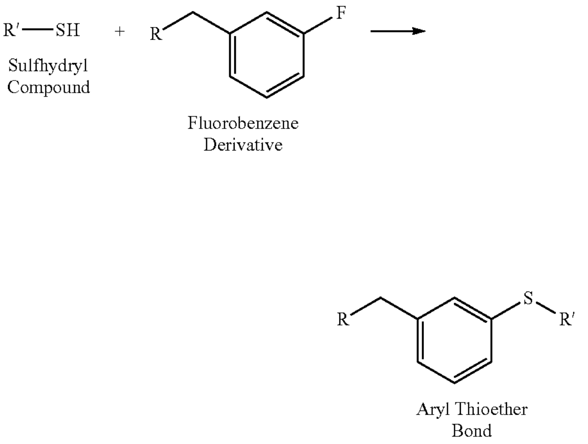

A vinyl sulfone can be reacted with a sulfhydryl to form a beta-thiosulfonyl linkage.

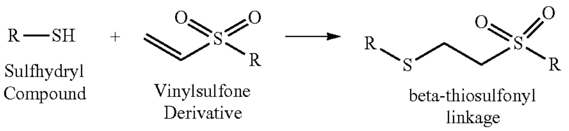

Compounds containing a disulfide group can participate in a disulfide exchange reaction with another thiol.

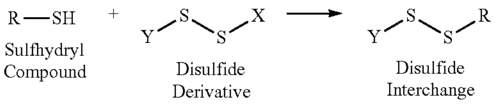

For example, a pyridyl dithiol can undergo an interchange reaction with a free sulfhydryl to yield a single mixed disulfide product.

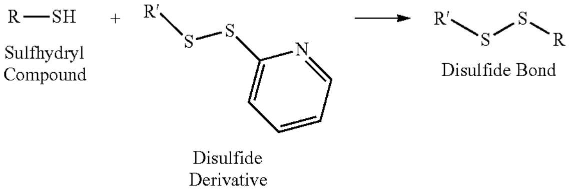

In another example, sulfhydryl groups activated with the leaving group 5-thio-2-nitrobenzoic acid can be used to couple free thiols by disulfide interchange. The disulfide of Ellman's reagent can undergo disulfide exchange with a free sulfhydryl to form a mixed disulfide with concomitant release of one molecule of the chromogenic substance 5-sulfido-2-nitroben-zoate, also called 5-thio-2-nitrobenzoic acid (TNB). The TNB-thiol group can again undergo interchange with a sulfhydryl to yield a disulfide crosslink. Upon coupling with a sulfhydryl compound, the TNB group is released.

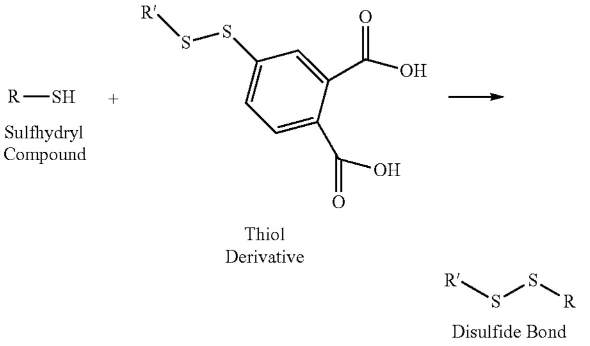

Sulfhydryl Compound

Thiol Derivative

Disulfide Bond

In some cases, disulfide reduction may be performed using thiol-containing compounds such as TCEP, DTT, 2-mercaptoethanol, or 2-mercaptoethylamine. Dinitroimidazoles, such as 1,4-dinitorimidazoles can react with cysteine under acidic to neutral conditions to form a (4-nitroimidazole)-thiol product. See, for example, Luo et al., *Nat. Comm.* 10:142 (2019), which is incorporated herein by reference.

Optionally, a carboxylate may be utilized for functionalization or modification of a protein, particle or other substance. For example, N,N'-Carbonyl diimidazole (CDI) can react with carboxylic acids under nonaqueous conditions to form N-acylimidazoles of high reactivity. An active carboxylate can then react with amines to form amide bonds or with hydroxyl groups to form ester linkages.

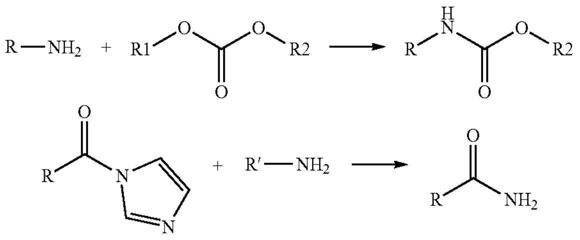

In some cases, carbodiimides function as zero-length crosslinking agents capable of activating a carboxylate group for coupling with an amine-containing compound for attachment. Carbodiimides can be used to mediate the formation of amide or phosphoramidate linkages between a carboxylate and an amine or a phosphate and an amine. N,N'-Disuccinimidyl carbonate (DSC) is highly reactive toward nucleophiles. In aqueous solutions, DSC can be hydrolyzed to form two molecules of N-hydroxysuccinimide (NHS) with release of one molecule of $CO_2$. In non-aqueous environments, the reagent can be used to activate a hydroxyl group to a succinimidyl carbonate derivative. DSC-activated hydroxylic compounds can be used to conjugate with amine-containing molecules to form stable crosslinked products.

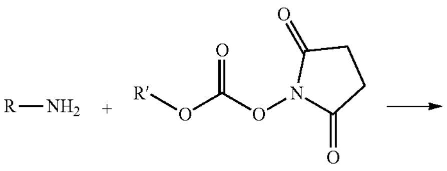

-continued

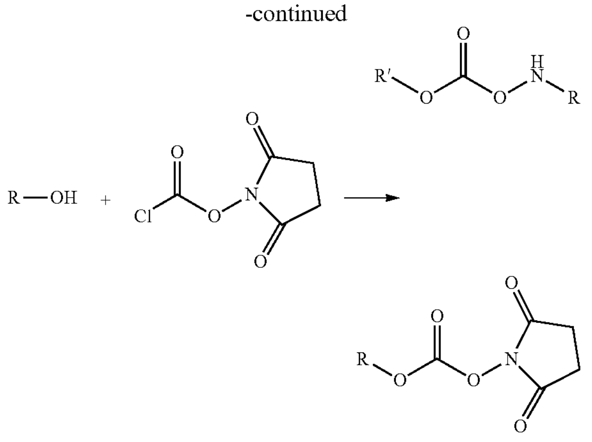

In some cases, sodium periodate can be used to oxidize hydroxyl groups on adjacent carbon atoms, forming reactive aldehyde moieties suitable for coupling with amine- or hydrazide-containing molecules for conjugation. Optionally, reactive alkyl halogen compounds can be used to specifically modify hydroxyl groups for attachment.

In some cases, modification reagents can add a receptor or ligand moiety to a protein, particle or other substance set forth herein. For example, amines, carboxylates, sulfhydryls, carbohydrate groups and other reactive sites can be functionalized with a biotin or (strept)avidin moiety. In some cases, photoreactive biotinylation reagents are used to add a biotin group to a particle or protein, for example, when not containing convenient functional groups for modification. Alternatively, a linkage set forth above can be used. For example, carboxylate-containing biotin compounds can be coupled to amines via a carbodiimide-mediated reaction using EDC. In some cases, NHS-iminobiotin can be used to label amine-containing molecules with an iminobiotin moiety. In some cases, Sulfo-NHS-SS-biotin (also known as NHS-SS-biotin) can be used to modify amine-containing proteins, particles or other substances. In some cases, 1-biotinamido-4-[4'-(maleimidomethyl) cyclohexane-carboxamido]butane reacts with sulfhydryls to form stable thioether linkages. In some cases, N-[6-(biotinamido)hexyl]-3'-(2'-pyridyldithio)propionamide, where the reagent contains a 1,6-diaminohexane spacer group which is attached to biotin's valeric acid side chain, may be modified at the terminal amino group of the spacer via an amide linkage with the acid precursor of SPDP to create a terminal, sulfhydryl-reactive group. The pyridyl disulfide end of biotin-HPDP may react with free thiol groups to form a disulfide bond with loss of pyridine-2-thione.

Protein modifications set forth herein can be performed in complex samples, including for example, samples having some or all of a proteome. Conditions can be deployed to achieve selective modification of a given type of amino acid. For example, IA-alkyne or EBX2-alkyne can be used to selectively modify cysteines; 2,3 STP-alkyne, ArSq-alkyne or EBA-alkyne can be used to selectively modify lysines; SuTEx2-alkyne or PTAD-alkyne can be used to selectively modify tyrosines; MeTet-alkyne, HC-alkyne or Az-alkyne can be used to selectively modify aspartates and glutamates; CP-alkyne, HMN-alkyne, or MMP-alkyne can be used to selectively modify tryptophans; CP-alkyne can be used to selectively modify histidines, and PhGO-alkyne can be used to selectively modify arginines within a proteome sample, for example, as set forth in Zanon et al., 10.33774/chemrxiv-2021-w7rss-v2 (2021), which is incorporated herein by reference.

A protein may be attached to a particle by a covalent bond or a non-covalent bond. The attachment can occur between a reactive moiety on the protein and a reactive moiety on the particle. The reactive moiety on the protein can be endogenous to the protein, for example, being a reactive moiety of an amino acid side chain group. Alternatively, the reactive moiety can be exogenous to the protein, for example, being produced by functionalization of the protein. Similarly, the reactive moiety on the particle can be endogenous to the structure of the particle or an exogenous moiety that is a modification or addition to the composition of the particle. Reactive moieties on a protein or particle can participate in forming a covalent or non-covalent bond between a particle and protein. Exemplary reactive moieties and attachment configurations include, but are not limited to those set forth above in the context of functionalizing proteins or those set forth below. Also, set forth below are methods and compositions for modifying proteins or particles to include reactive moieties for use in various attachment configurations.

Any of a variety of covalent or non-covalent chemistries can be used to attach a protein to a particle. Attachment of a protein to a particle can employ chemical conjugation, bioconjugation, enzymatic conjugation, photo-conjugation, thermal-conjugation, or a combination thereof (Spicer et. al., *Chemical Reviews,* 118:7702-7743 (2018), or Hermanson, "Bioconjugate Techniques", Academic Press; 3$^{rd}$ Edition, 2013, each of which is incorporated herein by reference). Chemistries and methods set forth herein in the context of attaching proteins to particles can also be used to functionalize proteins to incorporate reactive moieties, functionalize particles to incorporate reactive moieties, or attach particles to other substances such as surfaces, solid supports, sites of an array, or other particles. Optionally, chemistries used in one step of a method set forth herein are orthogonal to chemistries used for other steps. For example, chemistry used to attach proteins to particles can be orthogonal to chemistries used to functionalize the proteins, functionalize the particles and/or attach the particles to a solid support.

Bioorthogonal chemistries can facilitate selective modification of proteins or selective attachment of proteins to particles in complex biological milieus, for example, to prevent non-protein molecules from attaching to particles or quenching desired reactions. However, bioorthogonal chemistries need not be deployed in a method set forth herein, for example, when proteins are separated from their native milieu or isolated from other biological components. Accordingly, a wide range of other chemistries can be used. In some cases, proteins can be modified or attached to particles in non-aqueous solvents, for example, in situations where the proteins need not be in a native state.

A protein can be attached to a particle using a bioorthogonal reaction or click chemistry (see, for example, U.S. Pat. Nos. 6,737,236 and 7,427,678, each of which is incorporated herein by reference); azide alkyne Huisgen cycloaddition reactions, which use a copper catalyst (see, for example, U.S. Pat. Nos. 7,375,234 and 7,763,736, each of which is incorporated herein by reference); Copper-free Huisgen reactions ("metal-free click") using strained alkynes or triazine-hydrazine moieties which can link to aldehyde moieties (see, for example, U.S. Pat. No. 7,259,258, which is incorporated herein by reference); triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties (see, for example, WO 2005/065814, which is incorporated herein by reference). A functional group may be configured to react via a click reaction (e.g., metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norbornene cycloaddition, oxanobornadiene cycloaddition, tetrazine ligation, tetrazole photoclick reactions). Exemplary silane-derivative click reactants may include alkenes, alkynes, azides, epoxides, amines, thiols, nitrones, isonitriles, isocyanides, aziridines, activated esters, and tetrazines (e.g., dibenzocyclooctyne-azide, methyltetrazine-transcyclooctylene, epoxide-thiol, etc.). A click reaction can provide an advantageous method of rapidly forming a bond under biologically conducive conditions (e.g., room temperature, aqueous solvents).

Copper-Catalyzed Azide-Alkyne Cycloadditions (CuAAC) can be utilized for attachment of two substances, such as attachment of a particle to a protein. In some cases, the (3+2) cycloaddition between an azide and alkyne can yield a mixture of two triazole isomers. To achieve conjugation via CuAAC, a copper(I) catalyst can either be added directly, or generated in situ by reduction of an initial copper(II) complex, for example, using ascorbic acid.

Strain-Promoted Azide-Alkyne Cycloadditions (SPAAC) may be utilized for attachment of two substances, such as attachment of a particle to a protein. Highly strained cyclooctynes can react with azides to form triazoles. In some cases, supramolecular host-guest interactions can also be used to promote azide-alkyne cycloaddition.

Inverse-electron demand Diels-Alder reactions (IEDDA) may be utilized for attachment of two substances, such as attachment of a particle to a protein. For example, an IEDDA reaction between 1,2,4,5-tetrazines and strained alkenes or alkynes may be employed. Useful reactive moieties include, for example, strained trans-cyclooctenes, functionalized norbornene derivatives, triazines, or spirohexene. In some cases, hetero-Diels-Alder cycloaddition of maleimides and furans may be utilized for attachment. A particularly useful reaction occurs between methyltetrazine (mTz) and transcyclooctene to yield a dihydropyridazine linkage, which may isomerize to a corresponding 1,4-dihydro-isomers or be oxidized to give a pyridazine product. In some cases, oxime and hydrazone may be utilized for attachment of two substances, such as attachment of a particle to a protein. For example, attachment via hydrazone formation can be achieved via difunctional crosslinking.

In some cases, a Diels-Alder reaction can involve covalent coupling of a diene with an alkene to form a six-membered ring.

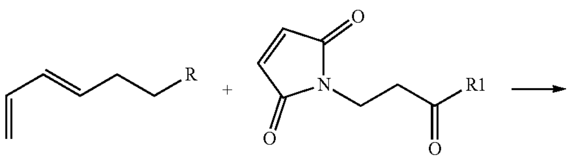

-continued

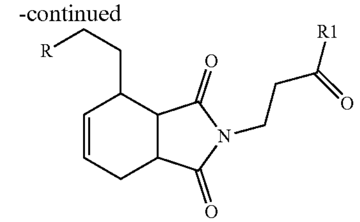

In some cases, transition metal complexes may be utilized for attachment of two substances, such as attachment of a particle to a protein. The nature of late transition metals may make a transition metal complex well suited to the manipulation of unsaturated and polarizable functional groups (olefins, alkynes, aryl iodides, arylboronic acids, etc.). For example, a Pd(0)-catalyst can be used to mediate allyl carbamate deprotections or Suzuki-Miyaura cross-coupling. In other examples, a ruthenium catalyst may be used. For example, with ruthenium complexes, S-allylcysteine can be introduced into proteins by a variety of methods, including conjugate addition of allyl thiol to dehydroalanine, direct allylation of cysteine, desulfurization of allyl disulfide, or metabolic incorporation as a methionine surrogate in methionine auxotrophic *E. coli.*

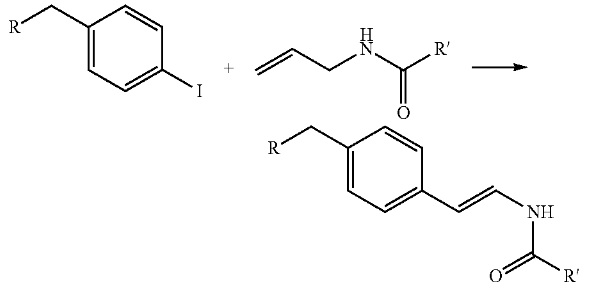

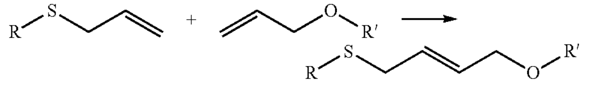

In some cases, complex formation with boronic acid derivatives may be used for attachment of substances, such as attachment of a particle to a protein. For example, boronic acid derivatives are able to form ring structures with other molecules having neighboring functional groups consisting of 1,2- or 1,3-diols, 1,2- or 1,3-hydroxy acids, 1,2- or 1,3-hydroxylamines, 1-2- or 1,3-hydroxyamides, 1,2- or 1,3-hydroxyoximes, as well as various sugars or biomolecules containing these species.

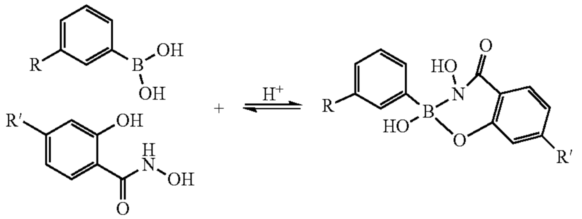

In some cases, enzyme-mediated conjugation may be utilized to attach substances, such as attachment of a particle to a protein. Enzyme-mediated conjugation may proceed via transglutaminases, peroxidases, sortase, SpyTag-SpyCatcher, or a combination thereof. Photo conjugation and activation may proceed via photoacrylate crosslinking reaction, photo thiol-ene reaction, photo thiol-yne reaction, or a combination thereof. In some cases, attachment or conjugation may proceed via noncovalent interactions, these may be through self-assembling peptides, binding sequences, host-guest chemistry, complementary hybridization of nucleic acids, or a combination thereof.

A protein can be attached to a particle by a receptor-ligand binding interaction. For example, binding of (strept)avidin to the small molecule biotin may be used. (Strept)avidin may be attached to a first substance, such as a particle, and biotin may be attached to a second substance, such as a protein, thereby allowing the substances to become attached via binding of the (strept)avidin to the biotin. Other receptor ligand pairs that can be used instead of (strept)avidin-biotin include, but are not limited to, antibodies and their epitopes, aptamers and their epitopes, complementary nucleic acid molecules, lectins and carbohydrates, or nucleic acids and nucleic acid binding proteins. Further examples of useful receptor-ligand pairs include probes set forth herein and the targets to which they bind. A protein, particle or other substance set forth herein can be functionalized to include a receptor moiety or ligand moiety, for example, using functionalization chemistries set forth herein.

A particle of the present disclosure can be convertible between two or more different states. The different states can facilitate different manipulations or uses for the particle. For example, a first state can facilitate attachment of a protein to the particle and a second state may facilitate subsequent manipulation or detection of the protein that is attached to the particle. In some cases, the two different states provide mutually exclusive functions. For example, a first state can facilitate attachment of a given particle to a single protein and can inhibit the given particle from contacting, much less attaching to, a protein that is already attached to another particle. However, a second state for the given particle may allow it to contact, or attach to, a protein that is already attached to another particle. As such, the second state may lack the inhibitory function of the first state. Continuing with this example, a second state of the given particle may facilitate interaction of an attached protein with an affinity reagent or other reagent used for detection or manipulation of the protein. However, the first state of the given particle may inhibit interaction of an attached protein with the affinity reagent or other reagent.

A particle of the present disclosure can be configured to be in a first state that facilitates attachment of an individual protein to a single particle even in a reaction where the protein has multiple moieties that are reactive with particles and is in contact with multiple particles. A plurality of particles in the first state can be reacted with a plurality of proteins to yield a plurality of protein-attached particles, wherein each protein-attached particle is composed of a single protein attached to a single particle. The particle component of each particle-protein conjugate can be converted to a second state to facilitate detection or manipulation of the respective protein component. For example, the second state can facilitate binding of the particle-attached protein to an affinity reagent, reaction of the particle-attached protein with a modifying reagent, or detection of endogenous or exogenous label(s) on the particle-attached protein.

Optionally, a particle in a first state can be attached to a protein or protein-reactive moiety via a single stranded nucleic acid linker. The linker can optionally be in a double stranded form in a second state of the particle. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state wherein a single stranded nucleic acid linker attaches each of the particles to a second reactive moiety; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) hybridizing an oligonucleotide to the single stranded nucleic acid linker, thereby converting the nucleic acid linker from a single stranded conformation to a double stranded conformation.

FIG. 1 illustrates a method for attaching a protein to a particle via a single-stranded nucleic acid linker. In a first step, particles (rounded rectangles) attached to first reactive moieties ($R_1$) via a single stranded nucleic acid linker (spiral) are reacted with a protein (globule) having a plurality of second reactive moieties ($R_2$). The first reactive moiety of a particle reacts with a second reactive moiety of the protein to form a bond, thereby attaching the protein to one of the particles. The single stranded nucleic acid linker constrains the protein from contacting or attaching to a second particle despite the protein having second reactive moieties that are unreacted. In a second step, the products of the first reaction are treated with a quenching agent having an optional ligand (triangle) and the second reactive moiety. The second reaction quenches any first reactive moieties remaining on particles. The quenching agent is inert to the protein. The ligand, if present, can be used to separate quenched particles from protein-attached particles, for example, using an immobilized receptor in a solid-phase extraction or affinity chromatography process (not shown). Optionally, unreacted proteins can be separated from unreacted particles between the first and second step. In an alternative option, the quenching agent can be added to a mixture of unreacted proteins and unreacted particles. In the third step of FIG. 1, the single-stranded nucleic acid linker is hybridized to a complementary oligonucleotide, thereby changing the conformation of the linker from a constrained state to the more extended state of a double stranded nucleic acid linker (ladder). As such, the protein is more accessible to binding other reagents (e.g. affinity reagents, chemical reagents, enzymes, or the like) than when attached to the particle via a single-stranded nucleic acid linker. In the reaction shown, both the protein and ligand are attached to respective particles via the double stranded nucleic acid linker. Accordingly, the ligand can also be more accessible to receptors and other reagents when attached to the double stranded linker compared to the single stranded linker. Quenching and/or separation of particles can occur after the linker has been converted from single-stranded to double-stranded form. In some cases, quenching and/or separation of particles can occur prior to converting the linker from single-stranded to double-stranded form.

The configuration exemplified in FIG. 1, utilizes a single-stranded nucleic acid linker to constrain the particle-attached protein from reacting with a second particle. The linker can have a nucleic acid sequence that takes on a compact secondary or tertiary structure, thereby retaining the protein in close proximity to the surface of the particle. The close proximity can create steric hindrance that prevents unreacted second reaction moieties on the particle-attached protein from contacting unreacted first reaction moieties on a second particle. The hindrance need not be solely steric, nor steric at all. For example, the particles can have similarly charged surfaces such that the particles are inhibited from coming within close enough proximity for the single-stranded nucleic acid linkers of two particles to contact the same protein at the same time. For example, individual nucleic acid origami particles can each be configured to have a single-stranded linker attached to a surface that is negatively charged due to the positioning of the phosphates in the nucleic acid backbone of the scaffold and/or staples of the origami.

In an alternative configuration, the particles exemplified in FIG. 1 can include a surface that retains the linker in close proximity. For example, a single-stranded nucleic acid linker will have a negatively charged backbone that is attractive to a positively charged surface. In some configurations, for example when using a structured nucleic acid particle or other particle having nucleic acid components, the nucleic acid linker can be hybridized, via Watson-Crick complementarity, to a complementary sequence in or on the particle. For example, a nucleic acid origami particle can include a sequence in a scaffold and/or staple that is complementary to at least a region of the single stranded linker. This can result in the attached protein being restrained in close proximity to the surface of the particle, thereby preventing unreacted second reaction moieties on the protein from contacting unreacted first reaction moieties on a second particle. Steric hindrance and/or charge repulsion can play a role in preventing two particles from attaching to the same protein, for example, as set forth above.

Accordingly, a particle in a first state can be attached to a protein or protein-reactive moiety via a nucleic acid linker that is hybridized to a surface of the particle. The linker can optionally be dehybridized from the particle surface in a second conformation of the particle. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a nucleic acid linker attaches the second reactive moiety to each of the particles, and wherein the nucleic acid linker is hybridized to a surface of the particle; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) dehybridizing the nucleic acid linker from the surface of the particle and hybridizing an oligonucleotide to the single stranded nucleic acid linker, thereby converting the nucleic acid linker to an extended conformation.

Optionally, a particle in a first state can be attached to a protein or protein-reactive moiety via a nucleic acid linker having a region of internal complementarity (i.e. self complementarity). The linker can optionally be hybridized to a second nucleic acid in a second conformation of the particle. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a nucleic acid linker attaches the second reactive moiety to each of the particles, and wherein the nucleic acid linker has a region of internal complementarity; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) dehybridizing the region of internal complementarity and hybridizing an oligonucleotide to the single stranded nucleic acid linker, thereby converting the nucleic acid linker to an extended conformation.

Figure 2:
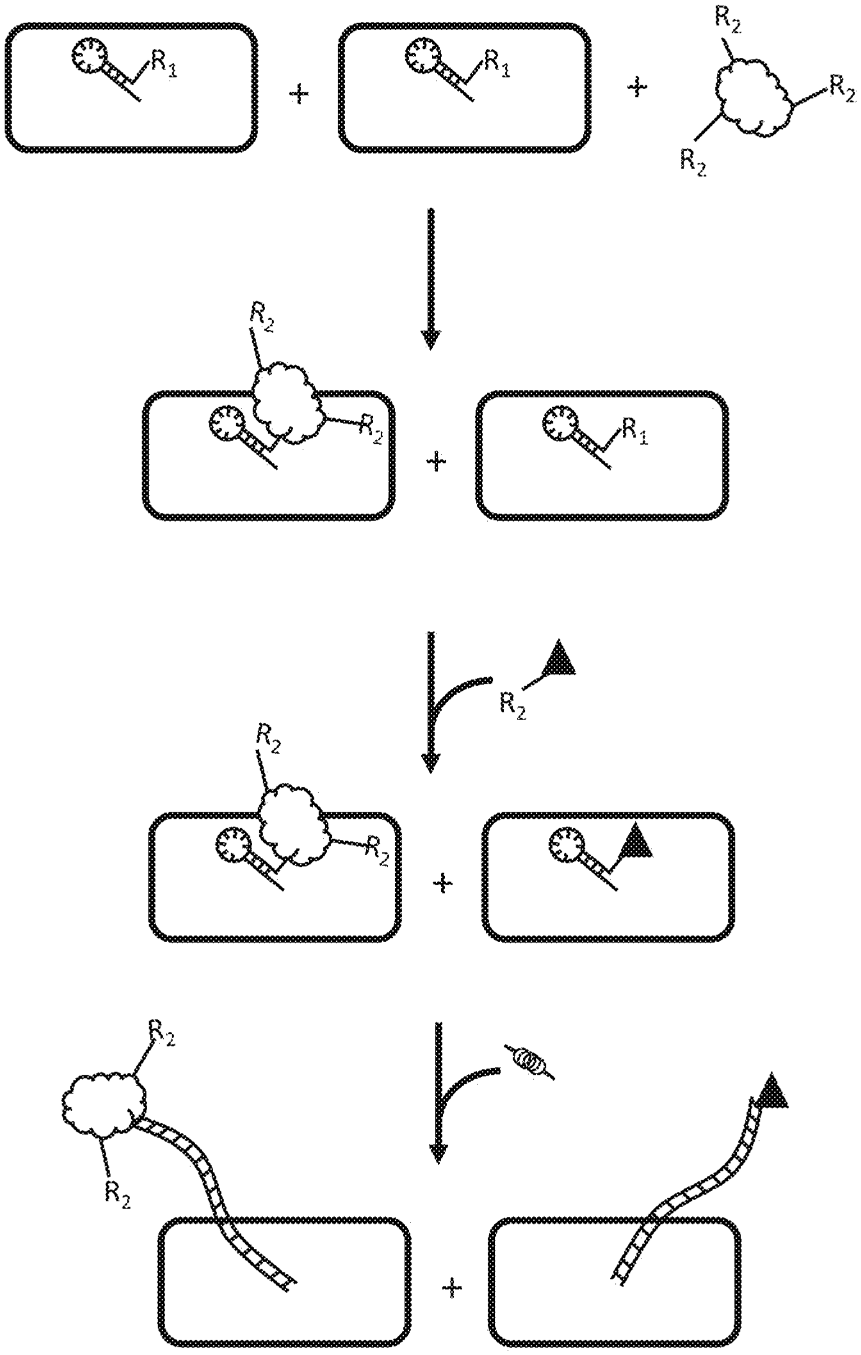
FIG. 2 illustrates a method for attaching a protein to a particle via a nucleic acid linker having a self-complementarity structure and then converting the nucleic acid linker to double-stranded form.

FIG. 2 illustrates a method for attaching a protein to a particle via a nucleic acid linker having a compact structure due to self-complementarity. In a first step, particles (rounded rectangles) attached to first reactive moieties ($R_1$) via a compact nucleic acid linker (hairpin) are reacted with a protein (globule) having a plurality of second reactive moieties ($R_2$). The first reactive moiety reacts with the second reactive moiety to form a bond, thereby attaching the protein to one of the particles. The nucleic acid linker constrains the attached protein from contacting or attaching to a second particle despite the protein having second reactive moieties that are unreacted. For example, the nucleic acid linker can form a hairpin loop, junction, bulge or internal loop. In a second step, the products of the first reaction are treated with a quenching agent having an optional ligand (triangle) and the second reactive moiety. The reaction quenches any first reactive moieties remaining on particles that had been subjected to the first reaction. The quenching agent is inert to the protein. The ligand, if present, can be used to separate quenched particles from protein-attached particles, for example, using a receptor in a solid-phase extraction, precipitation or affinity chromatography process (not shown). Optionally, unreacted proteins can be separated from unreacted particles between the first and second step. In an alternative option, the quenching agent can be added to a mixture of unreacted proteins and unreacted particles. In the third step shown in FIG. 2, the nucleic acid linker is hybridized to a complementary oligonucleotide, thereby changing the conformation of the linker from a constrained state to the more extended state of a double stranded nucleic acid linker (ladder). In the reaction shown, both the protein and ligand are attached to respective particles via the double stranded nucleic acid linker. As such, the protein and ligand are more accessible to binding other reagents (e.g. affinity reagents, receptors, chemical reagents, enzymes, or the like) than when attached to the particles via single-stranded nucleic acid linkers. Quenching and/or separation of particles can occur before or after the third step.

Prior to converting a linker to double-stranded form, for example, in a configuration shown in FIG. 1 or FIG. 2, a reactive moiety on the linker, or a bond between the linker and protein, can be constrained from being further than 50 nm, 10 nm, 1 nm, 0.5 nm, 0.2 nm, or less from the surface of the individual particle. After conversion of the linker to double-stranded state a reactive moiety on the linker or a bond between the linker and protein can be capable of being further than 0.2 nm, 0.5 nm, 1 nm, 10 nm or 50 nm from the surface of the individual particle. A double stranded linker on a particle, although configured to allow a reactive moiety or attached protein to move further from the surface of the particle, can be configured to constrain the movement beyond a desired maximum distance. For example, when particles are intended to be arrayed on a solid support, the maximum distance for movement of a linked protein can be constrained to prevent the protein from contacting an adjacent particle on the support. For example, a double stranded linker can be configured to constrain a reactive moiety, or attached protein, from being further than 1 μm, 750 nm, 500 nm, 250 nm, 100 nm or less from the attachment point of the double-stranded linker on the surface of the particle.

Optionally, a particle in a first state can include two or more domains that are constrained from moving relative to each other, for example, due to a crosslink between the domains. The two or more domains can optionally have increased degrees of motional freedom in a second conformation of the particle, for example, due to removal of a crosslink. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a linker attached a first domain of each of the individual particles to a second domain of each of the individual particles, respectively, the linker comprising a cleavable bond; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) cleaving the cleavable bond, thereby converting the particle of the particle-protein conjugate to a second state wherein the first domain is more distant from the second domain compared to the first state. Alternatively, step (c) can include cleaving the cleavable bond, thereby converting the particle of the particle-protein conjugate to a second state wherein the first domain is more proximal to the second domain compared to the first state.

Figure 3A:
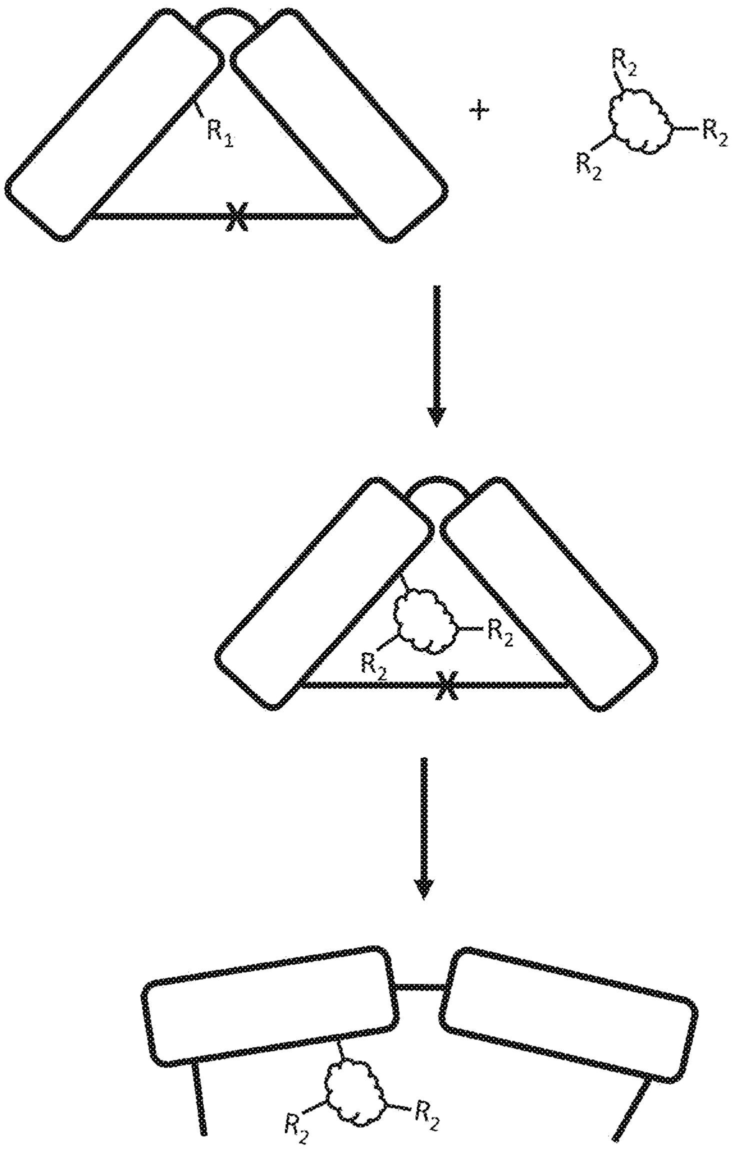
FIG. 3A illustrates a method for attaching a protein to a particle having domains that are crosslinked to inhibit interaction of the particle-attached protein with other particles and then removing the crosslink.

FIG. 3A illustrates a method for attaching a protein to a particle having domains that are crosslinked to inhibit interaction of the particle-attached protein with other particles. In a first step, a particle having two domains (rounded rectangles), one of which is attached to a first reactive moiety ($R_1$) is reacted with a protein (globule) having a plurality of second reactive moieties ($R_2$). The two domains are connected to each other by a flexible linkage (loop) and by a crosslinker (line) having a cleavable bond (X). The first reactive moiety reacts with the second reactive moiety to form a bond, thereby attaching the protein to the particle. The two domains are constrained to a configuration that inhibits the particle-attached protein from contacting or attaching to a second particle despite the protein having second reactive moieties that are unreacted. In this configuration any unreacted second reactive moieties of the particle-attached protein can be restrained from contacting a first reactive moiety on a second particle. In a second step, the cleavable bond of the crosslinker is cleaved, thereby releasing the domains to take on a more open conformation by rotation about the flexible linkage. As such, the protein is more accessible to binding other reagents (e.g. affinity reagents, receptors, chemical reagents, enzymes, or the like) than when the domains were crosslinked. Optionally, unreacted proteins can be separated from unreacted particles between the first and second step. As a further option, the method can include a quenching step, for example, to modify unreacted particles with a ligand for subsequent separation of protein-attached particles from non-reacted particles. Quenching and/or separation of particles can occur before or after cleaving the crosslinker.

Figure 3B:
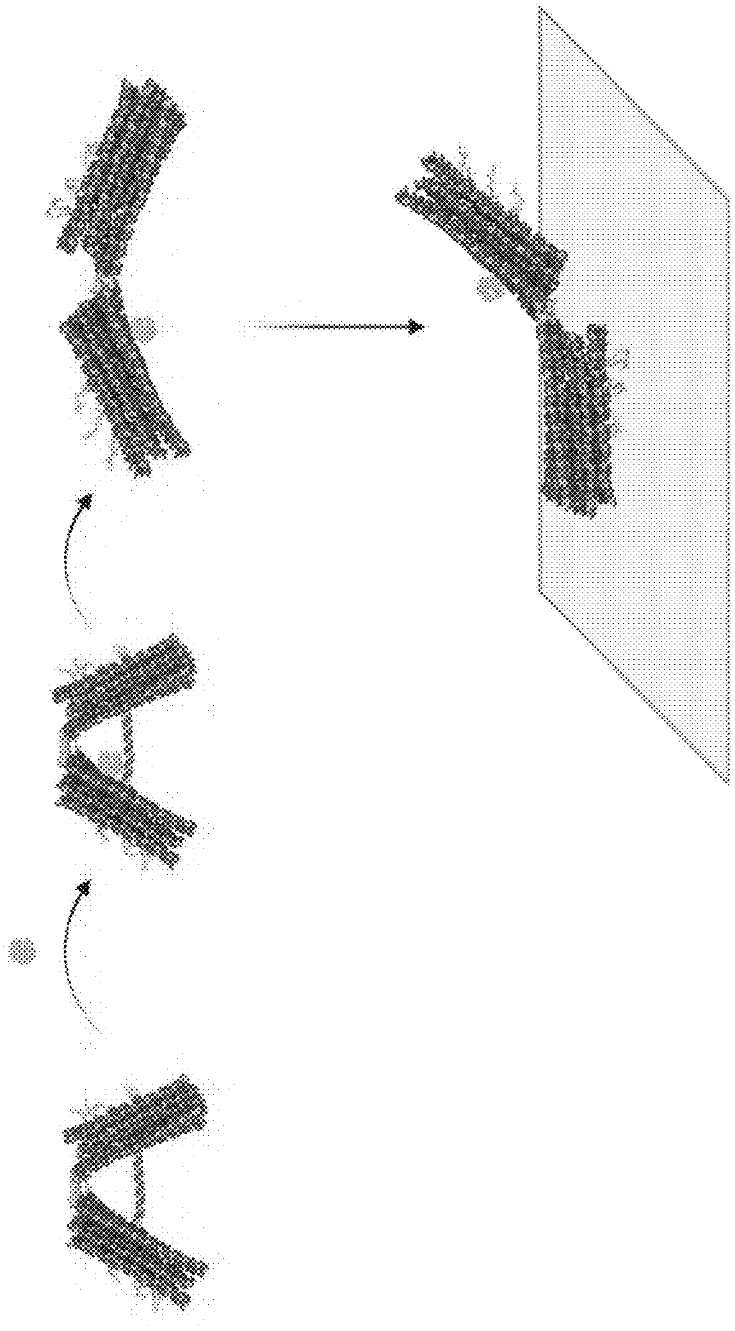
FIG. 3B illustrates a method for attaching a protein to a structured nucleic acid particle having origami domains that are crosslinked to inhibit interaction of the particle-attached protein with other particles, removing the crosslink and attaching the protein to a solid support via interaction of an origami domain with the solid support.

FIG. 3B illustrates a method for attaching a protein to a structured nucleic acid particle (SNAP) having nucleic acid origami domains that are crosslinked via a nucleic acid strand. In the first step, the cross-linked SNAP is reacted with a protein, thereby covalently attaching the protein to one of the nucleic acid origami domains. The two domains are connected to each other by a flexible linkage formed by one or more nucleic acid strands and by a cross-linking nucleic acid strand. The cross-linked SNAP inhibits the SNAP-attached protein from contacting or attaching to a second SNAP even if the protein has unreacted moieties that would otherwise react with a second SNAP. SNAP-attached proteins can optionally be separated from unreacted proteins and/or unreacted SNAPs after the first step shown in the figure. In the second step shown in the figure, the nucleic acid crosslinker is cleaved using a restriction endonuclease or other reagent that is specific for the crosslinker, thereby releasing the domains to take on a more open conformation by rotation about the flexible linkage. As such, the protein is more accessible to binding other reagents (e.g. affinity reagents, receptors, chemical reagents, enzymes, or the like) than when the domains were crosslinked. In the third step shown in FIG. 3B, the SNAP is attached to a solid support via interaction with nucleic acid strands in at least one of the origami domains. For example, the solid support can have a positively charged surface that interacts with negatively charged strands on the SNAP, or the solid support can be attached to one or more oligonucleotides that anneal to strands on the SNAP via Watson-Crick base pairing.

In the examples of FIG. 3A and FIG. 3B, the particle domains are in closer proximity to each other when cross-linked compared to after cleavage of the crosslink. Because the protein is located between the two domains, proximity of the domains reduces accessibility of the protein to other particles or other reagents. Optionally, the domains can be positioned to sterically block the first reactive moiety of a second particle from contacting a second reactive moiety on the particle-attached protein. Alternatively or additionally, the domains can have surface charges that are positioned to repel a second particle such that the first reactive moiety of the second particle is inhibited from contacting a second reactive moiety on the particle-attached protein. Taking a nucleic acid origami particle as an example, one or more of the particle domains can be formed by oligonucleotides that are hybridized to a scaffold. Alternatively, one or more of the particle domains can be origami tiles having separate scaffolds and the tiles can interact with each other via non-covalent interactions, such as hybridization between two or more scaffolds or hybridization of oligonucleotides between two or more scaffolds.

Although the particle domains are exemplified in FIG. 3A and FIG. 3B as being in closer proximity in the crosslinked state, it will be understood that the domains can be configured such that the protein is less accessible when the domains are more distal from each other, and the protein is more accessible when the domains are more proximal to each other. For example, a crosslink can position two domains in an extended state, thereby blocking entry of other particles or reagents from interacting with a protein attached to the particle. In this example, cleaving the cross-link can allow the domains to move toward each other in a more compact overall structure, thereby opening the entry that was previously blocked by the less compact overall structure of the two domains. Taking a nucleic acid origami particle as an example, one or more of the particle domains can be formed by oligonucleotides that are hybridized to a scaffold. Alternatively, one or more of the particle domains can be origami tiles having separate scaffolds and the tiles can interact with each other via non-covalent interactions, such as hybridization between two or more scaffolds or hybridization of oligonucleotides between two or more scaffolds.

In the examples of FIG. 3A and FIG. 3B, the two domains are motile with respect to each other because they are connected via a flexible linkage. However, motile domains need not be directly connected to each other. For example, two domains can be connected to each other via an intermediate domain. One or both of the two motile domains can be connected to the intermediate domain via a flexible linkage. Moreover, a flexible region in one or more motile domain can facilitate relative motility between domains.

Any of a variety of cleavable crosslinkers can be used in a method exemplified in the context of FIG. 3A, FIG. 3B or elsewhere herein. Particularly useful crosslinkers are configured for a covalent linkage whereby a chain of covalent bonds connects moieties, domains and/or objects. Exemplary crosslinkers are set forth, for example, in the *Thermo Scientific Crosslinking Technical Handbook* (2012), which is incorporated herein by reference. Optionally, a crosslinker can include a bond that is chemically labile, photolabile, heat labile, pH labile, or the like. Disulfides are particularly useful cleavable bonds to include in a covalent cross-linker and can be cleaved by a reducing agent such as dithiothreitol. In some configurations, a nucleic acid strand can be covalently attached to two moieties, domains and/or objects. The nucleic acid strand can be cleaved using an enzyme such as a nuclease or using a chemical reagent. A nucleic acid linker can be specifically cleaved using restriction endonuclease that recognizes a sequence that is unique to the linker (e.g. a sequence not found elsewhere in the particle or other substance to which the nucleic acid is crosslinked). A nucleic acid crosslinker can include nucleotide analogs that are chemically or enzymatically cleavable such as deoxyuracil which is cleavable by uracil DNA glycosylase (UDG) and DNA glycosylase-lyase Endonuclease VIII, or 8-oxoguanine which is cleavable by 8-oxoguanine glycosylase. Such nucleotide analogs can be present in the crosslinker and absent elsewhere in the particle such that cleavage is specific to the crosslinker. In some configurations, a peptide is used as a covalent crosslinkage between moieties, domains and/or objects. A peptide crosslinker can be cleavable by a protease or chemical reagent. In some configurations a peptide crosslinker can have a protease recognition site that is not found in the moieties, domains or objects to which it is attached, thereby providing specificity for cleavage of the crosslinkage.

A crosslinker can include one or more non-covalent bonds in the chain of bonds that connects moieties, domains and/or objects. For example, a nucleic acid crosslinker can include two strands that are hybridized to form a double stranded region, each of the two strands being covalently attached to a different moiety, domain or object. Optionally, neither strand of the double stranded nucleic acid linker is covalently attached to both of the crosslinked moieties, domains and/or objects. This double-stranded nucleic acid crosslinker can be effectively cleaved by denaturing the double stranded region, cleaving the double stranded region with a nuclease, or by hybridizing another complementary oligonucleotide to one or both strands of the double stranded region. Other non-covalent linkages that can be included in a crosslinker include, but are not limited to, receptor-ligand pairs set forth herein or known in the art. Probes and affinity reagents set forth herein can be used as non-covalent linkages in a crosslinker.

Optionally, a particle in a first state can include at least two domains that have a first relative position with respect to each other. The two or more domains can have a second relative position (e.g. closer or further compared to the first relative position) in a second conformation of the particle, for example, due to introduction of a crosslink between the domains. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) crosslinking a first domain of the particle to a second domain of the particle, thereby converting the particle of the particle-protein conjugate to a second state wherein the first domain is more distant from the second domain compared to the first state. Alternatively, step (c) can include crosslinking a first domain of the particle to a second domain of the particle, thereby converting the particle of the particle-protein conjugate to a second state wherein the first domain is more proximal to the second domain compared to the first state.

Figure 4:
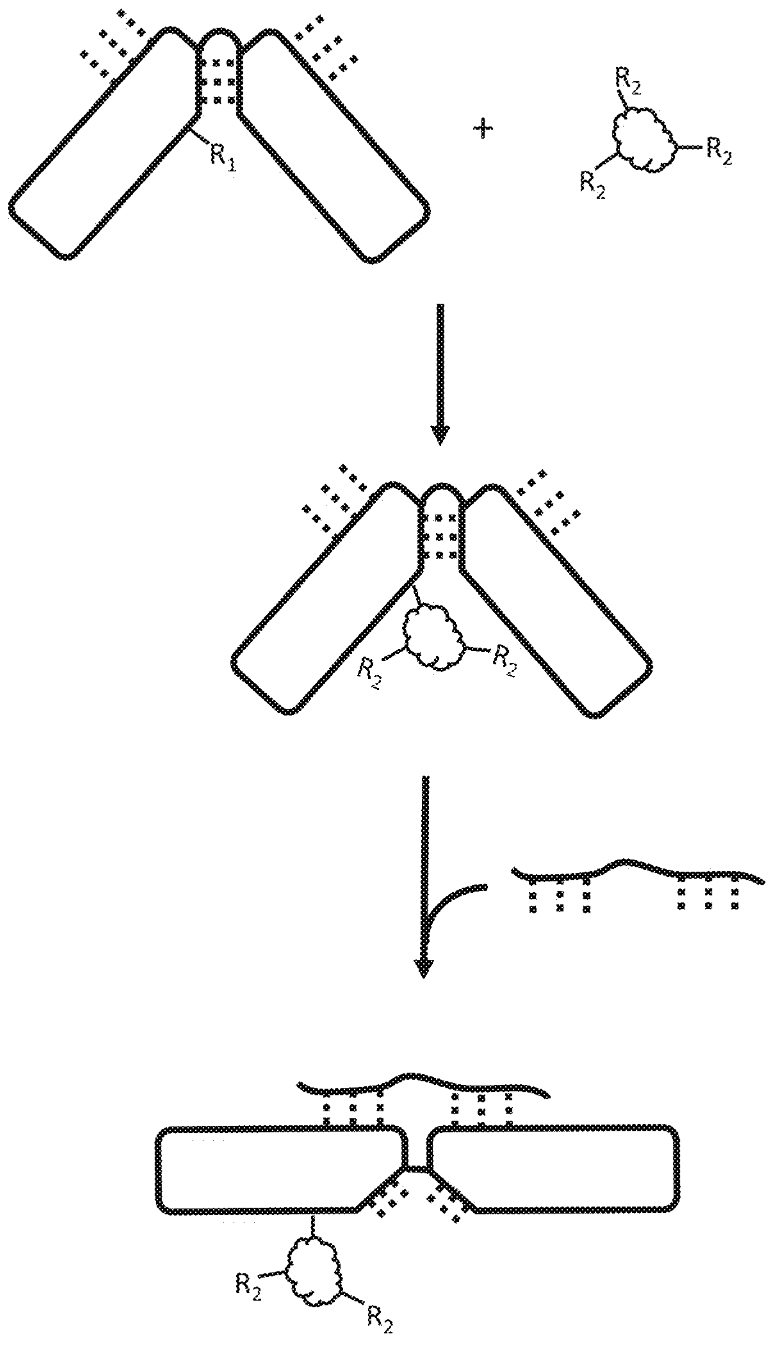
FIG. 4 illustrates a method for attaching a protein to a particle having domains that are conformationally constrained to inhibit interaction of the particle-attached protein with other particles prior to reaction with a crosslinker.

FIG. 4 illustrates a method for attaching a protein to a particle having domains that are constrained to inhibit contact of the particle-attached protein with other particles. In a first step, a particle having two domains (rounded pentagons), one of which is attached to a first reactive moiety ($R_1$) is reacted with a protein (globule) having a plurality of second reactive moieties ($R_2$). The two domains are connected to each other by a flexible covalent linkage (loop) and by non-covalent interactions (dotted lines). The first reactive moiety reacts with the second reactive moiety to form a bond, thereby attaching the protein to the particle. The two domains are constrained to a configuration that inhibits the particle-attached protein from contacting or attaching to a second particle despite the protein having second reactive moieties that are unreacted. In this configuration any unreacted second reactive moieties of the particle-attached protein can be restrained from contacting a first reactive moiety on a second particle. In a second step, a crosslinker (wavy line) reacts with the particle, thereby releasing the domains to take on a more open conformation by rotation about the flexible linkage. As such, the protein is more accessible to binding other reagents (e.g. affinity reagents, receptors, chemical reagents, enzymes, or the like) than when the domains were not in contact with the crosslinker. Optionally, unreacted proteins can be separated from unreacted particles between the first and second step. As a further option, the method can include a quenching step, for example, to modify unreacted particles with a ligand for subsequent separation of protein-attached particles from non-reacted particles. Quenching and/or separation of particles can occur before or after the crosslinking step.

In the example of FIG. 4, the crosslinker forms non-covalent interactions (dotted lines) with the two domains of the particle and the interactions between the crosslinker and the domains is energetically more favorable than the non-covalent interactions that previously constrained the domains. By way of more specific example, the domains can be regions of a nucleic acid origami particle, such as regions of a scaffold, regions of an oligonucleotide hybridized to a scaffold or regions of both, that interact with each other via Watson-Crick base pairing, hydrogen bonds or ionic interactions. Continuing with the example, the crosslinker can be an oligonucleotide that interacts with the domains via Watson-Crick base pairing, hydrogen bonds or ionic interactions. As exemplified in the figure, the crosslinker can interact with regions of the two domains other than the regions of the domains that interacted with each other in the absence of the crosslinker. Alternatively or additionally, the crosslinker can interact directly with regions of one or both domains that interacted with each other in the absence of the crosslinker. The crosslinker need not be a nucleic acid nor does the crosslinker need to interact non-covalently with the particle. For example, a chemical crosslinker can form a covalent bond with one or both domains to change the conformation of the particle.

In the example of FIG. 4, the particle domains are in closer proximity to each other prior to crosslinking compared to after. Because the protein is located between the two domains, proximity of the domains decreases accessibility of the protein to other particles or other reagents. However, it will be understood that the domains can be configured such that the protein is less accessible when the domains are more distal to each other, and the protein is more accessible when the domains are more proximal to each other. For example, interactions between two domains can block entry of other particles or reagents from interacting with a protein attached to the particle. In this example, adding a crosslink can allow the domains to move proximal to each other, thereby opening the previously blocked entry. Taking a nucleic acid origami particle as an example, one or more of the particle domains can be formed by oligonucleotides that are hybridized to the same scaffold. The oligonucleotides can interact with each other prior to being contacted with a crosslinker. Alternatively, one or more of the particle domains can be origami tiles having separate scaffolds. In this case, the tiles can interact with each other via non-covalent interactions, such as hybridization between two or more scaffolds or hybridization of oligonucleotides between two or more scaffolds, prior to being contacted with a crosslinker.

In the example of FIG. 4 the two domains are motile relative to each other because they are connected via a flexible linkage. However, motile domains need not be directly connected to each other. For example, two domains can be connected via an intermediate domain. One or both of the two motile domains can be connected to the intermediate domain via a flexible linkage. Moreover, a flexible region in one or more motile domain can facilitate relative motility between domains.

Optionally, a particle in a first state can include at least two domains that have a first relative position with respect to each other. The two or more domains can have a second relative position (e.g. closer or further compared to the first relative position) in a second conformation of the particle, for example, due to binding of the particle to a solid support. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, and wherein each of the particles is in a first state; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) attaching a first domain of the particle to a solid support and attaching a second domain of the particle to a solid support, thereby converting the particle of the particle-protein conjugate to a second state wherein the first domain is more distant from the second domain compared to the first state. Alternatively, step (c) can include attaching a first domain of the particle to a solid support and attaching a second domain of the particle to a solid support, thereby converting the particle of the particle-protein conjugate to a second state wherein the first domain is more proximal to the second domain compared to the first state.

Figure 5:
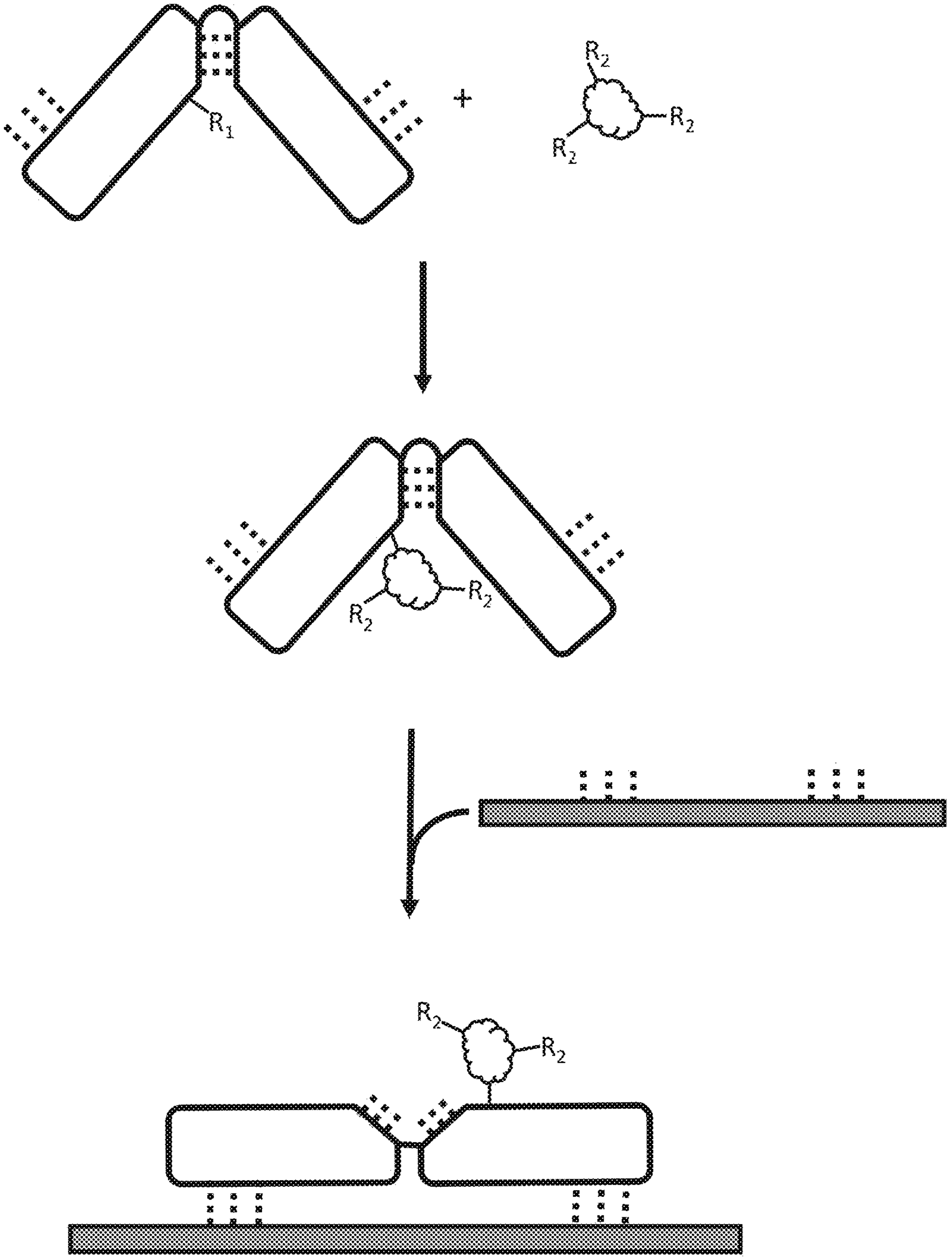
FIG. 5 illustrates a method for attaching a protein to a particle having domains that are constrained to inhibit interaction of the particle-attached protein with other particles prior to reaction with a surface.

FIG. 5 illustrates a method for attaching a protein to a particle having domains that are constrained to inhibit interaction of the particle-attached protein with other particles. In a first step, a particle having two domains (rounded pentagons), one of which is attached to a first reactive moiety ($R_1$) is reacted with a protein (globule) having a plurality of second reactive moieties ($R_2$). The two domains are connected to each other by a flexible covalent linkage (loop) and by non-covalent interactions (dotted lines). The first reactive moiety of the particle reacts with a second reactive moiety of the protein to form a bond, thereby attaching the protein to the particle. The two domains are constrained to a configuration that inhibits the particle-attached protein from contacting or attaching to a second particle despite the protein having second reactive moieties that are unreacted. In this configuration any unreacted second reactive moieties of the particle-attached protein can be restrained from contacting a first reactive moiety on a second particle. In a second step, the particle is attached to a surface, thereby reorienting the domains to a more open conformation. As such, the protein is more accessible to binding other reagents (e.g. affinity reagents, receptors, chemical reagents, enzymes, or the like) than when the domains were not attached to the surface. Optionally, unreacted proteins can be separated from unreacted particles between the first and second step. As a further option, the method can include a quenching step, for example, to modify unreacted particles with a ligand for subsequent separation of protein-attached particles from non-reacted particles. Quenching of non-reacted particles and/or separation of non-reacted particles from protein-attached particles, can be carried out prior to attaching the protein-attached particle to the solid-support. Optionally, quenching of non-reacted particles and/or separation of non-reacted particles from protein-attached particles can occur attaching the protein-attached particle to the solid-support.

In the example of FIG. 5, the solid support forms non-covalent interactions (dotted lines) with the two domains of the particle and the interactions between the surface and the domains is energetically more stable than the interactions that previously constrained the domains. By way of more specific example, the domains can be regions of a nucleic acid origami particle, such as regions of a scaffold, regions of an oligonucleotide hybridized to a scaffold or regions of both, that interact with each other via Watson-Crick base pairing, hydrogen bonds or ionic interactions. Continuing with the example, the solid support can be attached to one or more oligonucleotides that interacts with the domains via Watson-Crick base pairing, hydrogen bonds or ionic interactions. In another configuration, the solid support can have a charged surface that interacts with the domains via hydrogen bonds, ionic interactions or salt bridges (e.g. using a divalent cation such as $Mg^{2+}$). As exemplified in the figure, the solid support can interact with regions of the two domains other than the regions of the domains that interacted with each other in the absence of the solid support. Alternatively or additionally, the solid support can interact directly with regions of one or both domains that interacted with each other in the absence of the solid support. The solid support need not attach non-covalently with the particle. For example, a chain of covalent bonds can mediate attachment of the solid support to one or both domains of the particle. Moreover, the solid support need not have a flat surface as shown. For example, the solid support can have a convex or concave surface to which one or both domains of the particle attach.

In the example of FIG. 5, the particle domains are in closer proximity to each other prior to crosslinking compared to after. As set forth in the context of FIGS. 3 and 4, the domains can be configured such that the protein is less accessible when the domains are more distal to each other, and the protein is more accessible when the domains are more proximal to each other. Furthermore, the two domains are connected to each other via a flexible linkage in the example of FIG. 5. However, the motile domains need not be directly connected to each other and can have other connectivity, for example as set forth in the context of FIGS. 3 and 4.

Optionally, a particle in a first state can include a blocking moiety that inhibits interaction of a protein with a second particle when attached to the particle. The blocking moiety can be removed in a second conformation of the particle. A method for attaching a particle to a protein can include steps of (a) forming a reaction mixture including: (i) a plurality of proteins, wherein individual proteins of the plurality of proteins each include a plurality of first reactive moieties, (ii) a plurality of particles, wherein individual particles of the plurality of particles each include a second reactive moiety, wherein the second reactive moiety of the particles is reactive with the first reactive moieties of the proteins, wherein each of the particles is in a first state wherein a blocking moiety is attached to each of the individual particles; and (b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the first state of the particles inhibits more than one of the particles in the reaction mixture from attaching to the protein, thereby forming a particle-protein conjugate. The method can optionally include a step of (c) removing the blocking moiety from the particle of the particle-protein conjugate, thereby converting the particle of the particle-protein conjugate to a second state that lacks the blocking moiety. Alternatively, step (c) can include crosslinking the blocking moiety to a second moiety of the individual particle to which the blocking moiety is attached, thereby converting the particle of the particle-protein conjugate to a second state. As a further alternative, step (c) can include attaching the blocking moiety of the particle-protein conjugate to a solid support, thereby converting the particle of the particle-protein conjugate to a second state.

Figure 6:
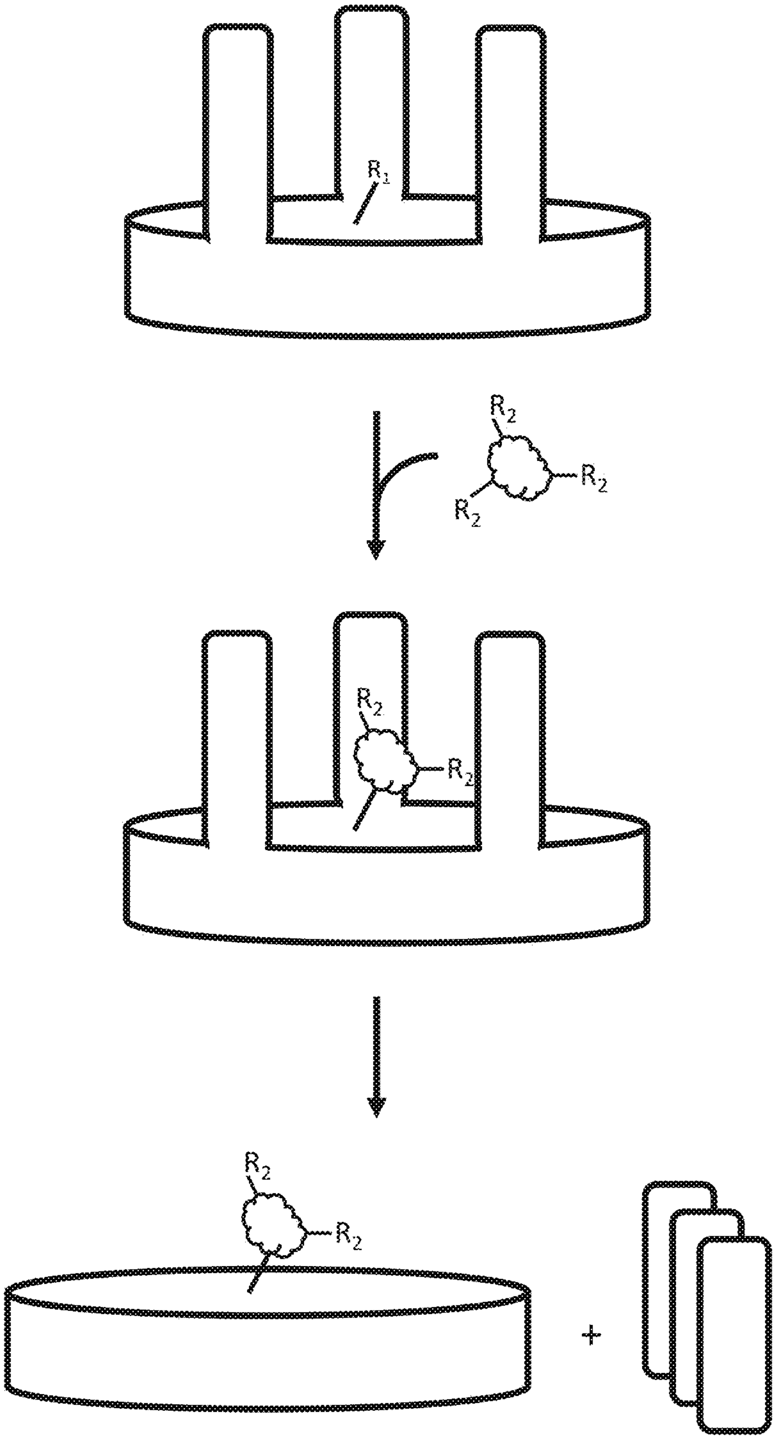
FIG. 6 illustrates a method for attaching a protein to a particle having blocking moieties that inhibit interaction of the particle-attached protein with other particles prior to removal of the blocking moieties.

FIG. 6 illustrates a method for attaching a protein to a particle having blocking moieties that inhibit interaction of the particle-attached protein with other particles. In a first step, a particle (disk) having three blocking moieties (rounded rectangles) and a first reactive moiety ($R_1$) is reacted with a protein (globule) having a plurality of second reactive moieties ($R_2$). The first reactive moiety of the particle reacts with a second reactive moiety of the protein to form a bond, thereby attaching the protein to the particle. The blocking moieties inhibit the protein from contacting or attaching to a second particle despite the protein having second reactive moieties that are unreacted. For example, the blocking moieties on the protein-attached particle prevent second reactive groups on the protein from contacting the first reactive moiety of a second particle. Moreover, the blocking moieties on the second particle further inhibit this contact. In a second step, the blocking moieties are cleaved from the particle. As such, the particle-attached protein becomes more accessible to binding other reagents (e.g. affinity reagents, receptors, chemical reagents, enzymes, or the like) than when the blocking moieties were present. Optionally, unreacted proteins can be separated from unreacted particles between the first and second step. As a further option, the method can include a quenching step, for example, to modify unreacted particles with a ligand for subsequent separation of protein-attached particles from non-reacted particles. Quenching and separation of non-reacted particles, can be carried out before or after cleaving the blocking moieties.

The blocking moieties can create steric hindrance that prevents unreacted second reaction moieties on the particle-attached protein from contacting unreacted first reaction moieties on a second particle. The hindrance need not be solely steric, nor steric at all. For example, the blocking moieties can have similarly charged surfaces such that blocking moieties on two particles repel the particles from achieving a relative orientation and distance in which a protein attached to one of the particles contacts a reactive group on the other particle. Similarly, blocking moieties of the particles can have similar charge to the surface of the particles to which the first reactive moiety or protein is attached. As such, the blocking moieties of a first particle will repel the surface of the second particle, thereby preventing two particles from attaching to the same protein.

Particles having the functions exemplified in the context of FIG. 6 can be nucleic acid origami particles. The blocking moieties can be formed by oligonucleotides that are hybridized to the same scaffold. Alternatively, the blocking moieties can be oligonucleotides that are hybridized to different scaffolds. In some configurations, one or more blocking moieties can include a scaffold that is separable from the scaffold to which a protein is attached. For example, a blocking moiety can form an origami tile that is separate from an origami tile to which a protein is attached. The tiles can be attached to each other via one or more of hybridization between regions of the respective scaffolds, hybridization between a scaffold of one tile and an oligonucleotide to a second tile, or hybridization of an oligonucleotide to scaffolds of both tiles. Blocking moieties can also be attached to other regions of an origami particle using a crosslinker or attachment chemistry set forth herein or known in the art.

Blocking moieties can be removed by cleaving a linkage between the blocking moieties and a region of the particle that is attached to a protein. Such methods include, for example, denaturation of linkages formed via hybridization, nucleolytic cleavage of nucleic acid strands, cleavage at non-native nucleotide positions, chemical cleavage or other methods set forth herein or known in the art for cleaving nucleic acid linkers. Alternatively or additionally, blocking moieties can be degraded or chemically modified to reverse their capacity to block interactions of other reagents with attached proteins. For example, a charged blocking moiety can be modified to mask the charge (i.e. neutralized) or to change the charge to the opposite polarity (i.e. from negative to positive or vice versa).

A method set forth herein, for example, in the context of FIG. 1 through FIG. 6, can be carried out by limiting protein relative to particles during a reaction to attach proteins to particles. The limitation of protein can be due to the molar amount of proteins being less than the molar amount of particles, or it can be due to a lower concentration of proteins compared to the concentration of particles. As such, particles will be in excess during the attachment reaction. Having an excess of particles favors attachment of only one protein per particle. Optionally, single protein attachment per particle can also be favored by minimizing the number of reactive moieties on the particle that are reactive toward protein. For example, each particle can be configured to have only a single reactive moiety that is reactive toward protein. When particles are in excess compared to protein, attachment of more than one particle per protein can be inhibited by functionalizing each protein with only a single reactive moiety that is reactive with the particles. Many techniques for functionalizing proteins yield multiple functional groups being added to each individual protein. An advantage of the compositions and methods set forth herein is that individual proteins can each be attached with a single particle even if the proteins have multiple reactive moieties that are reactive to the particles and even if the particles are in excess during an attachment reaction.

The present disclosure also provides a method for attaching a particle to a protein, the method including steps of (a) forming a reaction mixture including: (i) a plurality of proteins, wherein individual proteins of the plurality of proteins each include a plurality of first reactive moieties, and (ii) a plurality of immobilized particles, wherein individual immobilized particles of the plurality of immobilized particles each includes a second reactive moiety, wherein the second reactive moiety of the immobilized particles is reactive with the first reactive moieties of the proteins, and wherein the immobilized particles are attached to one or more solid supports; (b) reacting a first reactive moiety of a protein in the reaction mixture with a second reactive moiety of an immobilized particle in the reaction mixture to attach the protein to the immobilized particle via a bond formed between the first reactive moiety of the protein and the second reactive moiety of the immobilized particle, thereby forming an immobilized particle-protein conjugate; and (c) detaching the immobilized particle-protein conjugate from the solid support, thereby producing a solution-phase particle-protein conjugate.

Particles can be in an immobilized state during a reaction for attaching proteins to the particles. Immobilizing the particles can prevent them from interacting with each other during a protein attachment reaction, thereby providing the advantage of inhibiting more than one particle from attaching to an individual protein. As such, proteins can have more than one reactive moiety and yet be inhibited from attaching to more than one particle. This can provide the advantage of opening up a wider range of reactive moieties and techniques for functionalizing proteins with those moieties than may otherwise be available.

In some configurations, a reaction for attaching proteins to immobilized particles can include a relative excess of proteins which can beneficially drive the reaction to produce a higher yield of protein-attached particles compared to the yield of non-reacted particles. Configuring the particle attachment reaction to have an excess of proteins relative to particles, can be useful, for example, when attempting to deplete a protein sample of abundant proteins via particle capture, thereby yielding a solution phase protein sample that is enriched for lower abundance proteins. A protein attachment reaction can be configured to have at least a 1.1×, 1.5×, 2×, 5×, 10×, 100× or higher excess of proteins relative to particles. Alternatively or additionally, a protein attachment reaction can be configured to have at most a 100×, 10×, 5×, 2×, 1.5×, 1.1× or lower excess of proteins relative to particles. An excess of one reactant type relative to another type can be manifest as a higher number of the one reactant type relative to the number of the other type or as a higher concentration of the one reactant type relative to the concentration of the other.

In some configurations, a reaction for attaching proteins to immobilized particles can include a relative excess of particles which can beneficially drive the reaction to produce a higher yield of particle-attached proteins compared to the yield of non-reacted proteins. Configuring the particle attachment reaction to have an excess of particles relative to proteins, can be useful, for example, when attempting to capture as much of the protein content of a sample as possible. A protein attachment reaction can be configured to have at least a 1.1×, 1.5×, 2×, 5×, 10×, 100× or higher excess of particles relative to proteins. Alternatively or additionally, a protein attachment reaction can be configured to have at most a 100×, 10×, 5×, 2×, 1.5×, 1.1× or lower excess of particles relative to proteins. As set forth in further detail below, protein-attached particles can be separated from particles that lack protein to produce an enriched fraction of protein-attached particles for subsequent assay. For example, the enriched fraction of protein-attached particles can be attached to one or more solid support to create an array having a high occupancy rate for individually resolved proteins. Thus, the methods set forth herein can provide the advantage of producing arrays having high occupancy with respect to the number of sites having protein present and having reduced incidence of sites having more than a single protein present.

Particles can be immobilized an any of a variety of ways. For example, a plurality of particles can be attached to a surface of a solid support. An exemplary configuration is an array of particles in which each particle occupies a site of the array. The sites can be arranged in an ordered or repeating pattern such as a line of spatially separated sites, a curve or spiral of spatially separated sites, a rectilinear grid of spatially separated sites, or hexagonal grid of spatially separated sites. Alternatively, the sites can be arranged randomly in a non-repeating pattern. For example, attachment sites for the particles need not be present in a pattern on a surface, and instead a lawn of attachment sites can be present on the surface to which particles will be, or are, attached. Whether beads are arranged in an ordered or random pattern on a solid support, the spatial separation can be configured such that particles abut each other or such that particles are separated by a gap. Accordingly, the average pitch for the sites can be equivalent to or greater than the longest dimension of the particles. For example, the average pitch for the sites can be at least 100 nm, 250 nm, 500 nm, 750 nm, 1 μm, 5 μm, 10 μm or more. Alternatively or additionally, the average pitch for the sites can be at most 10 μm, 5 μm, 1 μm, 750 nm, 500 nm, 250 nm, 100 nm or less.

A solid support can have a planar surface to which particles are attached. However, the surface need not be planar. For example, particles can be attached to contours or features on a solid support such as wells, pits, channels or other concave contours. Optionally, particles can be attached to posts, ridges, or other protruding contours. In another example, particles can be attached to beads or other separable solid supports. The separable solid supports can have flat surfaces, curved surfaces or irregular surfaces. Solid supports can be porous, for example, with particles attached within pores.

In some configurations a single particle is attached to a single solid support.

Alternatively, multiple particles can be attached to the same solid support. For example, a solid support can be attached to at least about 1 particle, 10 particles, 100 particles, $1\times10^3$ particles, $1\times10^4$ particles, $1\times10^5$ particles, $1\times10^6$ particles, or more. Alternatively or additionally, a solid support can include at most about $1\times10^6$ particles, $1\times10^5$ particles, $1\times10^4$ particles, $1\times10^3$ particles, 100 particles, 10 particles or 1 particle. A plurality of particles can be attached to a plurality of solid supports. This can be the case whether each particle of the plurality is attached to a single solid support or multiple particles of the plurality are attached per solid support.

Particles can be attached to solid supports using chemistries set forth herein for attaching substances to each other. The chemistries can involve covalent or non-covalent binding. In either case, the attachment of particle to the solid support can be reversible to facilitate subsequent detachment of the particle from the solid support. For example, cleavable covalent bonds (e.g. chemically cleavable, enzymatically cleavable or photolytically cleavable) can be used or non-covalent bonds (e.g. nucleic acid hybrids, receptor-ligand pairs, ionic interactions, polar interactions, van der Waals forces, hydrogen bonds etc.) can be used. Particles can be detached from solid supports using reagents and methods set forth herein for disrupting crosslinks or using reagents and methods known in the art.

Figure 7A:
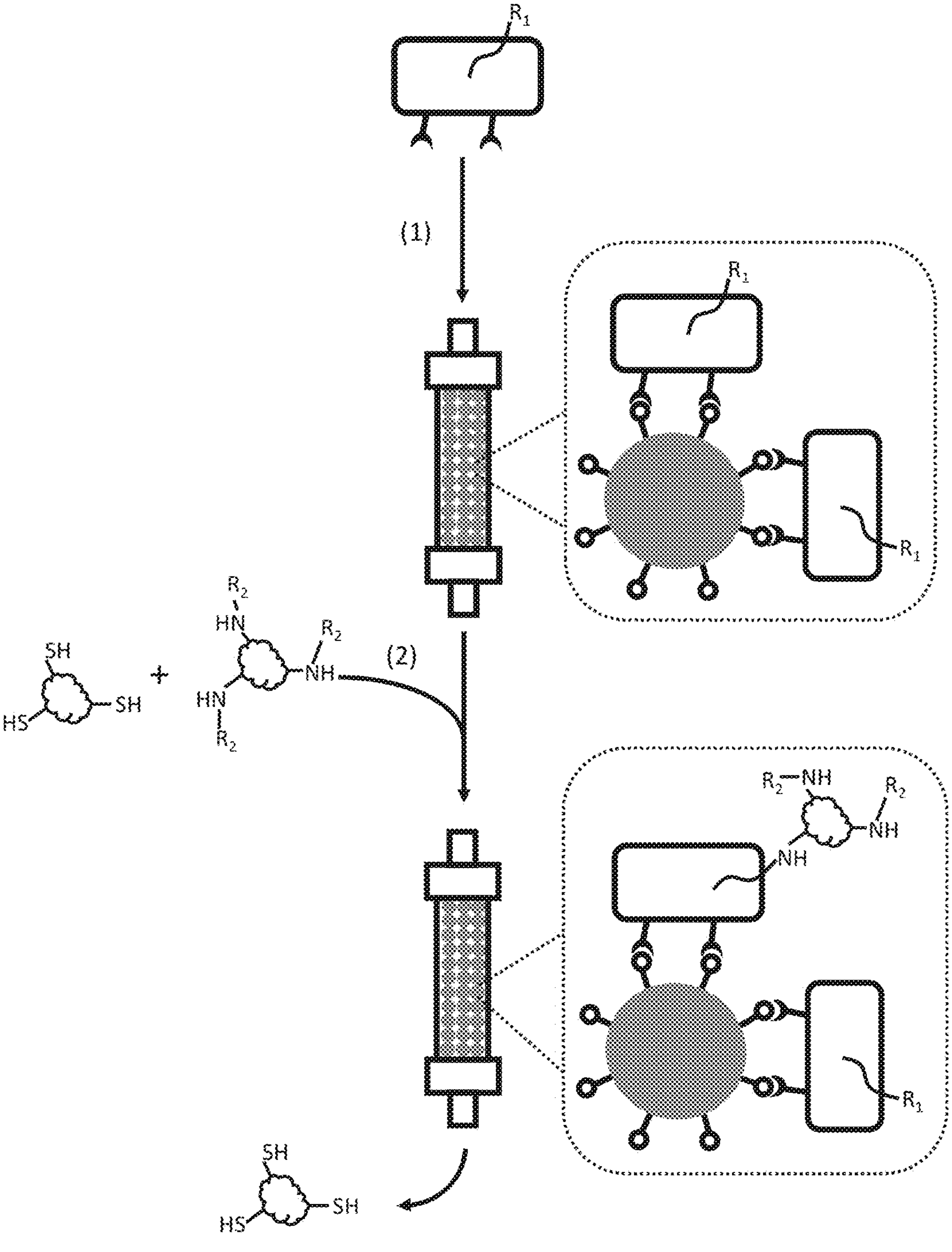
FIG. 7A illustrates a method for attaching proteins to immobilized particles.

FIG. 7A illustrates an exemplary method for attaching proteins to immobilized particles. In the first step shown, particles (rounded rectangle) having a first reactive moiety ($R_1$) and receptors (crescents) are contacted with beads (grey circle) having ligands (open circles) for the receptors. In the example shown, the beads are retained in a column and the particles (and other subsequent fluids) are flowed through the column. Immobilization of particles on a bead, via binding of the receptors to the ligands, is shown within the dotted lines of the expanded region. In a second step, a protein sample is flowed through the column to contact the immobilized particles. The protein sample, having been functionalized with a second reactive moiety ($R_2$) using an amine reactive precursor, includes a mixture of functionalized and non-functionalized proteins (globules). As shown in the second expanded region, the functionalized protein attaches to a particle via reaction between the first and second reactive moieties. The non-functionalized protein flows through the column and can be collected or discarded. Structured nucleic acid particles, such as particles composed of nucleic acid origami can be particularly useful in the methods exemplified in FIG. 7A (and FIGS. 7B through 7D).

The use of beads in a column to immobilize particles is exemplary. A column is convenient since immobilized particles can be contained in a channel and fluids can pass through an ingress to contact the immobilized particles and flow out of the channel via an egress. Beads having immobilized particles can be contained in any of a variety of other vessels, and fluids can be delivered to the immobilized particles using fluidic manipulations appropriate to those vessels. For example, beads having immobilized particles can be in a tube (e.g. test tube or Eppendorf tube), in a well of a multiwell plate, in a filter-bottom well, in a capillary channel or the like. In some cases, particles can be immobilized in an array, such as an array of beads or an array of particle attachment sites on a surface of a solid support. Fluids can be delivered to immobilized particles, for example, via aspiration, pipetting, fluid displacement via a motorized pump, droplet delivery or the like. Fluids can be removed from immobilized particles, for example, by the same methods used for delivery or by passage through a frit or filter that passes fluids while retaining immobilized particles.

Figure 7B:
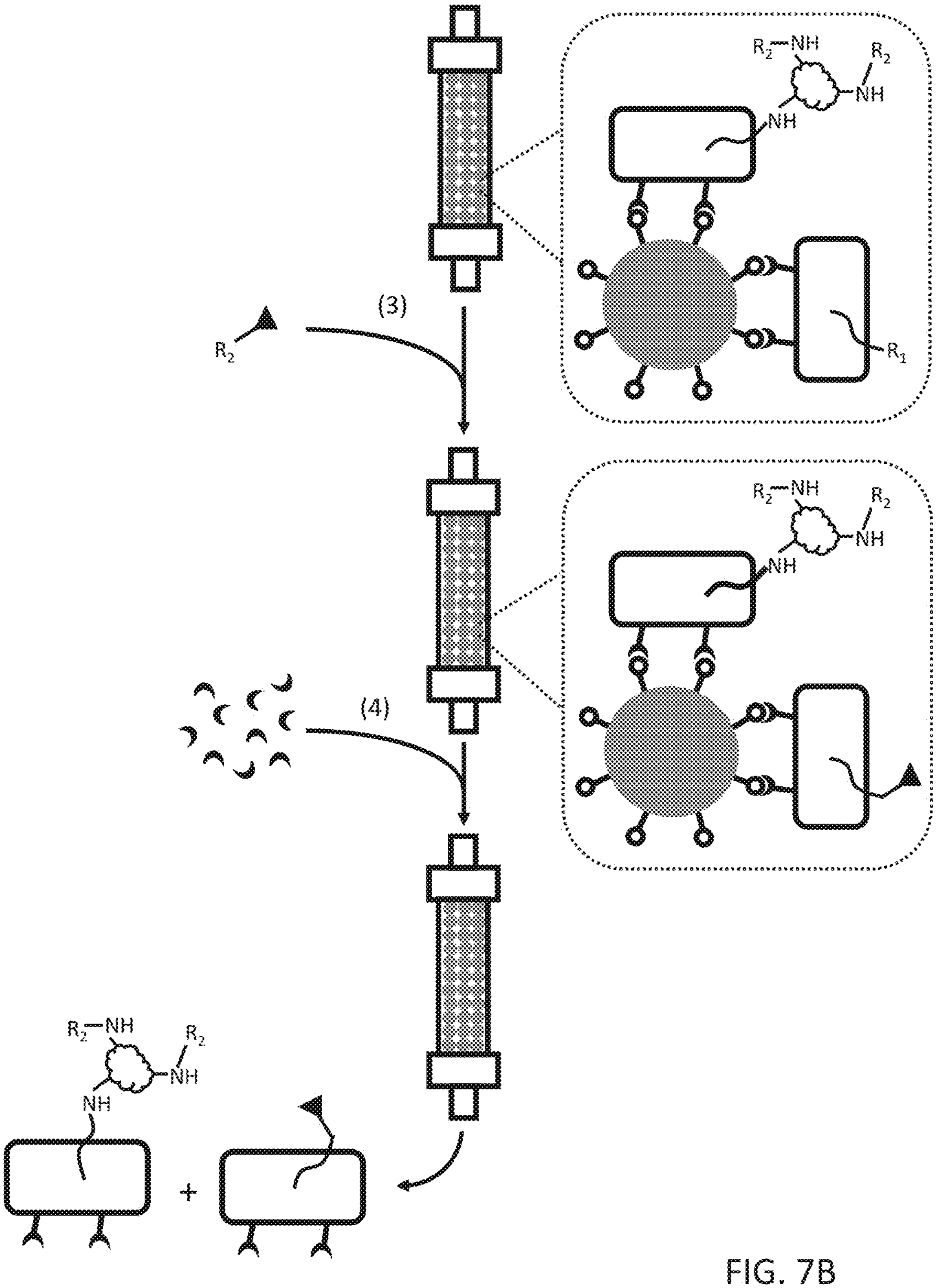
FIG. 7B illustrates a method for quenching unreacted reactive moieties on particles and releasing particles from solid supports to which they were immobilized.

FIG. 7B illustrates an exemplary method for quenching unreacted reactive moieties on particles and releasing particles from solid supports to which they were immobilized. Although not required, the method is exemplified as proceeding from initial steps performed as exemplified for FIG. 7A. In the third step, a quenching agent having an optional ligand (triangle) and the second reactive moiety is delivered to the column. Any first reactive moieties remaining on particles are quenched. In the fourth step, the protein-attached particles and ligand-attached particles are detached from the beads and eluted from the column. The particles are detached by delivery of solution-phase receptors (crescents) which compete with the particle-attached receptors for the ligands on the beads. Other elution methods can be used to detach the particles such as those known in the art for detaching target molecules of interest during affinity chromatography or affinity precipitation techniques.

A ligand, if present on a quenching reagent, can be used to separate quenched particles from protein-attached particles after particles have been removed from the beads. For example, the eluate from the process shown in FIG. 7B, can be contacted with immobilized receptor under conditions that allow the ligand to bind to the immobilized receptor such that quenched particles are effectively immobilized while the protein-attached particles remain in solution phase. The solution phase and immobilized phase can be separated to separate the protein-attached particles for further use. A particularly useful configuration employs a column containing immobilized receptor. For example, the eluate from the column shown in FIG. 7B can be delivered to the ingress of a receptor column (e.g. a column having receptors immobilized on beads), quenched particles can attach to the beads, and protein-attached particles can be collected as a fluid-phase eluate from the receptor column. The protein-attached particles can then be used in a downstream process, for example, being attached to an array for an analytical assay.

Figure 7C:
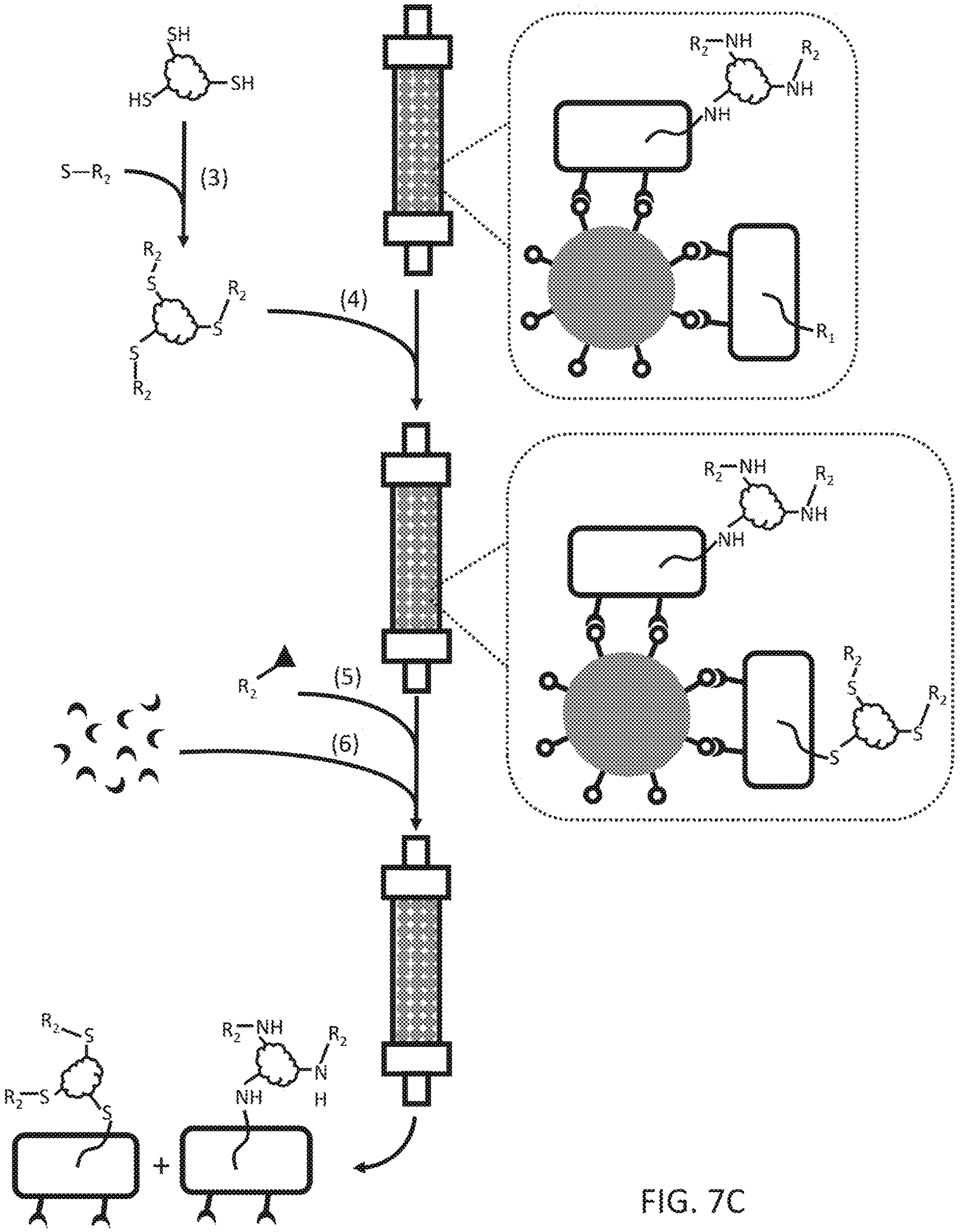
FIG. 7C illustrates a method for increasing diversity of functionalized proteins attached to immobilized particles and harvesting the particles to obtain a mixed fraction of particle-attached proteins.

FIG. 7C illustrates an exemplary method for increasing diversity of functionalized proteins attached to immobilized particles and harvesting the particles to obtain a mixed fraction of particle-attached proteins. Although not required, the method is exemplified as proceeding from initial steps performed as exemplified for FIG. 7A. In the third step, non-functionalized protein is functionalized with a second reactive moiety ($R_2$) using a sulfhyril reactive precursor ($S—R_2$). In a fourth step, the functionalized protein product of the third step is flowed through the column to contact the immobilized particles. In the example shown, the column includes beads that retain particles that were attached in the process of FIG. 7A. As shown in the first expanded region of FIG. 7C, the immobilized particles include those that are attached to protein from the prior attachment reaction and particles that are unreacted and thus have a first reactive moiety. As shown in the second expanded region of FIG. 7C, the protein product of the third step attaches to a particle via bond formation resulting from reaction between the first and second reactive moieties. The fifth and sixth steps are performed to quench unreacted reactive moieties on the particles and to elute particles from the column. The eluted fraction includes proteins that were attached in steps two and four of the combined process of FIG. 7A and FIG. 7C. The protein-attached particles can then be used in a downstream process, for example, being attached to an array for an analytical assay.

Figure 7D:
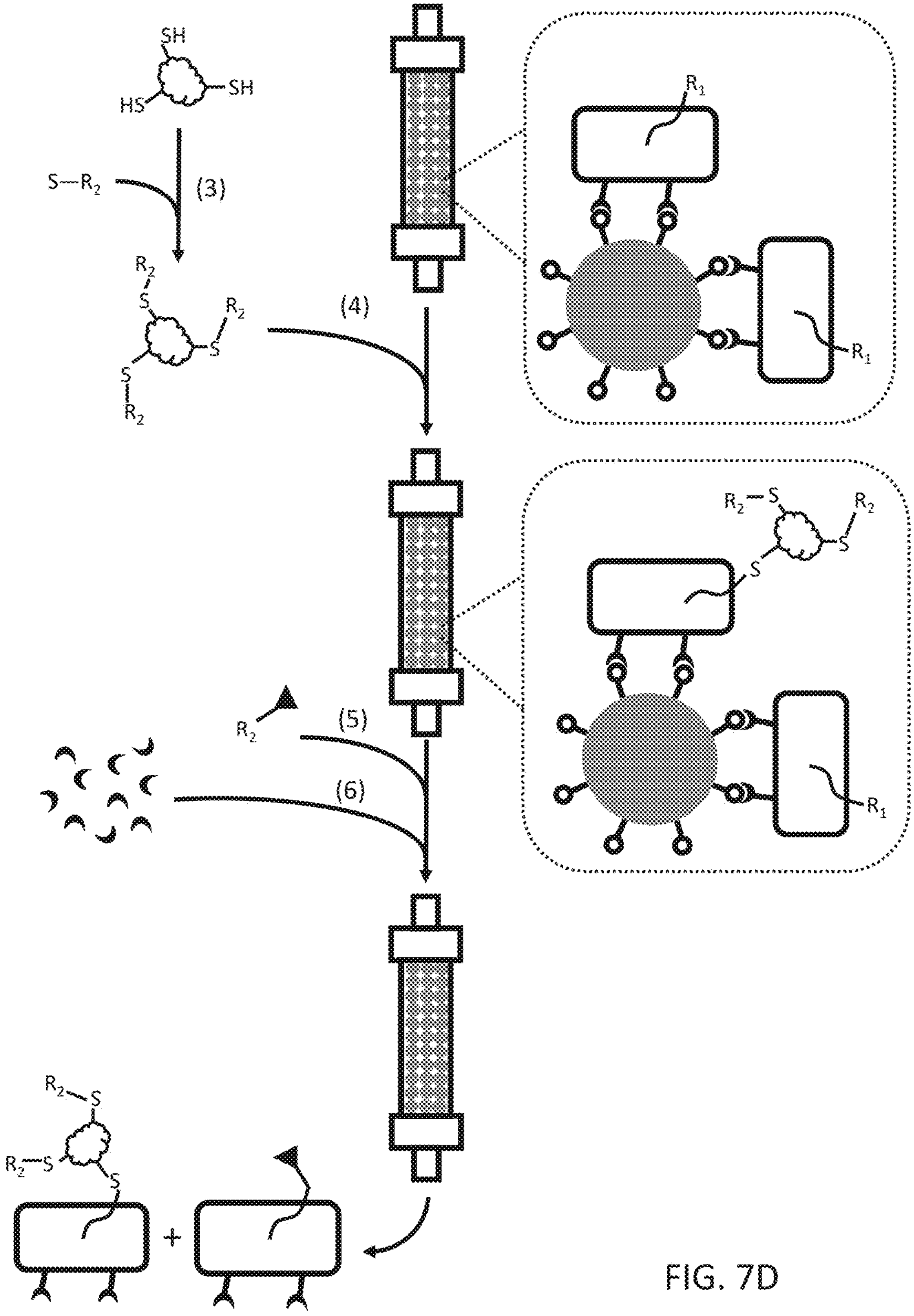
FIG. 7D illustrates a method for increasing diversity of functionalized proteins attached to immobilized particles and harvesting the particles to obtain separate fractions of particle-attached proteins.

The combined process of FIG. 7A and FIG. 7C exemplifies a method in which a protein sample can be cyclically modified and attached to particles. In the example shown, proteins are modified using different conditions in each cycle, thereby increasing the variety of different proteins attached to particles. It will be understood that a similar cyclic process can be used in which proteins are subjected to similar functionalization conditions during each cycle. This can be beneficial when complete functionalization is difficult to achieve in a single reaction. Although the combined process is exemplified for a sample of different proteins, a cyclic functionalization and attachment process can be used for a plurality of proteins that are the same (e.g. a homogenous protein sample). The combined process of FIG. 7A and FIG. 7C yields a mixed fraction of proteins modified in each of the cycles. An alternative process can be used to elute separated fractions, for example, as illustrated in FIG. 7D. In this process, the product of step three is contacted with immobilized particles in a column that lacks particles that are attached to proteins from the steps shown in FIG. 7A. The column can be a separate column from that used in FIG. 7A or the column can be the same one used in FIG. 7A, albeit after particles attached to amino modified proteins have been eluted and new particles have been immobilized in the column. Accordingly, particles eluted from the column after steps five and six will include the sulfhydryl modified proteins, but not the amino modified proteins. In this way, separate protein factions obtained from respective cycles can be obtained. The protein-attached particles can then be used in a downstream process, for example, being attached to an array for an analytical assay.

Accordingly, a method for attaching a particle to a protein, can include steps of (a) forming a reaction mixture including: (i) a plurality of proteins, wherein individual proteins of the plurality of proteins each include a plurality of first reactive moieties, and (ii) a plurality of immobilized particles, wherein individual immobilized particles of the plurality of immobilized particles each includes a second reactive moiety, wherein the second reactive moiety of the immobilized particles is reactive with the first reactive moieties of the proteins, and wherein the immobilized particles are attached to one or more solid supports; (b) reacting a first reactive moiety of a protein in the reaction mixture with a second reactive moiety of an immobilized particle in the reaction mixture to attach the protein to the immobilized particle via a bond formed between the first reactive moiety of the protein and the second reactive moiety of the immobilized particle, thereby forming an immobilized particle-protein conjugate; (c) detaching the immobilized particle-protein conjugate from the solid support, thereby producing a solution-phase particle-protein conjugate; and (d) removing unreacted proteins from the reaction mixture after step (b) and repeating step (a) using the unreacted proteins instead of the plurality of proteins. Optionally, the method can further include modifying the unreacted proteins to have additional first reactive moieties after step (b) and prior to the repeating of step (a). The additional first reactive moieties can be attached to the unreacted proteins using an attachment chemistry that differs from chemistry used to attach the first reactive moieties to the plurality of proteins prior to step (a). For example, the attachment chemistry used to attach the additional first reactive moieties to the unreacted proteins can modify different amino acid residue types than the residue types modified by the chemistry used to attach the first reactive moieties to the plurality of proteins prior to step (a).

Optionally, various reagents that pass over solid support(s) in a process of attaching proteins to particles, or fractions that are removed from the solid support(s), can be observed to facilitate evaluation of the process. For example, components used in the process can include exogenous or endogenous labels that are detectable by an appropriate detector. An optical detector can be useful, for example, being configured to detect UV absorbance at or around the wavelengths of 260 nm and 280 nm to determine relative amounts of nucleic acid and protein in a fraction. A 260 nm/280 nm ratio of about 0.6 is generally considered to be indicative of pure protein (absent nucleic acid) and a ratio of about 1.8 or higher is indicative of pure DNA. The expected 260 nm/280 nm ratio for protein attached to a given structured nucleic acid particle (SNAP) can be used to identify fractions containing SNAP-attached proteins. Alternatively proteins and/or SNAPs can contain exogenous labels and a detector that is appropriate to the labels can be used to evaluate and partition fractions. Those skilled in the art will recognize appropriate combinations of various particles, labels, analytes and detectors that can facilitate similar evaluation and partitioning. Particles that do not attach to proteins can be identified based on having been quenched as set forth above. For example, a quenching agent can include a label that produces a detectable signal or a ligand that is detectable due to binding to a receptor that produces a detectable signal.

Optionally, a column, or other fluid device used to attach proteins to particles, can be placed in-line with a flow cell or other apparatus that will be used to perform an assay on particle-attached proteins. Exemplary assays include a binding assay, amino acid sequencing assay or other assay set forth herein or known in the art. Fluids that are removed from solid supports, for example, eluates from one or more columns exemplified in connection with FIGS. 7A to 7D, can be passed through a fluidic system that is configured to direct different fractions to different locations. For example, the fluidic system can include a multiport valve, such as a rotary valve, that is actuatable to direct particle-attached proteins to an array where an assay will be performed and to direct other fractions to a waste reservoir or other reservoir. By way of more specific example, the egress of a column that is used for attaching proteins to particles can be fluidically connected to a multiport valve and the valve can be fluidically connected to the ingress of a waste reservoir and to the ingress of a flow cell that houses a substrate to which particle-attached proteins will attach for an assay. Optionally a detection device, such as a UV detector, can be positioned to detect the eluate from the column, the detector can be configured to communicate with the valve and the valve can be configured to actuate based on the communication to deliver appropriate fractions to appropriate locations. Whether or not the optional detection device is present, an in-line fluidic system can provide the advantage of automating a process of attaching proteins to particles, attaching the resulting particle-attached proteins to analytical arrays and performing an assay on the resulting protein array.

The present disclosure provides methods for detecting particle-attached proteins. For example, a particle-attached protein can be detected by binding to a probe and detecting a signal derived from the binding event. In some configurations of the detection methods, a particle-attached protein can be detected by reaction with a reagent and detecting a product of the reaction such as a signal produced by the reaction. Particle-attached proteins can be detected using any of a variety of methods known in the art for assaying protein structure and function.

Accordingly, the present disclosure provides a method of binding a probe to a protein. The method can include steps of (a) forming a reaction mixture including: (i) a plurality of proteins, wherein individual proteins of the plurality of proteins each include a plurality of first reactive moieties, and (ii) a plurality of particles, wherein individual particles of the plurality of particles each include a second reactive moiety, wherein the second reactive moiety of the particles is reactive with the first reactive moieties of the proteins, and wherein the particles are in a first state; (b) reacting a first reactive moiety of a protein in the reaction mixture with a second reactive moiety of a particle in the reaction mixture to attach the protein to the particle via a bond formed between the first reactive moiety of the protein and the second reactive moiety of a particle, thereby forming a particle-protein conjugate; and (c) performing a binding reaction including: (i) the particle-protein conjugate, wherein the particle of the particle-protein conjugate is in a second state, and (ii) a probe having affinity for the protein, thereby forming a particle-complex conjugate comprising the probe bound to the protein of the particle-protein conjugate.

In some configurations, a method of binding a probe to a protein can include steps of (a) forming a reaction mixture including: (i) a plurality of proteins, wherein individual proteins of the plurality of proteins each includes a plurality of first reactive moieties, (ii) a plurality of immobilized particles, wherein individual immobilized particles of the plurality of immobilized particles each includes a second reactive moiety, wherein the second reactive moiety of the immobilized particles is reactive with the first reactive moieties of the proteins, and wherein the immobilized particles are attached to a solid support; (b) reacting a first reactive moiety of a protein in the reaction mixture with a second reactive moiety of an immobilized particle in the reaction mixture to attach the protein to the immobilized particle via a bond formed between the first reactive moiety of the protein and the second reactive moiety of the immobilized particle; and (c) detaching the immobilized particle from the solid support, thereby producing a particle-protein conjugate including the protein attached to the particle in solution; and (d) binding a probe to the protein of the particle-protein conjugate.

Any of a variety of affinity reagents can be used for detection of particle-attached proteins (again, configurations exemplified herein for proteins can be extended to other analytes). Any molecule or other substance that is capable of specifically or reproducibly binding to a protein can be used as an affinity reagent. An affinity reagent can be larger than, smaller than or the same size as the protein. An affinity reagent may form a reversible or irreversible bond with a protein. An affinity reagent may bind with a protein in a covalent or non-covalent manner. Affinity reagents may include reactive affinity reagents, catalytic affinity reagents (e.g., kinases, proteases, etc.) or non-reactive affinity reagents (e.g., antibodies or fragments thereof). An affinity reagent can be non-reactive and non-catalytic, thereby not permanently altering the chemical structure of a protein to which it binds. Affinity reagents that can be particularly useful for binding to proteins include, but are not limited to, antibodies or functional fragments thereof (e.g., Fab' fragments, $F(ab')_2$ fragments, single-chain variable fragments (scFv), di-scFv, tri-scFv, or microantibodies), affibodies, affilins, affimers, affitins, alphabodies, anticalins, avimers, DARPins, monobodies, nanoCLAMPs, lectins or functional fragments thereof.

An affinity reagent can include a label. Exemplary labels include, without limitation, a fluorophore, luminophore, chromophore, nanoparticle (e.g., gold, silver, carbon nanotubes), heavy atom, radioactive isotope, mass label, charge label, spin label, receptor, ligand, nucleic acid barcode, polypeptide barcode, polysaccharide barcode, or the like. A label can produce any of a variety of detectable signals including, for example, an optical signal such as absorbance of radiation, luminescence (e.g. fluorescence or phosphorescence) emission, luminescence lifetime, luminescence polarization, or the like; Rayleigh and/or Mie scattering; magnetic properties; electrical properties; charge; mass; radioactivity or the like. A label may produce a signal with a characteristic frequency, intensity, polarity, duration, wavelength, sequence, or fingerprint. A label need not directly produce a signal. For example, a label can bind to a receptor or ligand having a moiety that produces a characteristic signal. Such labels can include, for example, nucleic acids that are encoded with a particular nucleotide sequence, avidin, biotin, non-peptide ligands of known receptors, or the like.

A particle-attached protein can be detected in a fluid phase or on a solid phase. For fluid phase configurations, a fluid containing one or more particle-attached proteins can be mixed with another fluid containing one or more affinity reagents. For solid phase configurations, one or more particle-attached proteins or affinity reagents can be attached to a solid support. One or more components that will participate in a binding event can be contained in a fluid and the fluid can be delivered to a particle-attached protein on a solid support.

One or more particle-attached proteins can be detected at single analyte resolution. Single-analyte resolution is the detection of, or ability to detect, the analyte on an individual basis, for example, as distinguished from its nearest neighbor in an array. For example, a single protein can be resolved from other proteins based on, for example, spatial or temporal separation from the other proteins. For example, the individual proteins (e.g. individual particle-attached proteins) can be located at different sites in an array. Alternatively to single-analyte resolution, a detection method can be carried out at ensemble-resolution or bulk-resolution. Bulk-resolution configurations acquire a composite signal from a plurality of different analytes or affinity reagents in a vessel or on a surface. For example, a composite signal can be acquired from a population of different protein-affinity reagent complexes in a well or cuvette, or on a solid support surface, such that individual complexes are not resolved from each other. Ensemble-resolution configurations can be configured to acquire a composite signal from a first collection of proteins or affinity reagents in a sample, such that the composite signal is distinguishable from signals generated by a second collection of proteins or affinity reagents in the sample. For example, the ensembles can be located at different sites in an array. Accordingly, the composite signal obtained from each site will be an average of signals from the ensemble, yet signals from different sites can be distinguished from each other.

One or more proteins (e.g. an array of different proteins) can be contacted with a plurality of different affinity reagents. For example, a plurality of affinity reagents (whether configured separately or as a pool) may include at least 2, 5, 10, 25, 50, 100, 250, 500 or more types of affinity reagents, each type of affinity reagent differing from the other types with respect to the epitope(s) recognized. Alternatively or additionally, a plurality of affinity reagents may include at most 500, 250, 100, 50, 25, 10, 5, or 2 types of affinity reagents, each type of affinity reagent differing from the other types with respect to the epitope(s) recognized. Different types of affinity reagents in a pool can be uniquely labeled such that the different types can be distinguished from each other. In some configurations, at least two, and up to all, of the different types of affinity reagents in a pool may be indistinguishably labeled. Alternatively or additionally to the use of unique labels, different types of affinity reagents can be delivered and detected serially when evaluating one or more proteins.

Detection of particle-attached proteins can be performed in a multiplex format. In multiplexed formats, different proteins can be attached to different unique identifiers (e.g. sites in an array), and the proteins can be manipulated and detected in parallel. For example, a fluid containing one or more different affinity reagents can be delivered to an array such that the proteins of the array are in simultaneous contact with the affinity reagent(s). Moreover, a plurality of sites can be observed in parallel allowing for rapid detection of binding events. A plurality of different proteins can have a complexity of at least 2, 5, 10, 100, $1\times10^3$, $1\times10^4$, $2\times10^4$, $3\times10^4$ or more different native-length protein primary sequences. Alternatively or additionally, a proteome or proteome subfraction that is analyzed in a method set forth herein can have a complexity that is at most $3\times10^4$, $2\times10^4$, $1\times10^4$, $1\times10^3$, 100, 10, 5, 2 or fewer different native-length protein primary sequences. The plurality of proteins can constitute a proteome or subfraction of a proteome. The total number of proteins of a sample that is detected, characterized or identified can differ from the number of different primary sequences in the sample, for example, due to the presence of multiple copies of at least some protein species. Moreover, the total number of proteins of a sample that is detected, characterized or identified can differ from the number of candidate proteins suspected of being in the sample, for example, due to the presence of multiple copies of at least some protein species, absence of some proteins in a source for the sample, or loss of some proteins prior to or during analysis. A particularly useful multiplex format uses an array of proteins and/or affinity reagents.

A particle-attached protein can be attached to a unique identifier using any of a variety of means. The particle can be covalently or non-covalently attached to a site or other unique identifier in an array. Exemplary attachments include, but are not limited to, those set forth herein in the context of attaching proteins to particles, attaching reactive moieties to proteins or attaching reactive moieties to particle. Exemplary reagents and methods for attaching structured nucleic acid particles to solid supports are set forth in US Pat. App. Pub. No. 2021/0101930 A1 or U.S. Pat. App. Ser. No. 63/159,500, each of which is incorporated herein by reference.

Binding can be detected using any of a variety of techniques that are appropriate to the assay components used. For example, binding can be detected by acquiring a signal from a label attached to an affinity reagent when bound to an observed protein, acquiring a signal from a label attached to protein when bound to an observed affinity reagent, or signal(s) from labels attached to an affinity reagent and protein. In some configurations a protein-affinity reagent complex need not be directly detected, for example, in formats where a nucleic acid tag or other moiety is created or modified as a result of binding between the protein and affinity reagent. Optical detection techniques such as luminescent intensity detection, luminescence lifetime detection, luminescence polarization detection, or surface plasmon resonance detection can be useful. Other detection techniques include, but are not limited to, electronic detection such as techniques that utilize a field-effect transistor (FET), ion-sensitive FET, or chemically-sensitive FET. Exemplary methods are set forth in U.S. Pat. No. 10,473,654 or U.S. patent application Ser. No. 17/523,869, which is incorporated herein by reference.

A particle-attached protein can be detected by obtaining multiple separate and non-identical measurements of the protein. In particular configurations, the individual measurements may not, by themselves, be sufficiently accurate or specific to make the characterization, but an aggregation of the multiple non-identical measurements can allow a characterization to be made with a high degree of accuracy, specificity and confidence. For example, the multiple separate measurements can include subjecting the particle-attached protein to reagents that are promiscuous with regard to recognizing multiple different proteins suspected of being present in a given sample from which the protein is derived. The use of promiscuous reagents can be particularly powerful in a multiplex format in which multiple different proteins are characterized in parallel. Accordingly, a first measurement carried out using a first promiscuous reagent may perceive a first subset of the different proteins without distinguishing one protein in the subset from another in the subset. A second measurement carried out using a second promiscuous reagent may perceive a second subset of proteins, again, without distinguishing one protein in the second subset from another in the second subset. However, a comparison of the first and second measurements can distinguish: (i) a protein that is uniquely present in the first subset but not the second; (ii) a protein that is uniquely present in the second subset but not the first; (iii) a protein that is uniquely present in both the first and second subsets; or (iv) a protein that is uniquely absent in the first and second subsets. The number of promiscuous reagents used, the number of separate measurements acquired, and degree of reagent promiscuity (e.g. the diversity of proteins recognized by the reagent) can be adjusted to suit the protein diversity expected for a particular sample.

For ease of explanation, compositions, apparatus and methods for detecting analytes are exemplified herein in the context of characterizing proteins using binding measurements. The examples set forth herein can be readily extended to characterizing other analytes (as an alternative or addition to proteins), or to the use of promiscuous reagents other than promiscuous affinity reagents, such as reagents that chemically modify analytes of interest. A composition, apparatus or method set forth herein can be used to characterize a protein, or moiety thereof, with respect to any of a variety of characteristics or features including, for example, presence, absence, quantity (e.g. amount or concentration), chemical reactivity, molecular structure, structural integrity (e.g. full length or fragmented), maturation state (e.g. presence or absence of pre- or pro-sequence in a protein), location (e.g. in an analytical system, subcellular compartment, cell or natural environment), association with another analyte or moiety, binding affinity for another analyte or moiety, biological activity, chemical activity or the like. A protein can be characterized with regard to a relatively generic characteristic such as the presence or absence of a common structural feature (e.g. amino acid sequence length, overall charge or overall pKa for a protein) or common moiety (e.g. a short amino acid sequence motif or post-translational modification for a protein). A protein can be characterized with regard to a relatively specific characteristic such as a unique amino acid sequence (e.g. for the full length of the protein or a motif), an RNA or DNA sequence that encodes the protein (e.g. for the full length of the protein or a motif), or an enzymatic or other activity that identifies the protein. A characterization can be sufficiently specific to identify a protein, for example, at a level that is considered adequate or unambiguous by those skilled in the art.

In particular configurations, a particle-attached protein can be detected using one or more affinity reagents having known or measurable binding affinity for the protein. For example, an affinity reagent can bind a protein to form a complex and a signal produced by the complex can be detected. A protein that is detected by binding to a known affinity reagent can be identified based on the known or predicted binding characteristics of the affinity reagent. For example, an affinity reagent that is known to selectively recognize a candidate protein suspected of being in a sample, without substantially binding to other proteins in the sample, can be used to identify the candidate protein in the sample merely by observing the binding event. This one-to-one correlation of affinity reagent to candidate protein can be used for identification of one or more proteins. However, as the protein complexity (i.e. the number and variety of different proteins) in a sample increases, or as the number of different candidate proteins to be identified increases, the time and resources to produce a commensurate variety of affinity reagents having one-to-one specificity for the proteins approaches limits of practicality.

Methods set forth herein, can be advantageously employed to overcome these constraints. In particular configurations, the methods can be used to identify a number of different candidate proteins that exceeds the number of affinity reagents used. For example, the number of candidate proteins identified can be at least 5 fold, 10 fold, 25 fold, 50 fold, 100 fold or more than the number of affinity reagents used. This can be achieved, for example, by (1) using promiscuous affinity reagents that bind to multiple different candidate proteins suspected of being present in a given sample, and (2) subjecting the protein sample to a set of promiscuous affinity reagents that, taken as a whole, are expected to bind each protein in a different combination, such that each protein is expected to be encoded by a unique profile of binding and non-binding events. Promiscuity of an affinity reagent is a characteristic that can be understood relative to a given population of proteins. Promiscuity can arise due to the affinity reagent recognizing an epitope that is known to be present in a plurality of different candidate proteins, wherein the candidate proteins are suspected of being present in the given population of proteins. For example, epitopes having relatively short amino acid lengths such as dimers, trimers, or tetramers are expected to occur in a substantial number of different proteins in the human proteome. Alternatively or additionally, a promiscuous affinity reagent can recognize different epitopes (i.e. epitopes having a variety of different structures), the different epitopes being present in a plurality of different candidate proteins. For example, a promiscuous affinity reagent that is designed or selected for its affinity toward a first trimer epitope may bind to a second epitope that has a different sequence of amino acids when compared to the first epitope.

Although performing a single binding reaction between a promiscuous affinity reagent and a complex protein sample may yield ambiguous results regarding the identity of the different proteins to which it binds, the ambiguity can be resolved when the results are combined with other identifying information about those proteins. The identifying information can include characteristics of the protein such as length (i.e. number of amino acids), hydrophobicity, charge to mass ratio, isoelectric point, chromatographic fractionation behavior, enzymatic activity, presence or absence of post translational modifications or the like. The identifying information can include results of binding with other promiscuous affinity reagents. For example, a plurality of different promiscuous affinity reagents can be contacted with a complex population of proteins, wherein the plurality is configured to produce a different binding profile for each candidate protein suspected of being present in the population. In this example, each of the affinity reagents is distinguishable from the other affinity reagents, for example, due to unique labeling (e.g. different affinity reagents have different luminophore labels), unique spatial location (e.g. different affinity reagents are located at different sites in an array), and/or unique time of use (e.g. different affinity reagents are delivered in series to a population of proteins). Accordingly, the plurality of promiscuous affinity reagents produces a binding profile for each individual protein that can be decoded to identify a unique combination of epitopes present in the individual protein, and this can in turn be used to identify the individual protein as a particular candidate protein having the same or similar unique combination of epitopes. The binding profile can include observed binding events as well as observed non-binding events and this information can be compared to the presence and absence of epitopes, respectively, in a given candidate protein to make a positive identification.

In some configurations, distinct and reproducible binding profiles may be observed for some or even a substantial majority of proteins that are to be identified in a sample. However, in many cases one or more binding events produces inconclusive or even aberrant results. For example, observation of binding outcome for a single-molecule binding event can be particularly prone to ambiguities due to stochasticity in the behavior of single molecules when observed using certain detection hardware. The present disclosure provides methods that provide accurate protein identification despite ambiguities and imperfections that can arise in many contexts. In some configurations, methods for identifying, quantitating or otherwise characterizing one or more proteins in a sample utilize a binding model that evaluates the likelihood or probability that one or more candidate proteins that are suspected of being present in the sample will have produced an empirically observed binding profile. The binding model can include information regarding expected binding outcomes (e.g. binding or non-binding) for binding of one or more affinity reagent with one or more candidate proteins. The information can include an a priori characteristic of a candidate protein, such as presence or absence of a particular epitope in the candidate protein or length of the candidate protein. Alternatively or additionally, the information can include empirically determined characteristics such as propensity or likelihood that the candidate protein will bind to a particular affinity reagent. Accordingly, a binding model can include information regarding the propensity or likelihood of a given candidate protein generating a false positive or false negative binding result in the presence of a particular affinity reagent, and such information can optionally be included for a plurality of affinity reagents.

Methods set forth herein can be used to evaluate the degree of compatibility of one or more empirical binding profiles with results computed for various candidate proteins using a binding model. For example, to identify an unknown protein in a sample of many proteins, an empirical binding profile for the protein can be compared to results computed by the binding model for many or all candidate proteins suspected of being in the sample. In some configurations of the methods set forth herein, identity for the unknown protein is determined based on a likelihood of the unknown protein being a particular candidate protein given the empirical binding pattern, or based on the probability of a particular candidate protein generating the empirical binding pattern. Optionally a score can be determined from the measurements that are acquired for the unknown protein with respect to many or all candidate proteins suspected of being in the sample. A digital or binary score that indicates one of two discrete states can be determined. In particular configurations, the score can be non-digital or non-binary. For example, the score can be a value selected from a continuum of values such that an identity is made based on the score being above or below a threshold value. Moreover, a score can be a single value or a collection of values. Particularly useful methods for identifying proteins using promiscuous reagents, serial binding measurements and/or decoding with binding models are set forth, for example, in U.S. Pat. No. 10,473,654 US Pat. App. Pub. No. 2020/0318101 A1 or Egertson et al., *BioRxiv* (2021), DOI: 10.1101/2021.10.11.463967, each of which is incorporated herein by reference.

One or more compositions set forth herein can be provided in kit form including, if desired, a suitable packaging material. In one configuration, for example, a particle, solid support, protein, protein-attached particle, functionalization reagent and/or other composition set forth herein can be provided in a solution or suspension. Alternatively, one or more compositions can be provided as a solid, such as crystals or a lyophilized pellet. Accordingly, any combination of reagents or components that is useful in a method of the invention, such as those set forth herein previously in regard to particular methods, can be included in a kit.

The packaging material included in a kit can consist of one or more physical structures used to house the contents of the kit. The packaging material can be constructed by well-known methods, preferably to provide a sterile, contaminant-free environment. The packaging materials employed herein can include, for example, those customarily utilized in affinity reagent systems. Exemplary packaging materials include, without limitation, glass, plastic, paper, foil, and the like, capable of holding within fixed limits a component useful in the methods of the present disclosure.

Packaging material or other components of a kit can include a kit label which identifies or describes a particular method set forth herein. For example, a kit label can indicate that the kit is useful for detecting a particular protein or proteome. In another example, a kit label can indicate that the kit is useful for a therapeutic or diagnostic purpose, or alternatively that it is for research use only.

Instructions for use of the packaged reagents or components are also typically included in a kit. The instructions for use can include a tangible expression describing the reagent or component concentration or at least one assay method parameter, such as the relative amounts of kit components and sample to be admixed, maintenance time periods for reagent/sample admixtures, temperature, buffer conditions, and the like.

What is claimed is:

1. A method comprising (a) forming a reaction mixture comprising:
   (i) a plurality of proteins, wherein individual proteins of the plurality of proteins each comprise a plurality of first reactive moieties, wherein the plurality of proteins comprises at least 100 different primary protein structures, and
   (ii) a plurality of particles, wherein individual particles of the plurality of particles each comprise a structured nucleic acid particle and a second reactive moiety, wherein the second reactive moiety of the particles is reactive with the first reactive moieties of the proteins, and wherein each of the particles is immobilized on a solid support;

(b) reacting a first reactive moiety of a protein in the reaction mixture with a second reactive moiety of a particle in the reaction mixture to attach the protein to the particle via a bond formed between the first reactive moiety of the protein and the second reactive moiety of the particle, wherein the reacting yields no more than one protein attached to the particle, and wherein immobilization of the particles inhibits more than one of the particles in the reaction mixture from simultaneously contacting the protein, thereby forming an immobilized particle-protein conjugate on the solid support; and (c) detaching the immobilized particle-protein conjugate from the solid support in solution-phase, thereby producing a solution-phase particle-protein conjugate.

2. The method of claim 1, wherein the structured nucleic acid particles comprise nucleic acid origami.

3. The method of claim 1, wherein the individual particles each comprise a nucleic acid linker attaching the individual particle to the second reactive moiety.

4. The method of claim 1, wherein each of the individual particles comprises a single second reactive moiety.

5. The method of claim 1, further comprising quenching reactivity of the second reactive moiety or the first reactive moiety after step (b).

6. The method of claim 5, wherein the quenching comprises attaching a ligand to the second reactive moiety.

7. The method of claim 6, further comprising separating particles from the particle-protein conjugate via binding of a receptor to the ligand.

8. The method of claim 1, further comprising (d) binding a probe to the protein of the particle-protein conjugate.

9. The method of claim 8, further comprising (e) detecting the binding of the probe to the protein of the particle-protein conjugate.

10. The method of claim 8, further comprising attaching the particle-protein conjugate to a solid support prior to step (d), thereby binding the probe to the protein of the particle-protein conjugate on the solid support.

11. The method of claim 1, further comprising, after step (c), separating the particle-protein conjugate from particles that lack an attached protein.

12. The method of claim 11, further comprising attaching the protein-attached particles to a second solid support, thereby forming an array of protein-attached particles.

13. The method of claim 2, wherein the nucleic acid origami comprises a plurality of at least 50 oligonucleotides hybridized to a scaffold nucleic acid.

14. The method of claim 2, wherein the nucleic acid origami comprises a staple oligonucleotide hybridized to two regions of a scaffold nucleic acid that are separated from each other in the nucleotide sequence of the scaffold nucleic acid.

15. The method of claim 1, wherein the plurality of proteins comprises at least 60% of the proteins encoded by a human proteome.

16. The method of claim 1, wherein, prior to step (a), the plurality of proteins is modified to add the first reactive moieties to the proteins.

* * * * *